United States Patent [19]

Carson et al.

[11] Patent Number: 5,324,747
[45] Date of Patent: Jun. 28, 1994

[54] N-SUBSTITUTED ANILINES, INHIBITORS OF PHOSPHOLIPASES $A_2$

[75] Inventors: Mathew Carson, Nutley; Ru-Jen L. Han, Princeton Junction; Ronald A. LeMahieu, N. Caldwell; Vincent S. Madison, Mountain Lakes, all of N.J.

[73] Assignee: Hoffmann-La Roche Inc., Nutley, N.J.

[21] Appl. No.: 914,825

[22] Filed: Jul. 15, 1992

[51] Int. Cl.$^5$ .................. A61K 31/195; C07C 313/04; C07C 317/14; C07D 215/14

[52] U.S. Cl. .................................... 514/533; 514/120; 514/121; 514/311; 514/357; 514/510; 514/538; 514/539; 514/562; 514/566; 514/569; 546/172; 546/174; 546/335; 558/70; 560/12; 560/22; 560/40; 560/41; 560/43; 560/44; 560/45; 562/426; 562/430; 562/433; 562/443; 562/444; 562/448; 562/452; 562/453; 562/456; 562/457

[58] Field of Search ............. 546/172, 174, 335; 560/12, 22, 40, 43, 44, 45, 41; 562/426, 430, 433, 443, 444, 448, 456, 457, 452, 453; 558/70; 514/120, 121, 311, 357, 510, 533, 538, 539, 562, 566, 567

[56] References Cited

U.S. PATENT DOCUMENTS

| | | | |
|---|---|---|---|
| 2,655,532 | 10/1953 | Hopff et al. | 562/453 |
| 2,781,388 | 2/1957 | Mannheimer | 562/433 X |
| 2,804,474 | 8/1957 | Lew | 562/433 X |
| 4,234,744 | 11/1980 | Effenberger et al. | 562/553 X |
| 4,517,130 | 5/1985 | Baer | 562/453 X |
| 4,603,209 | 7/1986 | Tsien et al. | 562/452 X |
| 4,925,958 | 5/1990 | Schmierer et al. | 560/43 |

OTHER PUBLICATIONS

R. Y. Tsien, *Biochemistry*, 19, 2396-2404 (1980).
G. Schwarzenbach, A. Willi and R. O. Bach, *Helv. Chim. Acta.*, 30, 1303-1320 (1947).

Primary Examiner—Paul J. Killos
Assistant Examiner—Vera C. Clarke
Attorney, Agent, or Firm—George M. Gould; William G. Isgro

[57] ABSTRACT

Compounds of the formula

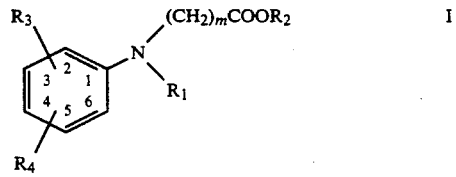

wherein $R_1$, $R_2$, $R_3$, $R_4$, $R_5$, $R_6$, $R_7$, $R_8$, n, m, o, p and q are as hereinafter set forth, and, when $R_2$ is hydrogen, pharmaceutically acceptable salts thereof with bases, are described. The compounds of formula 1 are potent inhibitors of phospholipases $A_2$ ($PLA_2$'s) and are therefore useful in the treatment of inflammatory diseases, such as psoriasis, inflammatory bowel disease, asthma, allergy, arthritis, dermatitis, gout, pulmonary disease, myocardial ischemia/reperfusion, and trauma induced inflammation, such as spinal cord injury.

44 Claims, No Drawings

N-SUBSTITUTED ANILINES, INHIBITORS OF PHOSPHOLIPASES $A_2$

BRIEF SUMMARY OF THE INVENTION

The invention relates to compounds of the formula $$R_3 \diagdown \underset{R_4}{\underset{|}{\text{[benzene ring, positions 1,2,3,4,5,6]}}} \diagup N \diagup (CH_2)_m COOR_2 \diagdown R_1 \qquad 1$$

wherein
$R_1$ is hydrogen or $—(CH_2)_mCOOR_2$;
$R_2$ is hydrogen, $(R_6)_2N(CH_2)_2—$, $R_6COOCH_2—$ or $—CH_2CON(CH_2CH_2OH)_2$;
$R_3$ is hydrogen, nitro, hydroxy, amino, $CH_3(CH_2)_nS(O)_{0-2}$; $CH_3(CH_2)_n—$, $CH_3(CH_2)_nO—$, $R_5COO—$, $R_5OOC—$, $R_5HNCOO—$, $R_5NHCO—$, $R_5CONH—$, $R_5NHCONH—$, $[CH_3(CH_2)_n]_2NCO—$, $CH_3(CH_2)_nCHOHCH_2O—$, (2-quinolinyl)methoxy, oleyloxy, linoleyloxy, $R_8OOC(CH_2)_oO—$, $(R_6O)_2PO(CH_2)_pO—$, (HO)$(R_6O)PO(CH_2)_pO—$, $R_6[O(CH_2)_2]_qO—$, $R_7(CH_2)_pO—$, or $—O(CH_2)_p$-pyridinium$^+$(OH$^-$);
$R_4$ is $CH_3(CH_2)_n—$, $CH_3(CH_2)_nO—$, $CF_3SO_2NH—$, $R_5COO—$, $R_5OOC—$, $R_5HNCOO—$, $R_5NHCO—$, $R_5NHCONH—$, $[CH_3(CH_2)_n]_2NCO—$, $CH_3(CH_2)_nCHOHCH_2O—$, carboxy, (2-quinolinyl)methoxy, oleyloxy, linoleyloxy, $R_8OOC(CH_2)_oO—$, $R_6[O(CH_2)_2]_qO—$, $R_7(CH_2)_pO—$;
$R_5$ is $CH_3(CH_2)_n—$, 1-adamantyl or diphenylmethyl;
$R_6$ is lower alkyl;
$R_7$ is 1- or 2-naphthyloxy, 1-, 2- or 3-pyridinyloxy, 2,3- or 3,4-dihydroxyphenyl, 6,7-dihydroxy-2-naphthyl, phenyl, phenoxy or substituted phenyl or phenoxy, wherein the substituent is selected from the group consisting of lower alkyl, lower alkoxy, hydroxy, nitro, amino, halo, $R_6S(O)_{0-2}—$, carboxy, carboxy-lower alkyl or phenyl;
$R_8$ is hydrogen or lower alkyl;
n is an integer from 0 to 17;
m is an integer from 1 to 3;
o is an integer from 1 to 10;
p is an integer from 2 to 18, and
q is an integer from 1 to 6;
and, when $R_2$ is hydrogen, pharmaceutically acceptable salts thereof with bases.

The compounds of formula 1 are potent inhibitors of phospholipases $A_2$ (PLA$_2$'s) and are therefore useful in the treatment of inflammatory diseases, such as psoriasis, inflammatory bowel disease, asthma, allergy, arthritis, dermatitis, gout, pulmonary disease, myocardial ischemia, and trauma induced inflammation, such as spinal cord injury.

In another aspect, the invention relates to compositions and methods of use comprising the compounds of formula 1.

BACKGROUND OF THE INVENTION

Phospholipases $A_2$ (PLA$_2$'s) are a class of enzymes which catalyze the hydrolysis of membrane phospholipids at the sn-2 position leading to free fatty acids and lysophospholipid. Arachidonic acid is stored in the cell membrane as an ester almost exclusively at the 2-position of phospholipids. PLA$_2$ acts to release arachidonic acid from phospholipids in what is believed to be the rate controlling step which ultimately leads to the products of the arachidonic acid cascade. Free arachidonic acid is rapidly metabolized by cyclooxygenase to give prostaglandins and thromboxane or by lipoxygenses to form hydroxy fatty acids and leukotrienes. Prostaglandins and leukotrienes are important mediators of inflammation and hydroxy fatty acids such as leukotriene B$_4$ act as chemotactic agents for neutrophils and eosinophils and may cause cell migration to sites of inflammation. Lysophospholipids are cytotoxic and have also been implicated in several inflammatory conditions. In addition, platelet activating factor (PAF) can be formed by the action of an acetyl transferase on a 1-alkyl-2-lysophospholipid. PAF is a potent platelet aggregating substance and causes various inflammatory conditions such as erythema, vascular permeability and cellular chemotaxis. These facts provide support for the utilization of an inhibitor of PLA$_2$'s as therapy for various inflammatory conditions.

DETAILED DESCRIPTION OF THE INVENTION $$R_3 \diagdown \underset{R_4}{\underset{|}{\text{[benzene ring, positions 1,2,3,4,5,6]}}} \diagup N \diagup (CH_2)_m COOR_2 \diagdown R_1 \qquad 1$$

wherein
$R_1$ is hydrogen or $—(CH_2)_mCOOR_2$;
$R_2$ is hydrogen, $(R_6)_2N(CH_2)_2—$, $R_6COOCH_2—$ or $—CH_2CON(CH_2CH_2OH)_2$;
$R_3$ is hydrogen, nitro, hydroxy, amino, $CH_3(CH_2)_nS(O)_{0-2}—$, $CH_3(CH_2)_n—$, $CH_3(CH_2)_nO—$, $R_5COO—$, $R_5OOC—$, $R_5HNCOO—$, $R_5NHCO—$, $R_5CONH—$, $R_5NHCONH—$, $[CH_3(CH_2)_n]_2NCO—$, $CH_3(CH_2)_nCHOHCH_2O—$, (2-quinolinyl)methoxy, oleyloxy, linoleyloxy, $R_8OOC(CH_2)_oO—$, $(R_6O)_2PO(CH_2)_pO—$, (HO)$(R_6O)PO(CH_2)_pO—$, $R_6[O(CH_2)_2]_qO—$, $R_7(CH_2)_pO—$, or $—O(CH_2)_p$-pyridinium$^+$(OH$^-$);
$R_4$ is $CH_3(CH_2)_n—$, $CH_3(CH_2)_nO—$, $CF_3SO_2NH—$, $R_5COO—$, $R_5OOC—$, $R_5HNCOO—$, $R_5NHCO—$, $R_5NHCONH—$, $[CH_3(CH_2)_n]_2NCO—$, $CH_3(CH_2)_nCHOHCH_2O—$, carboxy, (2-quinolinyl)methoxy, oleyloxy, linoleyloxy, $R_8OOC(CH_2)_oO—$, $R_6[O(CH_2)_2]_qO—$, $R_7(CH_2)_pO—$;
$R_5$ is $CH_3(CH_2)_n—$, 1-adamantyl or diphenylmethyl;
$R_6$ is lower alkyl;
$R_7$ is 1- or 2-naphthyloxy, 1-, 2- or 3-pyridinyloxy, 2,3- or 3,4-dihydroxyphenyl, 6,7-dihydroxy-2-naphthyl, phenyl, phenoxy or substituted phenyl or phenoxy, wherein the substituent is selected from the group consisting of lower alkyl, lower alkoxy, hydroxy, nitro, amino, halo, $R_6 S(O)_{0-2}—$, carboxy, carboxy-lower alkyl or phenyl;
$R_8$ is hydrogen or lower alkyl;
n is an integer from 0 to 17;
m is an integer from 1 to 3;
o is an integer from 1 to 10;
p is an integer from 2 to 18, and
q is an integer from 1 to 6;

and, when $R_2$ is hydrogen, pharmaceutically acceptable salts thereof with bases.

As used herein, the term "lower alkyl", alone or in combination, denotes a straight or branched chain saturated hydrocarbon containing 1 to 7 carbon atoms, preferably from 1 to 4 carbon atoms, for example, methyl, ethyl, propyl, isopropyl, butyl, dimethylethyl, neopentyl, pentyl, heptyl, and the like. The term "lower alkoxy" denotes an alkyl ether group in which the alkyl group is as described above, for example, methoxy, ethoxy, propoxy, pentoxy and the like.

The term "halogen" denotes all the halogens, for example, bromine, chlorine, fluorine and iodine.

A preferred group of compounds of formula 1 are those wherein $R_1$ is —$(CH_2)_mCOOR_2$.

Still other preferred compounds of formula 1 are those wherein $R_1$ is —$(CH_2)_mCOOR_2$; and $R_2$ is hydrogen.

Preferred compounds of formula 1 are also those wherein $R_1$ is —$(CH_2)_mCOOR_2$, m is 1-2, $R_3$ and $R_4$ are the same and are $CH_3(CH_2)_nO$— or $CH_3(CH_2)_nNHCO$—, n is 3-17 and the substitution pattern is

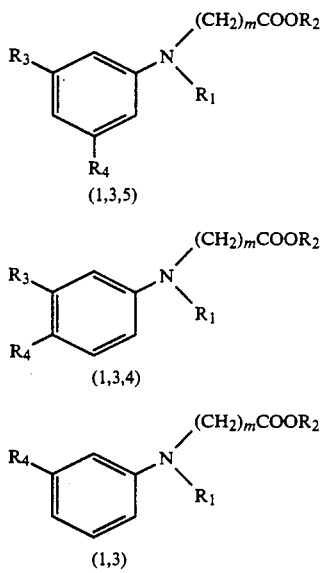

Another preferred group of compounds of formula 1 are those wherein $R_1$ is —$(CH_2)_mCOOR_2$ and m is 1-2 and $R_3$ is $CH_3(CH_2)_nO$—, wherein n is 3-17 and $R_4$ is selected from the group consisting of $R_8OOC(CH_2)_oO$, $R_6[O(CH_2)_2]_qO$—, $R_7(CH_2)_pO$—, $R_5OOC$— and $CF_3SO_2NH$— and the substitution pattern is 1, 3, 5.

More preferred compounds of formula 1 are those wherein $R_1$ is $HOOCCH_2$—, m is 1, $R_2$ is hydrogen and $R_3$ and $R_4$ (a) are both $CH_3(CH_2)_nO$— or $CH_3(CH_2)_nNHCO$— wherein n is 3-17 and the substitution pattern is 1,3,5 or 1,3,4, or (b) $R_4$ is $CH_3(CH_2)_nO$— wherein n is 9-17 and $R_3$ is hydrogen and the substitution pattern is 1,3 or (c) $R_3$ is $CH_3(CH_2)_nO$— wherein n is 9-17 and $R_4$ is $R_8OOC(CH_2)_oO$— wherein o is 1-6, $R_7(CH_2)_pO$— wherein $R_7$ is 2,3-dihydroxyphenyl or substituted phenoxy and p is 2-10, carboxy, $CF_3SO_2NH$— or $R_6[O(CH_2)_2]_qO$— wherein q is 2-5 and the substitution pattern is 1,3,5.

Most preferred compounds of formula 1 are those wherein $R_1$ is $HOOCCH_2$—, $R_2$ is hydrogen, m is 1, $R_3$ and $R_4$ (a) are both $CH_3(CH_2)_nO$— wherein n is 7-13 and the substitution pattern is 1,3,5 or (b) $R_3$ is $C_{18}H_{37}O$— and $R_4$ is $R_8OOC(CH_2)_oO$— wherein $R_8$ is hydrogen or methyl and o is 1-4, carboxy, $CF_3SO_2NH$—, $R_6[O(CH_2)_2]_qO$— wherein q is 2-3, $R_7(CH_2)_pO$— wherein $R_7$ is 2,3-dihydroxyphenyl or unsubstituted or substituted phenoxy wherein the substituent is selected from the group consisting of lower alkoxy, hydroxy, nitro, amino, methylsulfinyl or methylsulfonyl and p is 3-6 and the substitution pattern is 1, 3, 5.

The preferred compounds of the invention are:
N-(carboxymethyl)-N-[3,5-bis(decyloxy)phenyl]glycine;
N-(carboxymethyl)-N-[3,5-bis(dodecyloxy)phenyl]glycine;
N-(carboxymethyl)-N-[3,5-bis(tetradecyloxy)phenyl]glycine;
N-(carboxymethyl)-N-[3-(octadecyloxy)-5-[(5-methoxy-5-oxopentyl)oxy]phenyl]glycine;
N-[3-(4-carboxybutoxy)-5-(octadecyloxy)phenyl]-N-(carboxymethyl)glycine;
N-(carboxymethyl)-N-[3-(octadecyloxy)-5-(3-phenoxypropoxy)phenyl]glycine;
N-(carboxymethyl)-N-[3-[3-(3-methoxyphenoxy)propoxy]-5-(octadecyloxy)phenyl]glycine;
N-(carboxymethyl)-N-[3-[3-(4-methoxyphenoxy)propoxy]-5-(octadecyloxy)phenyl]glycine;
N-(carboxymethyl)-N-[3-[3-(4-hydroxyphenoxy)propoxy]-5-(octadecyloxy)phenyl]glycine;
N-(carboxymethyl)-N-[3-[3-(3-nitrophenoxy)propoxy]-5-(octadecyloxy)phenyl]glycine;
N-(carboxymethyl)-N-[3-[3-(3-aminophenoxy)propoxy]-5-(octadecyloxy)phenyl]glycine;
N-(carboxymethyl)-N-[3-[2-[2-(2-ethoxyethoxy)ethoxy]ethoxy]-5-(octadecyloxy)phenyl]glycine;
N-(carboxymethyl)-N-[3-(methoxycarbonyl)-5-(octadecyloxy)phenyl]glycine;
N-[3-carboxy-5-(octadecyloxy)phenyl]-N-(carboxymethyl)glycine;
N-(carboxymethyl)-N-[3-[3-[4-(methylsulfonyl)phenoxy]propoxy]-5-(octadecyloxy)phenyl]glycine;
N-(carboxymethyl)-N-[3-[3-[4-(methylsulfonyl)phenoxy]propoxy]-5-(octadecyloxy)phenyl]glycine;
N-(carboxymethyl)-N-[3-[5-(2,3-dihydroxyphenyl)pentoxy]-5-(octadecyloxy)phenyl]glycine;
N-(carboxymethyl)-N-[3-[4-(2,3-dihydroxy-6-naphthalenyl)butoxy]-5-(octadecyloxy)phenyl]glycine; and
N-(carboxymethyl)-N-[3-(octadecyloxy)-5-[[(trifluoromethyl)sulfonyl]amino]phenyl]glycine.

Exemplary of other compounds of the invention are:
N-(carboxymethyl)-N-[3,5-bis(undecyloxy)phenyl]glycine;
N-(carboxymethyl)-N-[3,5-bis(nonyloxy)phenyl]glycine;
N-(carboxymethyl)-N-[3,5-bis(tridecyloxy)phenyl]glycine;
N-(carboxymethyl)-N-[3,5-bis[(dodecylamino)carbonyl]phenyl]glycine;
N-(carboxymethyl)-N-[3,5-bis[(octylamino)carbonyl]phenyl]glycine;
N-(carboxymethyl)-N-3,5-bis[(1-oxododecyl)amino]glycine;

N-(carboxymethyl)-N-3,5-bis[(1-oxotetradecyl-
)amino]glycine;
N-(carboxymethyl)-N-(3,5-dioctylphenyl)glycine;
N-(carboxymethyl)-N-(3,5-didodecylphenyl)glycine;
N-(carboxymethyl)-N-[3,5-bis[(1-oxooctyl)oxy]-
phenyl]glycine;
N-(carboxymethyl)-N-[3,5-bis[(1-oxododecyl)oxy]-
phenyl]glycine;
N-(carboxymethyl)-N-[3,5-bis[(octyloxy)carbonyl]-
phenyl]glycine;
N-(carboxymethyl)-N-[3,5-bis[(dodecyloxy)carbonyl]-
phenyl]glycine;
N-(carboxymethyl)-N-[[3-(octadecyloxy)-5-(1-oxopen-
tyl)oxy]phenyl]glycine;
N-(carboxymethyl)-N-[[3-(octadecyloxy)-5-(1-
oxononyl)oxy]phenyl]glycine;
N-(carboxymethyl)-N-[[3-(octadecyloxy)-5-(1-oxoun-
decyl)oxy]phenyl]glycine;
N-(carboxymethyl)-N-[3-(octadecyloxy)-5-(3-phenox-
ypentyloxy)phenyl]glycine;
N-(carboxymethyl)-N-[3-(octadecyloxy)-5-(3-phenox-
yethoxy)phenyl]glycine;
N-(carboxymethyl)-N-[3-(tetradecyloxy)-5-(3-phenox-
ypentyloxy)phenyl]glycine;
N-(carboxymethyl)-N-[3-(decyloxy)-5-(3-phenoxypen-
tyloxy)phenyl]glycine;
N-(carboxymethyl)-N-[3-(octadecyloxy)-4-(3-phenox-
ypentyloxy)phenyl]glycine;
N-(carboxymethyl)-N-[3-(octadecyloxy)-4-(3-phenoxy-
propoxy)phenyl]glycine;
N-(carboxymethyl)-N-[3-[3-[3-(methylsulfinyl)phenox-
y]propoxy]-5-(octadecyloxy)phenyl]glycine;
N-(carboxymethyl)-N-[3-[3-[2-(methylsulfinyl)phenox-
y]propoxy]-5-(octadecyloxy)phenyl]glycine;
N-(carboxymethyl)-N-[3-[3-[2-methoxyphenoxy)-
propoxy]-5-(octadecyloxy)phenyl]glycine;
N-(carboxymethyl)-N-[3-[3-(4-nitrophenoxy)propoxy]-
5-(octadecyloxy)phenyl]glycine;

N-(carboxymethyl)-N-[3-[3-(2-nitrophenoxy)propoxy]-
5-(octadecyloxy)phenyl]glycine;
N-(carboxymethyl)-N-[3-[3-(3-hydroxyphenoxy)-
propoxy]-5-(octadecyloxy)phenyl]glycine;
N-(carboxymethyl)-N-[3-[3-(2-hydroxyphenoxy)-
propoxy]-5-(octadecyloxy)phenyl]glycine;
N-(carboxymethyl)-N-[3-[3-(4-aminophenoxy)propox-
y]-5-(octadecyloxy)phenyl]glycine;
N-(carboxymethyl)-N-[3-[3-(2-aminophenoxy)propox-
y]-5-(octadecyloxy)phenyl]glycine;
N-(carboxymethyl)-N-[3-[3-(2,3-dihydroxyphenyl)-
propoxy]-5-(octadecyloxy)phenyl]glycine;
N-(carboxymethyl)-N-[3-[3-(3,4-dihydroxyphenyl)-
propoxy]-5-(octadecyloxy)phenyl]glycine;
N-(carboxymethyl)-N-[3-[5-(2,3-dihydroxyphenyl)pen-
toxy]-5-(tetradecyloxy)phenyl]glycine;
N-(carboxymethyl)-N-[3-[5-(2,3-dihydroxyphenyl)pen-
toxy]-5-(decyloxy)phenyl]glycine;
N-(carboxymethyl)-N-[3-[5-(2,3-dihydroxyphenyl)pen-
toxy]-4-(tetradecyloxy)phenyl]glycine;
N-(carboxymethyl)-N-[3-[2-(2,3-dihydroxy-6-naph-
thalenyl)ethoxy]-5-(octadecyloxy)phenyl}glycine;
N-(carboxymethyl)-N-[3-[4-(2,3-dihydroxy-6-naph-
thalenyl)butoxy]-5-(tetradecyloxy)phenyl}glycine;
N-(carboxymethyl)-N-[3-[4-(2,3-dihydroxy-6-naph-
thalenyl)butoxy]-4-(tetradecyloxy)phenyl}glycine;

N-(carboxymethyl)-N-[3-decyloxy-5-(3,6,9-trioxaun-
dec-1-yloxy)phenyl]glycine;
N-(carboxymethyl)-N-[2,3-bis(decyloxy)phenyl]gly-
cine;
N-(carboxymethyl)-N-[2,4-bis(decyloxy)phenyl]gly-
cine;
N-(carboxymethyl)-N-[2,5-bis(decyloxy)phenyl]gly-
cine; and the like.

The compounds of formula 1 can be prepared as set forth in Schemes 1-16.

5-(octadecyloxy)phenyl]glycine;

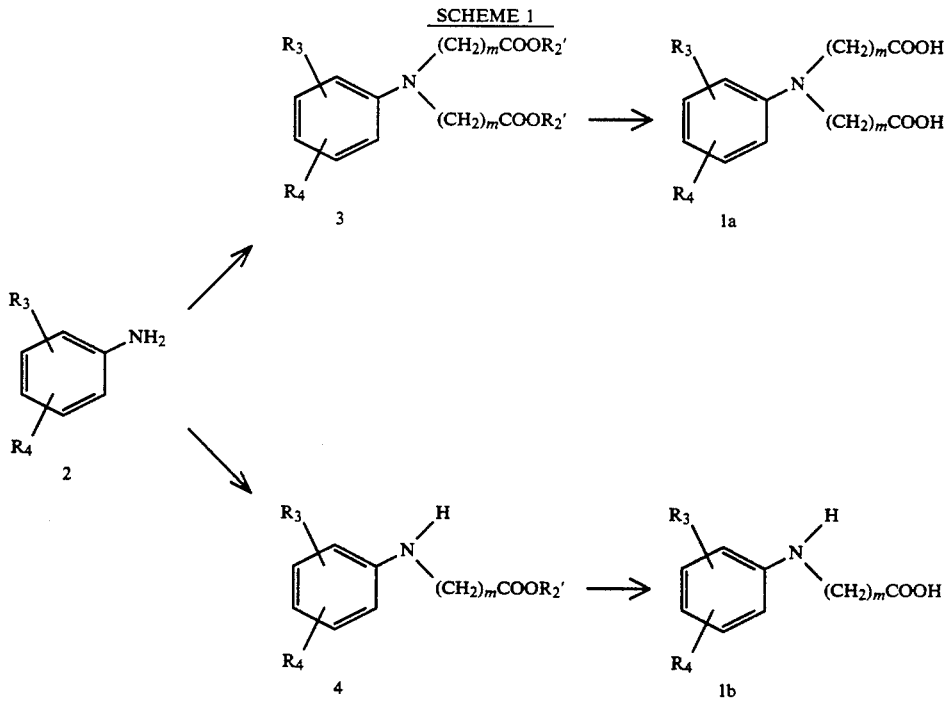

SCHEME 1 wherein R$_2$' is lower alkyl or benzyl and R$_3$, R$_4$, m are as previously described.

In Scheme 1 a substituted aniline of formula 2, which can be prepared according to one of the Schemes which follows, can be converted to the corresponding compound of the invention by a two step process. In the first step an aniline of formula 2 is converted to the corresponding dialkylated aniline of formula 3 by reaction with an excess of a bromo ester in the presence of a base such as 1,8-bis(dimethylamino)naphthalene (Proton Sponge) or an alkali metal carbonate in an anhydrous, polar, aprotic solvent such as acetonitrile, acetone or dimethylformamide (DMF) or mixtures thereof. The reaction is carried out at a temperature of from 56°–100°. Sodium iodide is usually added to facilitate the reaction. Alternatively, a compound of formula 2 can be converted to the corresponding monoalkylated aniline of formula 4 under similar reaction conditions but without using a large excess of the bromo ester. Intermediates of formulas 3 and 4 can be converted to the corresponding compounds of the invention of formula 1a and 1b by hydrolysis using an alkali metal hydroxide in a solvent mixture of water and a lower alkanol. In some cases, a co-solvent such as dioxane must be added to improve solubility. Hydrogenolysis can also be used for conversion of a compound of the formula 3 or 4 to the corresponding compound of formula 1a or 1b when the $R_2'$ group is benzyl. This is accomplished by shaking a solution of a compound of formula 3 or 4 with a palladium catalyst in a hydrogen atmosphere using an inert solvent such as ethyl acetate, tetrahydrofuran (THF) or DMF.

The substituted anilines of formula 2 required for the preparation of the compounds of the invention can be prepared as set forth in Schemes 2–9.

described, R' is benzyl or methyl, and R" is benzyl or t-butyl.

The process of Scheme 2 can be used for the preparation of disubstituted anilines of formula (2a) wherein $R_3^a$ and $R_4^a$ are the same. A known dihydroxy ester of formula 5 can be dialkylated to give the corresponding compound of formula 6 by heating with excess of the corresponding alkyl halide or epoxide using an alkali metal carbonate as a base in a solvent such as acetone or DMF or mixtures thereof. The ester of formula 6 can be hydrolyzed to the corresponding acid of formula 7 under standard conditions using an alkali metal hydroxide in a solvent mixture of water and a lower alkanol with added dioxide to improve solubility, if needed. A benzoic acid of formula 7 can be converted to the corresponding carbamate of formula 8 using the Curtius Reaction under the following conditions. An acid of formula 7 is converted to the corresponding acyl azide using diphenylphosphoryl azide in an inert, anhydrous solvent such as toluene or benzene in the presence of a tertiary amine such as triethylamine at temperatures of from 0°–30°. Heating the acyl azide solution at 60°–110° causes rearrangement to the corresponding isocyanate. Addition of benzyl alcohol or t-butyl alcohol followed by continued heating at 60°–100° results in formation of the corresponding carbamic acid benzyl ester or t-butyl ester of formula 8. The conversion of a compound of formula 7 to the corresponding compound of formula 8can also be carried out by heating a compound of formula 7, diphenylphosphoryl azide and triethylamine in t-butyl alcohol at 60°–83°. Finally, a carbamate of formula 8 can be converted to the corresponding disubstituted aniline of formula 2a by hydrogenolysis, if R" is benzyl, carried out by shaking with a palladium catalyst in a hydrogen atmosphere in an inert solvent such as ethyl acetate or THF. A carbamate of formula 8, if R" is t-butyl, is converted to the corresponding compound of formula 2a by treatment with trifluoroacetic acid in a solvent such as methylene chloride at a temperature of from 0°–30°.

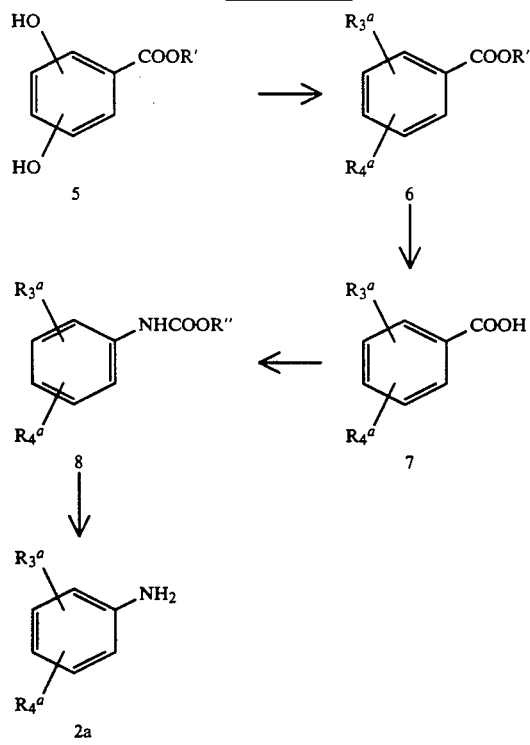

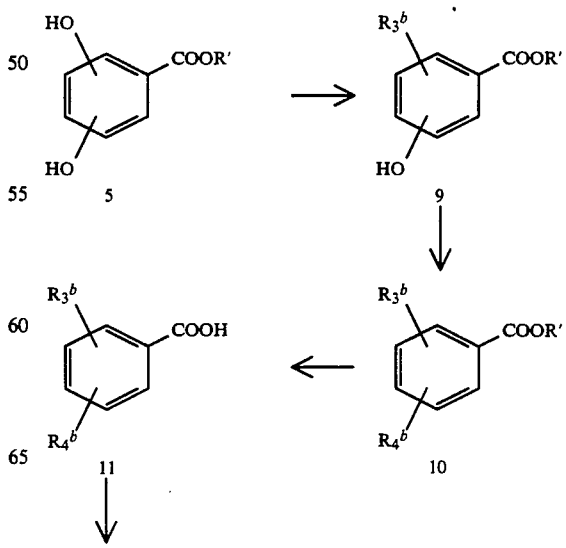

wherein $R_3^a$ and $R_4^a$ are the same, and are $CH_3(CH_2)_nO-$, $R_6OOC(CH_2)_oO-$, oleyloxy, linoleyloxy, $R_6[O(CH_2)_2]_qO-$, $R_7(CH_2)_pO-$ or $CH_3(CH_2)_nCHOHCH_2O-$, $R_6$ and $R_7$ are as previously -continued
SCHEME 3

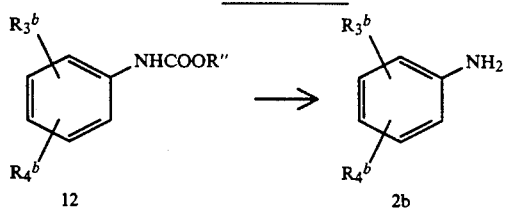

wherein $R_3^b$ and $R_4^b$ are different, and are $CH_3(CH_2)_nO-$, $R_5COO-$, $R_5HNCOO-$, oleyloxy, linoleyloxy, $R_6[O(CH_2)_2]_qO-$, $R_6OOC(CH_2)_oO-$, $R_7(CH_2)_pO-$ or $CH_3(CH_2)_nCHOHCH_2O-$, $R'$ is benzyl or methyl or $R''$ is benzyl or t-butyl.

The process of Scheme 3 can be used for the preparation of disubstituted anilines of formula 2b, wherein $R_3^b$ and $R_4^b$ are different. A known dihydroxy ester of formula 5 can be monoalkylated by heating with an equimolar amount of the corresponding alkyl halide using an alkali metal carbonate as the base in a solvent such as acetone or DMF or mixtures thereof. The desired monoalkylation product of formula 9 can be separated from the dialkylation product and the starting material of formula 5 using standard separation techniques. Alkylation of a compound of formula 9 using the same conditions but with a different alkyl bromide then provides the corresponding compound of formula 10 which can be hydrolyzed or hydrogenolyzed to the corresponding acid of formula 11. An acid of formula 11 is subjected to the Curtius Reaction to give the corresponding carbamate 12, which can be converted to the disubstituted aniline of formula 2b, as described in Scheme 2.

SCHEME 4

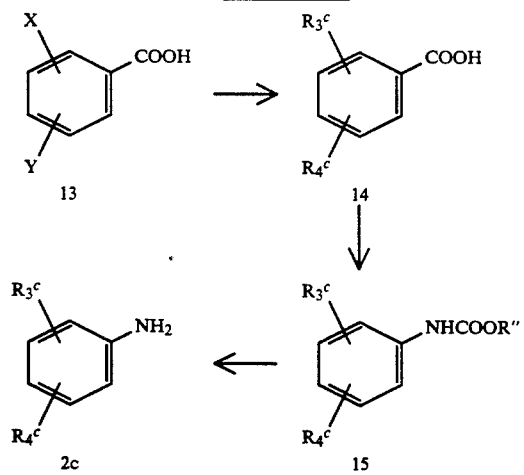

wherein X and Y are the same, and are OH or $NH_2$, $R_3^c$ and $R_4^c$ are the same, and are $R_5COO-$, $R_5NHCOO-$, $R_5CONH-$ or $R_5NHCONH-$, $R_5$ is as previously described, and $R''$ is benzyl or t-butyl.

In Scheme 4, a known dihydroxy or diaminobenzoic acid of formula 13 can be converted to the corresponding compound of formula 14 by treatment with the corresponding acid chloride or isocyanate in the presence of a tertiary amine such as triethylamine and a solvent such as methylene chloride or THF at a temperature of from 0°-30°. The resulting acid of formula 14 when subjected to the Curtius Reaction under conditions described earlier provides the corresponding carbamate of formula 15 which can be converted to the substituted aniline of formula 2c, as in Scheme 2.

SCHEME 5

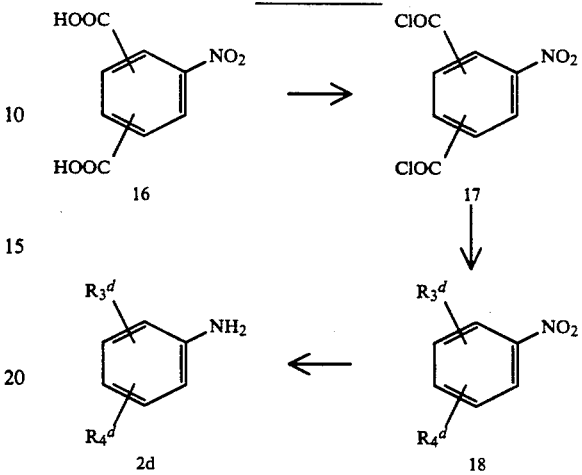

wherein $R_3^d$ and $R_4^d$ are the same, and are $R_5OOC-$, $R_5NHCO-$ or $[CH_3(CH_2)_n]_2NCO-$, and $R_5$ is as previously described.

In Scheme 5, a known dicarboxylic acid of formula 16 is converted to the corresponding diacid chloride of formula 17 by heating with thionyl chloride. Treatment of a compound of formula 17 with the corresponding alcohol or primary or secondary amine in the presence of a tertiary amine such as triethylamine in an inert solvent such as methylene chloride or THF at a temperature of from 0°-30° provides the corresponding compound of formula 18. Catalytic hydrogenation of a compound of formula 18 using a palladium catalyst in a solvent such as ethyl acetate or THF gives the corresponding substituted aniline of formula 2d.

SCHEME 6

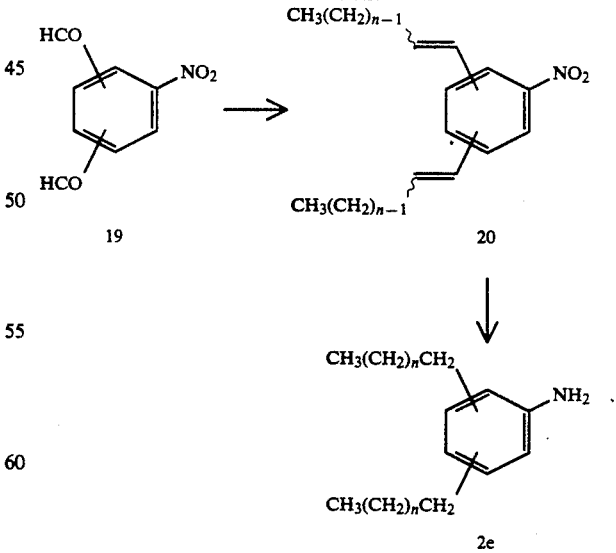

wherein n is as previously described.

In Scheme 6, a known dialdehyde of formula 19 is treated at 0°-30° with the corresponding Wittig reagent prepared under standard conditions (alkyl triphenylphosphonium bromide, alkyl lithium in THF at 0°) to give the corresponding mixture of (Z) and (E) isomers of formula 20. Hydrogenation of the double bonds using standard conditions, palladium catalyst in THF under hydrogen pressure, provides the corresponding substituted aniline of formula 2e.

SCHEME 7

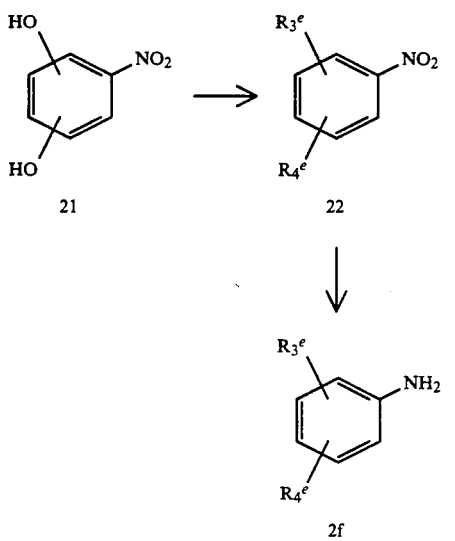

wherein $R_3^e$ and $R_4^e$ are identical, and are $CH_3(CH_2)_nO-$, $CH_3(CH_2)_nCHOHCH_2O-$, $R_5COO-$, $R_5HNCOO-$, $R_6[O(CH_2)_2]_qO-$, $R_6OOC(CH_2)_oO-$, or $R_7(CH_2)_pO-$, and $R_5$, $R_6$ and $R_7$ are as previously described.

In Scheme 7, a known dihydroxy compound of formula 21 is alkylated by treatment with the corresponding alkyl halide in the presence of an alkali metal carbonate in a solvent such as acetone or dimethylformamide or mixtures thereof at a temperature of from 56°–100° to give the corresponding compound of formula 22.

A compound of formula 21 can also be treated with the corresponding acid chloride or isocyanate in the presence of an organic base such as pyridine or triethylamine in a solvent such as methylene chloride or THF at a temperature of from 0°–50° to give the corresponding bis ester of formula 22 or the corresponding bis carbamate of formula 22. Catalytic hydrogenation of a compound of formula 22 using a palladium catalyst under standard conditions in a solvent such as ethyl acetate or THF gives the corresponding substituted aniline 2f.

SCHEME 8

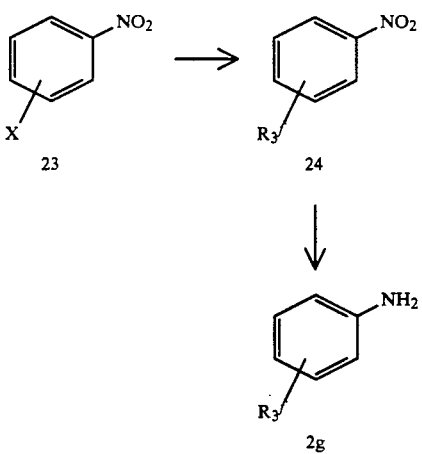

wherein X is OH or $NH_2$, $R_3^f$ is $CH_3(CH_2)_nO-$, $CH_3(CH_2)_nCHOHCH_2O-$, $R_5COO-$, $R_5NHCOO-$, $R_5CONH-$, $R_5NHCONH-$, $R_6[O(CH_2)_2]_qO-$ or $R_7(CH_2)_p-$, and n, q, p, $R_5$, $R_6$ and $R_7$ are as previously described In Scheme 8, a known nitro phenol or nitro aniline of formula 23 is treated with the corresponding alkyl halide, acid chloride or isocyanate under conditions described in Scheme 7 to give the corresponding compound of formula 24 which can be converted to the corresponding substituted aniline of formula 2g, using standard catalytic hydrogenation conditions.

SCHEME 9

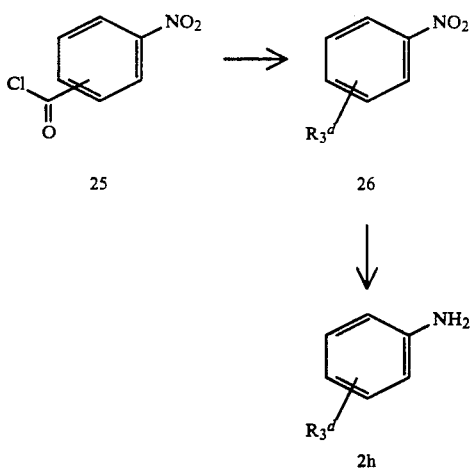

wherein $R_3^d$ is as previously described.

In Scheme 9, a known nitro acid chloride of formula 25 is treated with the corresponding primary or secondary amine or an alcohol in the presence of a base such as triethylamine in a solvent such as methylene chloride or THF at temperatures of from 0°–30° to give the corresponding compound of formula 26. Catalytic hydrogenation serves to convert a compound of formula 26 to the corresponding substituted aniline of formula 2h.

SCHEME 10

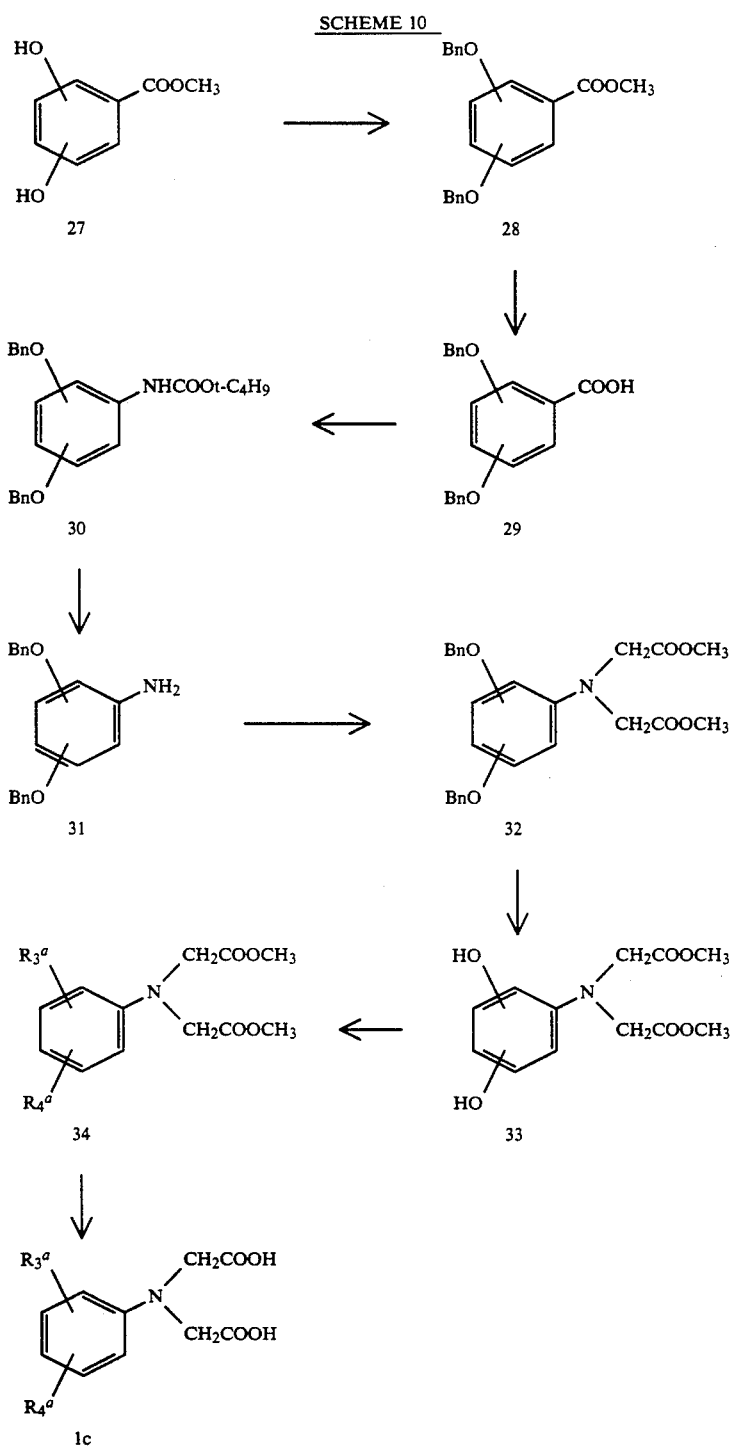

wherein $R_3{}^a$ and $R_4{}^a$ are the same, and are as previously described and Bn is benzyl.

Schemes 10–16 illustrate alternative methods to prepare compounds of the invention. In Scheme 10, a known dihydroxy ester of formula 27 is converted to the corresponding bis benzyl ether of formula 28 by alkylation with benzyl bromide under standard conditions and then to the corresponding acid of formula 29 by base hydrolysis. A compound of formula 29 is subjected to the Curtius Reaction under conditions described earlier to give the corresponding compound of formula 30 which is treated with trifluoracetic acid to yield the corresponding compound of formula 31. Treatment of a compound of formula 31 with excess methyl bromoacetate under conditions described in Scheme 1 gives the corresponding compound of formula 32. Catalytic hydrogenolysis of the resulting compound of formula 32 under standard conditions provides the corresponding compound of formula 33 which can be converted to the corresponding compound of formula 34 and then to 1c under conditions described in earlier Schemes.

SCHEME 11

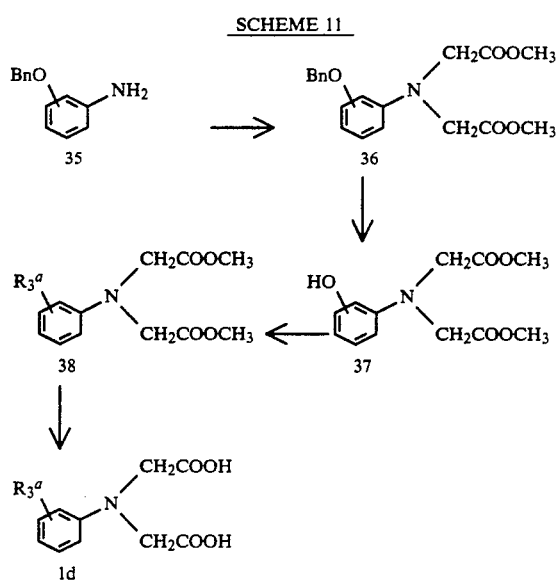

wherein $R_3^a$ is as previously described and Bn is benzyl.

The monosubstituted compounds of the invention of formula (1d) can be prepared from the known benzyloxy anilines of formula (35) as shown in Scheme 11 using conditions described in earlier Schemes.

SCHEME 12

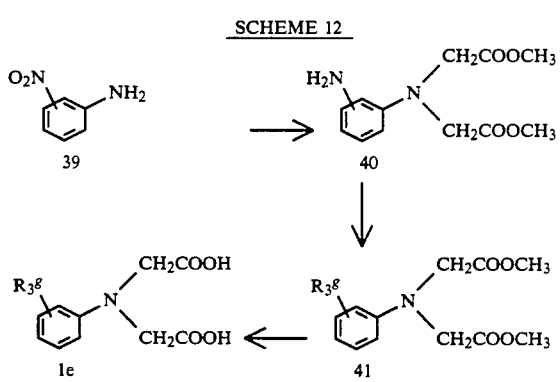

wherein $R_3^g$ is $R_5CONH-$ or $R_5NHCONH-$, and $R_5$ is as previously described.

In Scheme 12, a known nitro aniline of formula 39 can be converted to the corresponding compound of formula 40 by heating with excess methyl bromoacetate in the presence of a tertiary amine such as diisopropylethyl amine in a solvent such as acetonitrile or DMF, at temperatures of from 80°–110° followed by catalytic hydrogenation using a palladium catalyst under standard conditions. Treatment of a compound of formula 40 with the corresponding acid chloride or isocyanate in the presence of a tertiary amine such as triethylamine in a solvent such as methylene chloride at temperatures of from 0°–30° gives the corresponding compound of formula 41 which on base hydrolysis using an alkali metal hydroxide in a solvent mixture of water and a lower alkanol, with added dioxane to improve solubility in some cases, give the corresponding compound of formula 1e.

SCHEME 13

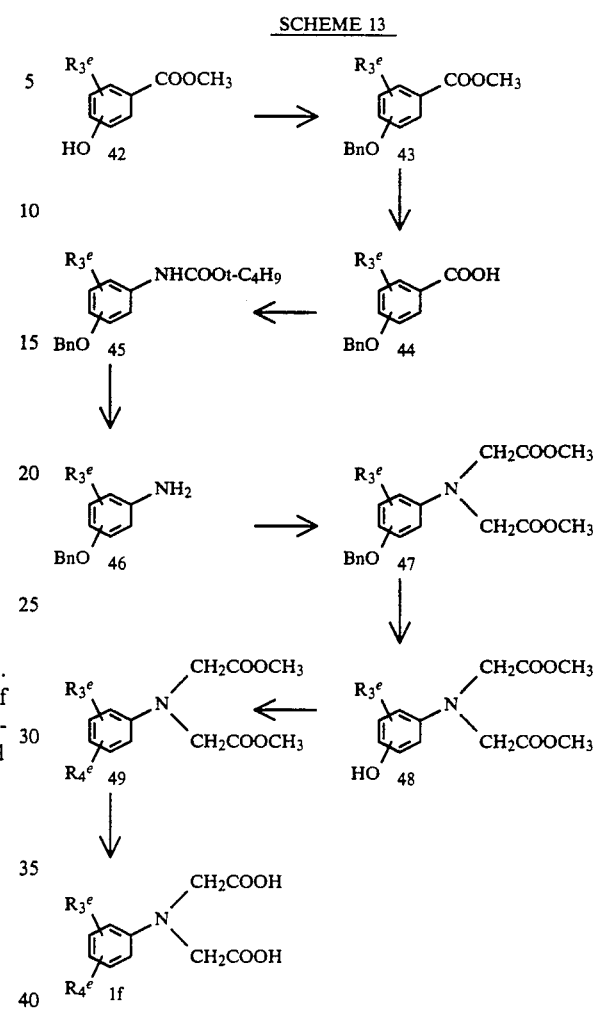

wherein $R_3^e$ and $R_4^e$, are different, and Bn is benzyl.

Compounds of formula 1f of the invention, wherein $R_3^e$ and $R_4^e$ are different, can also be prepared according to Scheme 13. A compound of formula 42 prepared according to Scheme 3 is converted to the corresponding benzyl ester of formula 43 and then to the corresponding acid of formula 44, t-butyl carbamate of formula 45 and aniline of formula 46, under the usual conditions. Alkylation of a compound of formula 46 with methyl bromoacetate, as described in Scheme 1, gives the corresponding compound of formula 47 from which the benzyl ether can be removed using catalytic hydrogenolysis to give the corresponding compound of formula 48. A different group can now be introduced by treatment with the corresponding alkyl bromide in the presence of an alkali metal carbonate such as potassium carbonate in a solvent such as acetone or DMF or mixtures thereof at a temperature of from 56°–100° to give the corresponding compound of formula 49. Base hydrolysis with an alkali metal hydroxide gives the corresponding compound of the invention of formula 1f.

SCHEME 14

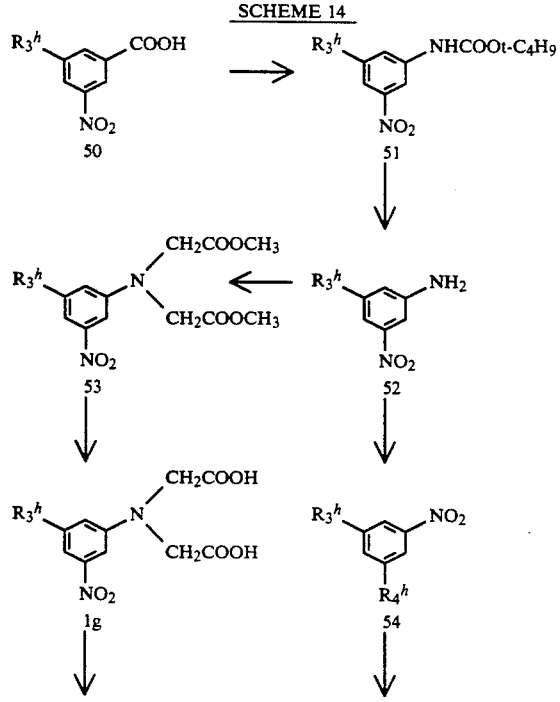
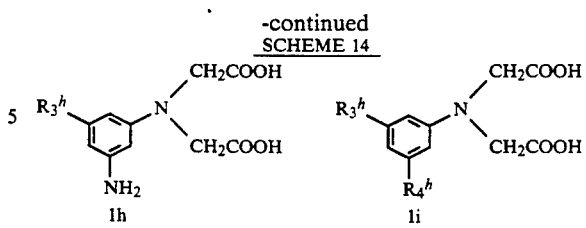

wherein $R_3^h$ is $CH_3(CH_2)_nO$—, $R_7(CH_2)_pO$— or $R_6[O(CH_2)_2]_qO$—, $R_4^h$ is $R_5CONH$— or $R_5NHCONH$—, and n, p, q, $R_5$, $R_6$ and $R_7$ are as defined previously.

In Scheme 14, a compound of formula 50, which is described in the Examples, can be converted by the Curtius Reaction to the corresponding carbamate of formula 51 and then by treatment with trifluoroacetic acid to the corresponding compound of formula 52 as described in earlier Schemes. Alkylation of the resulting compound of formula 52 with methyl bromoacetate under the usual conditions gives the corresponding compound of formula 53 which on base hydrolysis provides the compound of formula 1g. Catalytic hydrogenation of the resulting compound of formula 1g under standard conditions gives the corresponding compound of formula 1h. Treatment of a compound of formula 52 with the corresponding acid chloride or isocyanate and triethylamine as described in previous Schemes gives the corresponding compound of formula 54, which on catalytic hydrogenation followed by reaction with excess benzyl bromoacetate and finally catalytic hydrogenolysis gives the corresponding compound of formula 1i.

SCHEME 15

SCHEME 15

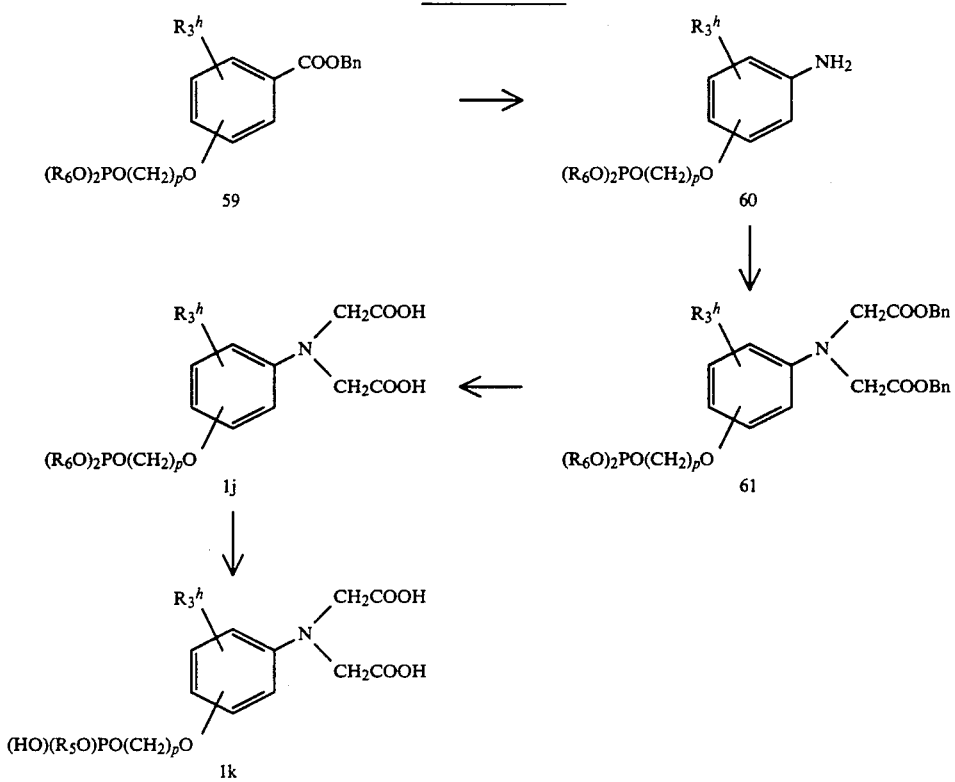

wherein $R_3^h$, $R_5$ and $R_6$ are as previously described, Bn is Benzyl and p is 2-12.

In Scheme 15, a compound of formula 55, which is described in the Examples which follow, can be alkylated with excess of the corresponding dibromoalkane using potassium carbonate as the base in a solvent such as acetone or DMF or mixtures thereof at temperatures of from 56°-100° to give the corresponding compound of formula 56. The Arbusov Reaction under standard conditions using triethyl phosphite at 150° serves to convert a compound of formula 56 to the corresponding compound of formula 57. Removal of the benzyl group by catalytic hydrogenolysis gave the corresponding compound of formula 58 which was converted using the Curtius Reaction via the corresponding benzyl carbamate of formula 59 followed by catalytic hydrogenolysis to the corresponding compound of formula 60. Alkylation of a compound of formula 60 with excess benzyl bromoacetate as described in earlier Schemes gives the corresponding compound of formula 61 which, after catalytic hydrogenolysis, provides the corresponding compound of formula 1j. Treatment of a compound of formula 1j with an alkali metal hydroxide in dimethylsulfoxide at 100°-190° gives the corresponding compound of formula 1k.

SCHEME 16

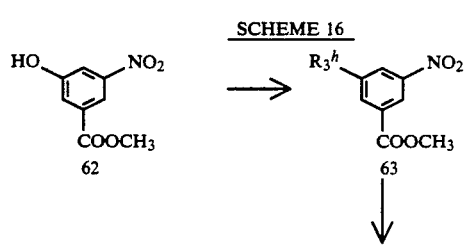

-continued
SCHEME 16

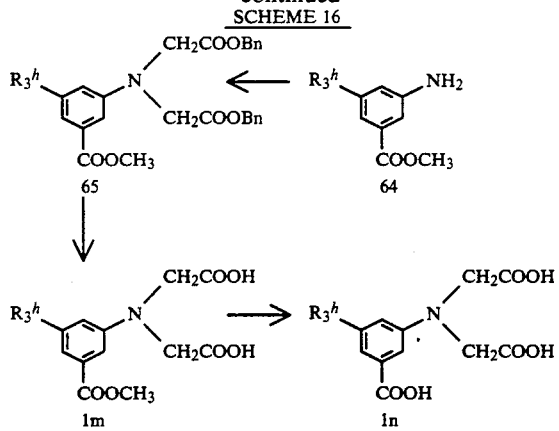

wherein $R_3^h$ and Bn are as previously described.

In Scheme 16, the known compound of formula 62 is alkylated using the corresponding alkyl bromide with potassium carbonate as a base under conditions described in earlier Schemes to give the corresponding compound of formula 63. Catalytic hydrogenolysis of a compound of formula 63 carried out as usual gives the corresponding compound of formula 64 which can be alkylated with excess benzyl bromoacetate as in earlier Schemes to give the corresponding compound of formula 65. Hydrogenolysis of the latter as usual gives the corresponding compound of formula 1m which can be hydrolyzed by heating at reflux with an alkali metal hydroxide in a solvent mixture of water and a lower alkanol to provide the corresponding compound of formula 1n.

The invention also relates to salts of the compounds of formula 1 when they contain an acidic functionality, such as when $R_2$ is hydrogen, which lends itself to salt formation with a base. Salts of the compounds of formula 1 which have a carboxy group are prepared by the reaction with a base having a non-toxic, pharmacologically acceptable cation. In general, any base which will form a salt with a carboxylic acid and whose pharmacological properties will not cause an adverse physiological effect is within the scope of this invention.

Suitable bases thus include, for example, the alkali metal and alkaline earth metal hydroxides, carbonates or the like, for example, calcium hydroxide, sodium hydroxide, sodium carbonate, potassium carbonate or the like, ammonia, primary, secondary and tertiary amines, such as, monoalkylamines, dialkylamines, trialkylamines, for example, methylamine, diethylamine, triethylamine or the like, nitrogen containing heterocyclic amines, for example, piperidine or the like. A salt thus produced is the functional equivalent of the corresponding compound of formula 1 wherein $R_2$ is hydrogen and one skilled in the art will appreciate that the variety of salts embraced by the invention is limited only by the criterion that a base employed in forming the corresponding salts be both non-toxic and physiologically acceptable.

The useful activity of the compounds of formula 1 as phospholipase $A_2$ ($PLA_2$) inhibitors can be demonstrated as hereinafter set forth.

The compounds of formula 1 are potent inhibitors of phospholipases $A_2$ ($PLA_2$'s) and are therefore useful in the treatment of inflammatory diseases, such as psoriasis, inflammatory bowel disease, asthma, allergy, arthritis, dermatitis, gout, pulmonary disease, myocardial ischemia, and trauma induced inflammation, such as spinal cord injury.

Assay for Inhibition of HSF-$PLA_2$ In Vitro

The $PLA_2$ used in this test is the extracellular enzyme obtained from human synovial fluid (HSF-$PLA_2$).

The assay for HSF-$PLA_2$ activity was a modification of the described method [Franson R., Dobrow R., Weiss, J., Elsbach, P., and Weglick W. B., J. Lipid Res., 19, 18–23 (1978)] which was conducted using [1-$^{14}$C]-oleate-labelled $E.$ $coli$ substrate in excess at a final concentration of 20,000 dpm/ml. This was equivalent to 18.2 $\mu$M of cell membrane phospholipid phosphorus and $2 \times 10^9$ autoclaved $E.$ $coli$/ml. The optimal conditions which were developed for the assay of HSF-$PLA_2$ inhibitors are summarized as follows. A total volume of 0.5 ml of reaction mixture typically had the following final composition: substrate (20,000 dpm/ml); enzyme (0.1% HSF, v/v); 2 mM $CaCl_2$; 150 mM $Na^+$; 50 mM sodium HEPES buffer, pH 7.3; and 1% dimethyl sulfoxide (DMSO), used to solubilize test inhibitors) in the presence or absence of inhibitor. The reaction was initiated by the addition of HSF-$PLA_2$ and duplicate samples of the mixture were incubated in $13 \times 100$ mm glass tubes with shaking for 30 minutes at 37° C. The reaction was terminated by the addition of 2.5 ml of chloroform-methanol (1 to 1.5, v/v). The extraction of lipids from the stopped reaction mixture was conducted by the further additions of 0.5 mol of chloroform and 1 ml of water with mixing. After centrifuging, the lower chloroform phase was transferred to smaller glass tubes and the solvent was evaporated to dryness with a nitrogen stream. The extracted lipid residue was redissolved in 50 $\mu$l of a solution containing carrier oleic acid (0.2 mg/ml) of chloroform-methanol [9 to 1, v/v]). The whole lipid extract was applied to a preactivated (30 minutes at 110° C.) silica gel-impregnated glass fiber thin layer chromatography sheet (ITLC type SG sheet from Gelman Sciences, Inc., Ann Arbor, Mich.) using hexane-acetic acid (100 to 1, v/v) as the developing solvent. This TLC system rapidly (6 minutes) resolved the enzymatically released product, $^{14}$C-oleic acid, from the unreacted $^{14}$C-phospholipid substrate. The unsaturated lipids were located on the chromatogram by a brief exposure to iodine vapor. The oleic acid zone ($R_f$ value 0.95) and phospholipid zone (origin) were cut out, chopped into small pieces, shaken with 2 ml of ethanol-water (80 to 20, v/v) and 15 ml of Aquasol and counted for radioactivity. A control incubation of substrate in the absence of HSF-$PLA_2$ was performed in each experiment. The $PLA_2$ activity of the human synovial fluid was corrected for this small control value. In the absence of inhibitors, these optical conditions resulted in approximately 18% hydrolysis of substrate (corrected for a substrate blank of <2%). The specific activity of $PLA_2$ in the pooled human synovial fluid under the optimal assay conditions as 49.2 nmoles [1-$^{14}$C]-oleic acid released hour$^{-1}$ mg$^{-1}$. The $IC_{50}$ ($\mu$M concentration of test compound that produces 50% inhibition of $PLA_2$ activity) was determined for each test compound. The results are reported in Table I.

Phospholipase $A_2$ Rat Paw Edema

Representation compounds of the invention were tested in rats to determine their ability to inhibit the acute inflammatory response induced by the injection of snake venom phospholipase $A_2$. Test compounds are administered intraperitoneally or orally to groups of seven Lewis rats ($\approx$200 gm) 1 hr prior to phospholipase $A_2$ administration. The test compounds are dissolved in dimethyl sulfoxide for intraperitoneal administration and dissolved or suspended in Labrafil M-1944CS for oral administration. At 0 hr, 5 ug (10 units) of purified phospholipase $A_2$ from Naja naja venom (Sigma Chem. Co.) dissolved in 0.1 mL of pyrogen free saline is injected subplantarly into the right hind paw to elicit the inflammatory response. The volume (in mL) of the right hind paw is measured by immersion of the paw to the level of the lateral malleolus in an aqueous plethysmometer immediately prior to the injection of phospholipase $A_2$ and then at 0.5, 2 and 4 hr after phospholipase $A_2$ injection. The paw edema is calculated by subtracting the zero time reading from the readings taken after injection. The percent change of the edema volume from the vehicle treated control is calculated to determine the activity of the test compound. Statistical analysis of the mean paw edema values of the control versus the treated groups is performed using Student's t-test. Significance of changes from mean value for vehicle-treated animals (*$p<0.05$, $p<0.01$, *$p<0.001$, ns/not significant).

Croton Oil Mouse Ear Edema Test

The croton oil-induced mouse ear edema test, a model of irritant-induced contact dermatitis, has also been used for evaluation of the $PLA_2$ inhibitors by the topical route of administration. This test was carried out as described in the following references:

Weirich, E. G., Longauer, J. K. and Kirkwood, A. A. Arch Dermatol. Res. 259: 141-149, 1977.

Tubaro, A., Dri, P., Delbello, G., Zilli, C. and Della Loggia, R. Agents and Actions, 17: 347-349, 1985.

The major active ingredient in croton oil is the tumor promoter 12-O-tetradecanoylphorbol 13-acetate (TPA) and the topical application of TPA to mouse skin has been reported to cause an increase in epidermal $PGE_2$ production as well as an increase in epidermal cell membrane $PLA_2$ activity. Indomethacin, an inhibitor of prostaglandin synthesis, prevented the TPA-mediated increase in epidermal $PGE_2$ levels as well as the TPA-mediated induction of epidermal cell ornithine decarboxylase. Furthermore, the application of $PGE_2$ to mouse skin countered the inhibitory effect of indomethacin upon TPA-stimulated cellular proliferation. Taken together these data suggest that the croton oil mouse ear edema test is a valid model for the topical evaluation of $PLA_2$ inhibitors.

Twenty five µl of a 1% croton oil solution [dissolved in a mixture of pyridine/water/diethyl ether at a ratio of 5/20/75 (croton oil vehicle)] are applied to the outer side of the right ear of 3-4 week old made CD-1 mice (8 animals per group). The test compounds are dissolved directly in the 1% croton oil solution at various concentrations and coapplied. Control animals receive 25 µl of croton oil vehicle on the right ear. Biopsy punches are removed at 6 hours from the right ear of the animals using a 6 mm skin trephine (Roboz, Washington, D.C.) and the wet weight of the ear punches is determined. The weight of the biopsy punches is a measure of ear inflammation, primarily edema. The data are expressed as percent inhibition relative to control groups.

The in vivo activity of representative compounds of formula 1 in the $PLA_2$ rat paw edema and the croton oil ear edema tests are reported in Table I.

TABLE I

| Ex. No. | Name | Inhib of HSF-PLA$_2$ IC$_{50}$ (µM) | % Inhib of PLA$_2$ Rat Paw Edema 2 hr (30 mg/kg ip) | % Inhib of Croton Oil Mouse Ear Edema (1 mg) |
|---|---|---|---|---|
| 6a | N-[3,5-bis(butoxy)phenyl]-N-(carboxymethyl)glycine | 2.0 | 33 ns | NT |
| 6b | N-(carboxymethyl)-N-[3,5-bis(hexyloxy)phenyl]glycine | 2.1 | 25 ns | NT |
| 6c | N-(carboxymethyl)-N-[3,5-bis(octyloxy)phenyl]glycine | 0.4 | +7 ns | 0 |
| 6 | N-(carboxymethyl)-N-[3,5-bis(decyloxy)phenyl]glycine | 0.24 | 45*** | 13* |
| 6d | N-(carboxymethyl)-N-[3,5-bis(dodecyloxy)phenyl]glycine | 0.05 | NT | 21** |
| 6e | N-(carboxymethyl)-N-[3,5-bis(tetradecyloxy)phenyl]glycine | 0.13 | 44*** (50 mg/kg) | NT |
| 6f | N-(carboxymethyl)-N-[3,5-bis(octadecyloxy)phenyl]glycine | 0.5 | NT | NT |
| 6g | N-(carboxymethyl)-N-[3,5-bis(3-phenylpropoxy)phenyl]glycine | 1.3 | 26* | NT |
| 6h | rac-N-(carboxymethyl)-N-[3,5-bis[[2-hydroxydecyl)oxy]phenyl]glycine | 0.5 | 5 ns | NT |
| 6i | N-(carboxymethyl)-N-[3,5-bis[(5-hydroxy-5-oxopentyl)oxy]phenyl]glycine | 6% (20 µM) | NT | NT |
| 6j | N-(carboxymethyl)-N-[3,5-bis[(11-methoxy-11-oxoundecyl)oxy]phenyl]glycine | 0.3 | 0 | 66*** |
| 6k | N-(carboxymethyl)-N-[3,5-bis[(11-hydroxy-11-oxoundecyl)oxy]phenyl]glycine | 35% (10 µM) | 0 | 16 ns |
| 6l | N-[3,5-bis[3-(1,1'-biphenyl-2-yloxy)propoxy] N-(carboxymethyl)glycine | 0.42 | 0 | 30** |
| 6m | N-[3,5-bis[3-(1,1'-biphenyl-3-yloxy)propoxy] N-(carboxymethyl)glycine | 0.58 | NT | NT |
| 6n | N-[3,5-bis[3-(1,1'-biphenyl-4-yloxy)propoxy] N-(carboxymethyl)glycine | 0.40 | NT | NT |
| 6o | N-(carboxymethyl)-N-[3,5-bis[2-[2-naphthalenyloxy)]ethoxy]glycine | 0.6 | NT | NT |
| 6p | N-(carboxymethyl)-N-[3,5-bis[2-[1-naphthalenyloxy)]ethoxy]glycine | 2.0 | NT | NT |
| 16 | N-(carboxymethyl)-N-[3,5-bis[(decyl-amino)carbonyl]phenyl]glycine | 0.3 | 0 | 10 ns |
| 6q | N-(carboxymethyl)-N-[3,5-bis[(tetradecyl-amino)carbonyl]phenyl]glycine | 0.3 | 0 | NT |
| 6r | N-(carboxymethyl)-N-[3,5-bis[(octadecyl-amino)carbonyl]phenyl]glycine | 0.64 | NT | NT |
| 6s | N-(carboxymethyl)-N-[3,5-bis[(tricyclo[3.3.1.1/3,7/]phenyl]glycine | 30% (10 µM) | NT | NT |
| 21 | N-(carboxymethyl)-N-[[3,5-bis[(1-oxo decyl)amino]phenyl]glycine | 3.8 | NT | NT |
| 29 | N-(carboxymethyl)-N-(3,5-didecyl-phenyl)glycine | 1.5 | NT | NT |
| 6t | N-(carboxymethyl)-N-(3,5-dinonadecyl-phenyl)glycine | 39% (10 µM) | NT | NT |
| 6u | N-(carboxymethyl)-N-[3,5-bis[(1-oxodecyl)oxy]phenyl]glycine | 64% (1 µM) | NT | NT |
| 25 | N-(carboxymethyl)-N-[3,5-bis[(tetradecyl-oxy)carbonyl]phenyl]glycine | 48% (1 µM) | 17 ns | 62*** |
| 6v | N-(carboxymethyl)-N-[3,5-bis[(decyl-oxy)carbonyl]phenyl]glycine | 73% (1 µM) | 9 ns | 80*** |
| 119a | N-(carboxymethyl)-N-[3,4-bis(decyloxy)phenyl]glycine | 0.16 | NT | NT |
| 119 | N-(carboxymethyl)-N-[3,4-bis(tetradecyloxy)phenyl]glycine | 36% (1 µM) | 16 ns | 49*** |
| 123 | N-(carboxymethyl)-N-[3,4-bis[(1-oxodecyl)oxy]phenyl]glycine | 0.48 | 4 ns | 58*** |

TABLE I-continued

| Ex. No. | Name | Inhib of HSF-PLA$_2$ IC$_{50}$ ($\mu$M) | % Inhib of PLA$_2$ Rat Paw Edema 2 hr (30 mg/kg ip) | % Inhib of Croton Oil Mouse Ear Edema (1 mg) |
|---|---|---|---|---|
| 119b | N-(carboxymethyl)-N-[3,4-bis[(1-oxotetradecyl)oxy]phenyl]glycine | 80% (1 $\mu$M) | NT | 75*** |
| 119d | N-(carboxymethyl)-N-[3,4-bis[[(octadecylamino)carbonyl]oxy]phenyl]glycine | 19% (1 $\mu$M) | NT | 14 ns |
| 119e | N-(carboxymethyl)-N-[3,4-bis[[(tetradecylamino)carbonyl]oxy]phenyl]glycine | 33% (1 $\mu$M) | NT | 0 |
| 36a | N-(carboxymethyl)-N-[3-(decyloxy)phenyl]glycine | 2.9 | 35 | NT |
| 36 | N-(carboxymethyl)-N-[3-(octadecyloxy)phenyl]glycine | 0.17 | NT | 21** |
| 36b | N-(carboxymethyl)-N-3-[(1-oxooctadecyl)oxy]phenyl]glycine | 0.2 | 0 | 61*** |
| 36c | N-(carboxymethyl)-N-[3-[[(heptadecylamino)carbonyl]oxy]phenyl]glycine | 1.0 | 0 | 0 |
| 36d | N-(carboxymethyl)-N-[[(decylamino)carbonyl]phenyl]glycine | 46% (10 $\mu$M) | NT | NT |
| 42 | N-(carboxymethyl)-N-[3-[(octadecylamino)carbonyl]phenyl]glycine | 0.4 | 38** | 0 |
| 174 | N-(carboxymethyl)-N-[3-[(di-decylaminocarbonyl)(phenyl]glycine | 74% (5 $\mu$M) | 46** | 29* |
| 46 | N-(carboxymethyl)-N-3-[(1-oxooctadecyl)amino]phenyl]glycine | 84% | 44* | 35* |
| 36e | N-(carboxymethyl)-N-[3-[[(octadecylamino)carbonyl]amino]phenyl]glycine | 74% (5 $\mu$M) | 30* | 31* |
| 49 | N-(carboxymethyl)-N-[3-[(Z)-(9-octadecenyl)oxy]phenyl]glycine | 0.3 | NT | NT |
| 49 | N-(carboxymethyl)-N-[3-[(9Z,12Z)-(9,12-octadecadienyl)oxy]phenyl]glycine | 0.2 | NT | NT |
| 51 | N-(carboxymethyl)-N-[3-[(Z)-(1-oxo-9-octadecenyl)amino]phenyl]glycine | 63% (5 $\mu$M) | NT | NT |
| 51 | N-(carboxymethyl)-N-[3-[(9Z, 12Z)-(1-oxo-9,12-octadecadienyl)amino]phenyl]glycine | 67% (5 $\mu$M) | NT | NT |
| 36f | N-(carboxymethyl)-N-(3-nonadecyl phenyl)glycine | 0.2 | NT | NT |
| 36g | N-(carboxymethyl)-N-[(3-(2-naphthalenyloxy)ethoxy]phenyl]glycine | 19% (10 $\mu$M) | NT | NT |
| 36h | N-(carboxymethyl)-N-[3-[(tricyclo[3.3.1.1/3,7/]dec-1-ylamino)carbonyl]phenyl]glycine | 25% (20 $\mu$M) | NT | NT |
| 36i | N-(carboxymethyl)-N-[3-{3-(3-pentadecylphenoxy)propoxy]phenyl]glycine | 0.4 | 7 ns | NT |
| 39a | N-(carboxymethyl)-N-phenylglycine | −10% (20 $\mu$M) | NT | NT |
| 39b | N-(carboxymethyl)-N-(4-butyl-phenyl)glycine | 264 | −9 ns | NT |
| 39c | N-(carboxymethyl)-N-(4-octyl-phenyl)glycine | 1.7 | NT | NT |
| 39d | N-(carboxymethyl)-N-(4-decyl-phenyl)glycine | 39% (1 $\mu$M) | NT | NT |
| 39 | N-(carboxymethyl)-N-(4-tetradecylphenyl)glycine | 67% (1 $\mu$M) | NT | NT |
| 80 | N-[3-acetyloxy-5-(octadecyloxy)phenyl]-N-(carboxymethyl)glycine | 0.22 | NT | NT |
| 81 | N-(carboxymethyl)-N-[3-hydroxy-5-(octadecyloxy)phenyl]glycine | 0.23 | 44*** (10 mg/kg) | 69*** |
| 58a | N-(carboxymethyl)-N-[3-(2-hydroxyethoxy)-5-(octadecyloxy)phenyl]glycine | 0.2 | 29 ns | 0 |
| 58b | N-(carboxymethyl)-N-[3-(2-methoxy-2-oxoethoxy)-5-(octadecyloxy)phenyl]glycine | 91% (5 $\mu$M) | 20* | 19* |
| 58c | N-[3-(carboxymethoxy)-5-(octadecyloxy)phenyl]-N-(carboxymethyl)glycine | 2.8 | 39*** | 0 |
| 64 | N-(carboxymethyl)-N-[3-(octadecyloxy)-5-[(5-methoxy-5-oxopentyl)oxy]phenyl]glycine | 0.06 | 61** | 87*** |
| 65 | N-[3-(4-carboxybutoxy)-5-(octadecyloxy)phenyl]-N-(carboxymethyl)glycine | 0.86 | 35* | 91*** |
| 58d | N-(carboxymethyl)-N-[3-(11-methoxy-11-oxoundecyloxy)-5-(octadecyloxy)phenyl]glycine | 0.08 | NT | NT |
| 58e | N-(carboxymethyl)-N-[[3-(11-hydroxy-11-oxoundecyloxy)phenyl]glycine | 0.2 | NT | NT |
| 58f | N-(Carboxymethyl)-N-[[3-(octadecyloxy)-5-(tricyclo-[3.3.1.1/3,7]dec-1-ylcarbonyl)oxy]phenyl]glycine | 0.3 | NT | NT |
| 58g | N-(carboxymethyl)-N-3-(octadecyloxy)-5-(2,2-diphenyl-1-oxoethoxy)phenyl]glycine | 0.1 | NT | NT |
| 58h | N-(carboxymethyl)-N-[3-[2-(2-naphthalenyloxy)ethoxy]-5-(octadecyloxy)phenyl]glycine | 0.05 | 31 ns | 3 ns |
| 58i | N-(carboxymethyl)-N-3-(octadecyloxy)-5-[3-(3-pyridinyloxy)propoxy]phenyl]glycine | 0.3 | NT | NT |
| 58 | N-(carboxymethyl)-N-3-(octadecyloxy)-5-(3-phenoxy)phenyl]glycine | 0.06 | 36* | 78*** |

TABLE I-continued

| Ex. No. | Name | Inhib of HSF-PLA$_2$ IC$_{50}$ (μM) | % Inhib of PLA$_2$ Rat Paw Edema 2 hr (30 mg/kg ip) | % Inhib of Croton Oil Mouse Ear Edema (1 mg) |
|---|---|---|---|---|
| 58j | N-(carboxymethyl)-N-[3-[3-(3-methoxyphenoxy)propoxy]-5-(octadecyloxy)phenyl]glycine | 0.06 | 57** | 28* |
| 58k | N-(carboxymethyl)-N-[3-[3-(4-methoxyphenoxy)propoxy]-5-(octadecyloxy)phenyl]glycine | 0.05 | 0 | 85*** |
| 58l | N-(carboxymethyl)-N-[3-[3-(4-hydroxyphenoxy)propoxy]-5-(octadecyloxy)phenyl]glycine | 81% (1 μM) | 53** | 76*** |
| 58m | N-(carboxymethyl)-N-[3-[3-(3-nitrophenoxy)propoxy]-5-(octadecyloxy)phenyl]glycine | 79% (1 μM) | 52** | 60*** |
| 58n | N-(carboxymethyl)-N-[3-[3-(3-aminophenoxy)propoxy]-5-(octadecyloxy)phenyl]glycine | 0.13 | 4** | 64*** |
| 58o | N-(carboxymethyl)-N-[3-[3-[4-(methoxycarbonyl)phenoxy)propoxy]-5-(octadecyloxy)phenyl]glycine | 0.1 | 0 | 30* |
| 58p | N-(carboxymethyl)-N-[3-[3-[4-(carboxyphenoxy)propoxy]-5-(octadecyloxy)phenyl]glycine | 0.6 | NT | 0 |
| 108 | N-[3-[3-(3-bromophenoxy)propoxy]-5-(octadecyloxy)phenyl]-N-(carboxymethyl)glycine | 92% (1 μM) | 12 ns | 34* |
| 177 | N-(carboxymethyl)-N-[3-[3-[4-(1,1-dimethylethyl)phenoxy]propoxy]-5-(octadecyloxy)phenyl]glycine | 95% (1 μM) | 41** | 22 ns |
| 146 | N-(carboxymethyl)-N-[3-[5-(2,3-dihydroxyphenyl)pentoxy]-5-(octadecyloxy)phenyl]glycine | 0.2 | 74** | 18 ns |
| 88 | N-(carboxymethyl)-N-[3-[3-(diethoxyphosphinyl)propoxy]-5-(octadecyloxy)phenyl]glycine | 0.4 | 46** | 43** |
| 89 | N-(carboxymethyl)-N-[3-[3-(ethoxyphosphinyl)propoxy]-5-(octadecyloxy)phenyl]glycine | 31% (1 μM) | 45** | NT |
| 151 | N-(carboxymethyl)-N-[3-[2-[2-(2-ethoxyethoxy)ethoxy]ethoxy]-5-(octadecyloxy)phenyl]glycine | 100% (1 μM) | 43* | 54*** |
| 148 | N-(carboxymethyl)-N-[(3-(octadecyloxy)-5-[(2-quinolinyl)methoxy]phenyl]glycine | 91% (1 μM) | 37* | 26* |
| 154 | N-(carboxymethyl)-N-[3-[4-(2,3-dihydroxy-6-naphthalenylbutoxy]-5-(octadecyloxy)phenyl]glycine | 96% (1 μM) | 78** | NT |
| 156 | N-(carboxymethyl)-N-[3-[2-[2-[2-(2-methoxyethoxy)ethoxy]ethoxy]ethoxy]-5-(octadecyloxy)phenyl]glycine | 100% (1 μM) | 29** | NT |
| 159 | N-(carboxymethyl)-N-[3-[3-[4-(methylsulfinyl phenoxy]propoxy]-5-(octadecyloxy)phenyl]glycine | 100% (1 μM) | 78** | 59*** |
| 161 | N-(carboxymethyl)-N-[3-[3-[4-(methylsulfonyl phenoxy]propoxy]-5-(octadecyloxy)phenyl]glycine | 100% (1 μM) | 66** | 87*** |
| 69 | N-(carboxymethyl)-N-[3-(methoxycarbonyl)-5-(octadecyloxy)phenyl]glycine | 0.1 | 57** | 22 ns |
| 70 | N-[3-carboxy-5-(octadecyloxy)phenyl]-N-(carboxymethyl)glycine | 1.0 | 45** | 0 |
| 75 | N-(carboxymethyl)-N-[(3-carbamoyl)-5-(octadecyloxy)phenyl]glycine | 84% (5 μM) | 33* | 15 ns |
| 93 | N-(carboxymethyl)-N-[3-nitro-5-(octadecyloxy)phenyl]glycine | 56% (1 μM) | 20 ns | 0 |
| 94 | N-(carboxymethyl)-N-[3-amino-5-(octadecyloxy)phenyl]glycine | 0.42 | 28 ns | 10 ns |
| 98 | N-[3-(acetylamino)-5-(octadecyloxy)phenyl]-N-(carboxymethyl)glycine | 98% (1 μM) | 51** | NT |
| 69a | N-(carboxymethyl)-N-[(3-methoxycarbonyl)-5-(tetradecyloxy)phenyl]glycine | 52% (1 μM) | 12 ns | 71*** |
| 69b | N-[3-carboxy-5-(tetradecyloxy)pyhenyl]-N-(carboxymethyl)glycine | 18% (1 μM) | +4 ns | 72*** |
| 69c | N-(carboxymethyl)-N-[(3-methoxycarbonyl)-5-(decyloxy)phenyl]glycine | 22% | 1 ns | 78*** |
| 69d | N-[3-carboxy-5-(decyloxy)phenyl]-N-(carboxymethyl)glycine | 7% (1 μM) | 0 | 63** |
| 162 | N-(carboxymethyl)-N-[3-(octadecyloxy)-5-[[trifluoromethyl)sulfonyl]amino]phenyl]glycine | 82% (1 μM) | 65** | 79*** |
| 166 | N-(carboxymethyl)-N-[3-(methylthio)-5-octadecyloxy)phenyl]glycine | 88% (1 μM) | 31* | NT |
| 172 | N-(carboxymethyl)-N-[3-(methylsulfinyl)-5-octadecyloxy)phenyl]glycine | 39% (1 μM) | 43** | NT |
| 168 | [[3-[bis(carboxymethyl)amino]-5-(octadecyloxy)phenyl]sulfinyl]acetic acid | 26% (1 μM) | 45** | 83*** |
| 12 | N-[[3,5-bis[(decylamino)carbonyl]phenyl]glycine | 5.2 | 34** | 70*** |
| 127 d | rac-N-[[3,5-bis[(2-hydroxydecyl)oxy]phenyl]glycine | 3.5 | NT | NT |
| 127c | N-[3,5-bis(tetradecyloxy)phenyl]glycine | 73% (10 μM) | NT | NT |
| 125 | N-[3-(octadecyloxy)phenyl]glycine | 55% (10 μM) | NT | 75*** |
| 175 | N-[[3-(octadecyloxy)-5-(tricyclo[3.3.1.1/3,7/dec-1-ylcarbonyl)oxy]phenyl]glycine | 0.3 | NT | NT |
| 30 | 4-[3,5-bis(decyloxy)phenyl]2,6-morpholinedione | 0.47 | 91 ns | 63*** |
| 31 | N-(2-methoxy-2-oxoethyl)-N-[3,5-bis(decyloxy)phenyl]glycine | 9% | 21 ns | 50*** |
| 32 | N-(carbamoylmethyl)-N-[3,5-bis(decyloxy)phenyl]glycine ammoniuim salt | 48% (1 μM) | 23 ns | 54*** |
| 33 | N-(2-diethylaminoethoxy-2-oxoethyl)-N-[3,5-bis | −5% | 15 ns | 25* |

TABLE I-continued

| Ex. No. | Name | Inhib of HSF-PLA$_2$ IC$_{50}$ ($\mu$M) | % Inhib of PLA$_2$ Rat Paw Edema 2 hr (30 mg/kg ip) | % Inhib of Croton Oil Mouse Ear Edema (1 mg) |
|---|---|---|---|---|
| | (decyloxy)phenyl]glycine monohydrochloride salt | (1 $\mu$M) | | |
| 132 | N-2-[(acetyloxy)methoxy]-2-oxoethyl]-N-[3,5-bis(decyloxy)phenyl]glycine(acetyloxy)methyl ester | NT | NT | 36* |
| 131 | N-[3,5-bis(decyloxy)phenyl]-N-[2-[[bis(2-hydroxyethyl)amino]carbonyl]methoxy]-2-oxoethyl]glycine [[bis(2-hdyroxyethyl)amino]carbonyl]methyl ester | NT | +18 ns | 47*** |
| 130 | N-[3,5-bis(decyloxy)phenyl]-N-[2-(2-diethylamino)ethoxy]-2-oxoethyl]glycine 2-(diethylamino)ethylester hydrochloride | NT | +2 ns | NT |

ASSAY FOR INHIBITION OF SNAKE VENOM PLA$_2$ (SV-PLA$_2$) IN VITRO

Several representative compounds of the invention were also tested as inhibitors of Naja naja snake venom PLA$_2$ (SV-PLA$_2$). The assay employed in this study was the spectrophotometric method described by: C. Vigo, G. P. Lewis and P. J. Piper in Biochemical Pharmacology, 29:623–627 (1983), which was modified as described by: A. F. Welton, L. D. Tobias, C. Fiedler-Nagy, W. Anderson, W. Hope, K. Meyers and J. W. Coffey in "Plant Flavonoids in Biology and Medicine: Biochemical, Pharmacological and Structure-Activity Relationships", p 231–242, (1986) Alan R. Liss, Inc. The PLA$_2$ paw edema model, (data in Table I) is initiated by injection of SV-PLA$_2$. The results obtained are set forth in Table II.

TABLE II

| Ex. No. | Name | Inhib of SV-PLA$_2$ IC$_{50}$ ($\mu$M) |
|---|---|---|
| 6c | N-(Carboxymethyl)-N-[3,5-bis(octyloxy)phenylglycine | 0.022 |
| 6 | N-(carboxymethyl)-N-[3,5-bis(decyloxy)phenylglycine | 0.017 |
| 6d | N-(carboxymethyl)-N-[3,5-bis(dodecyloxy)phenylglycine | 0.17 |
| 39c | N-(carboxymethyl)-N-(4-octylphenyl)glycine | 0.066 |
| 16 | N-(carboxymethyl)-N-[3,5-bis(decylamino)carbonyl]phenyl]glycine | 0.05 |

Rat Carrageenan Paw Edema

Representative compounds of the invention were tested in rat carrageenan-induced paw edema to determine their ability to inhibit this acute inflammatory response. Test compounds are administered intraperitoneally or orally to groups of seven Lewis rats ($\approx$200 gm) 1 hr prior to carrageenan administration. The test compounds are dissolved in dimethyl sulfoxide for intraperitoneal administration and dissolved or suspended in Labrafil M-19944CS for oral administration. At 0 hour, 0.1 mL of 1% carrageenan dissolved in pyrogen free saline is injected subplantarly into the right hind paw to elicit the inflammatory response. The volume (in mL) of the right hind paw is measured by immersion of the paw to the level of the lateral malleolus in an aqueous plethysmometer immediately prior to the injection of carrageenan and then at 1, 2 and 4 hr after carrageenan injection. The paw edema is calculated by substracting the zero time reading from the readings taken after injection. The percent change of the edema volume from the vehicle treated control is calculated to determine the activity of the test compound. Statistical analysis of the mean paw edema values of the control versus the treated groups are performed using Student's t-test.

The results obtained are set forth in Table III.

TABLE III

RAT CARRAGEENAN PAW TEST

| Ex. No. | Name | Dose mg/kg ip | % Inhibition at 2 hours |
|---|---|---|---|
| 36a | N-(carboxymethyl)-N-[3-(decyloxy)phenyl]glycine | 30 | 47*** |
| 64 | N-(carboxymethyl)-N-[3-(octadecyloxy)-5-[(5-methoxy-5-oxopentyl)oxy]phenyl]glycine | 30 | 69** |
| 88 | N-(carboxymethyl)-N-[3-[3-(diethoxyphosphinyl)propoxy]-5-(octadecyloxy)phenyl]glycine | 30 | 57** |
| 58 | N-(carboxymethyl)-N-[3-(octadecyloxy)-5-(3-phenoxypropoxy)phenyl]glycine | 30 | 29** |
| 58m | N-(carboxymethyl)-N-[3-[3-(3-nitrophenoxy)propoxy-5-(octadecyloxy)phenyl]glycine | 10 | 61** |
| 58n | N-(carboxymethyl)-N-[3-[3-(3-aminophenoxy)propoxy-5-(octadecyloxy)phenyl]glycine | 30 | 65** |
| 108 | N-[3-[3-(3-bromophenoxy)propoxy]-5-(octadecyloxy)phenyl]-N-(carboxymethylglycine | 30 | 33** |
| 177 | N-(carboxymethyl)-N-[3-[3-4-(1,1-dimethylethyl)phenoxy]propoxy]-5-(octadecyloxy)phenyl]glycine | 30 | 57** |
| 146 | N-(carboxymethyl)-N-3-[5-(2,3-dihydroxyphenyl)pentoxy]-5-(octadecyloxy)phenyl]glycine | 30 | 55** |
| 154 | N-(carboxymethyl)-N-[3-[4-(2,3-dihydroxy-6-naphthalenyl)butoxy]-5-(octadecyloxy)phenyl]glycine | 30 | 70** |
| 159 | N-(carboxymethyl)-N-[3-[3-[4-(methylsulfinyl)phenoxy]propoxy]-5-(octadecyloxy)phenyl]glycine | 30 | 44** |

TABLE III-continued

RAT CARRAGEENAN PAW TEST

| Ex. No. | Name | Dose mg/kg ip | % Inhibition at 2 hours |
|---|---|---|---|
| 161 | N-(carboxymethyl)-N-[3-[3-[4-(methylsulfonyl)phenoxy]propoxy]-5-(octadecyloxy)phenyl]glycine | 30 | 56** |
| 162 | N-(carboxymethyl)-N-[3-(octadecyloxy)-5-[[(trifluoromethyl)sulfonyl]amino]phenyl]glycine | 30 | 69** |

Established Adjuvant Arthritis Test

Representative compounds of the invention were tested in the standard adjuvant arthritis model in rats, induced by Freunds complete adjuvant, as described by C. E. Brinckerhoff, J. W. Coffey and A. C. Sullivan, Science, 221, p. 756–758 (1983). The results obtained are set forth in Table IV.

mizer or similar device and myeloperoxidase was measured in the homogenate using o-phenylenediamine as a cromagen, as described by A. Voller, D. E. Bidwell and A. Bartlett in "The Enzyme Linked Immunosorbent Assay (ELISA)", Zoological Soc., London, 1979, pages 29–30. Control animals were pretreated with the vehicle and saline in place of acetic acid.

TABLE IV

ESTABLISHED ADJUVANT ARTHRITIS TEST

| Ex. No | Name | Dose mg/kg ip | Change in Paw Volume (mL) | |
|---|---|---|---|---|
| | | | Treated | Control |
| 6 | N-(carboxymethyl)-N-[3,5-bis(decyloxy)phenyl]glycine | 30 | −0.04 ± 0.24** | 0.96 |
| 58 | N-(carboxymethyl)-N-[3-(octadecyloxy)-5-(3-(phenoxypropoxy)phenyl]glycine | 10 | 0.37 ± 0.14 | 0.60 |
| 58m | N-(carboxymethyl)-N-[3-[3-(3-nitrophenoxy)propoxy-5-(octadecyloxy)phenyl]glycine | 10 | 0.40 ± 0.13* | 0.96 |
| 58n | N-(carboxymethyl)-N-[3-[3-(3-aminophenoxy)propoxy-5-(octadecyloxy)phenyl]glycine | 10 | 0.23 ± 0.12** | 0.96 |
| 88 | N-(carboxymethyl)-N-[3-[3-(diethoxyphosphinyl)propoxy]-5-(octadecyloxy)phenyl]glycine | 30 | −0.90 ± 0.11** | −0.28 |
| 89 | N-(carboxymethyl)-N-[3-[3-(ethoxyphosphinyl)propoxy]-5-(octadecyloxy)phenyl]glycine | 30 | −0.68 ± 0.08 | −0.28 |
| 70 | N-[3-carboxy-5-(octadecyloxy)phenyl]-N-(carboxymethyl)glycine | 10 | 0.30 ± 0.09** | 0.84 |
| 64 | N-(carboxymethyl)-N-[3-(octadecyloxy)-5-[(5-methoxy-5-oxopentyl)oxy]phenyl]glycine | 10 | 0.65 ± 0.12 | 0.95 |
| 151 | N-(carboxymethyl)-N-[3-[2-[2-(2-ethoxyethoxy)ethoxy]ethoxy]-5-(octadecyloxy)phenyl]glycine | 10 | 0.28 ± 0.16* | 0.85 |

Acetic Acid-Induced Colitis in Rats

The rat acetic acid-induced colitis bioassay has been described by J. E. Krawisz, et al. in Amer. J. Proc. Gastro. Col. Rec. Surg. 31: 11–18 (1980), and by P. Sharon and W. F. Stenson in Gastroenterology 88: 55–63 (1985) and 86:453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water, or dimethylsulfoxide) or the test inhibitor compound suspended in water or dissolved in dimethylsulfoxide and orally administrated. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. Then 24 hours after the acetic acid treatment, the animals were sacrificed. The colonic mucosa was surgically removed and homogenized in an aqueous buffer at pH 6 with a Tissu- Data for representative compounds of this invention is reported in Table V.

TABLE V

RAT ACETIC ACID COLITIS TEST

| Ex. No. | Name | % Inhibition of Myeloperoxidase Accumulation at 10 mg/kg po |
|---|---|---|
| 16 | N-(carboxymethyl)-N-[3,5-bis[(decylamino)carbonyl]phenyl]glycine | 212 ± 124 |
| 36 | N-(carboxymethyl)-N-[3-(octadecyloxy)phenyl]glycine | 190 ± 76 |
| 6e | N-(carboxymethyl)-N-[3,5-bis(tetradecyloxy)phenyl]glycine | 145 ± 72 |

In practice of the invention, the dose of a compound of formula 1 or a salt thereof to be administered and the frequency of administration will be dependent on the potency and duration of activity of the particular compound of formula 1 or salt to be administered and on the route of administration, as well as the severity and nature of the condition and age of the mammal to be treated and the like. Oral doses of a compound of formula 1 or a salt thereof contemplated for use in practicing the invention can be in the range of from 10 mg to about 2.0 g per day, preferably about 50 mg to about 1 gm per day, either as a single dose or in divided doses.

A compound of formula 1, or a salt of a composition containing a therapeutically effective amount of a compound of formula 1, (an enantiometer of a racemate, where applicable) or a salt thereof can be administered by methods well known in the art. Thus, a compound of formula 1, or a salt thereof can be administered either singly or with other pharmaceutical agents, for example, antihistamines, mediator release inhibitors, methyl xanthines, beta agonists or antiasthmatic steroids such as prednisone and prednisolone, orally, parenterally, rectally, or by inhalation, for example in the form of an aerosol, micropulverized powder or nebulized solution. For oral administration, they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered as solutions or suspension, for example, as an aqueous or peanut oil or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in pressurized container fitted with an aerosol valve suitable for release of the pressurized composition. Preferably, the aerosol valve is a metered valve, that is one which on activation releases a predetermined effective dose of the aerosol composition.

EXPERIMENTAL SECTION

The Examples which follow further illustrate the invention. All temperatures set forth in the specification and the Examples are in degrees Centigrade. Melting points were taken on a Thomas Hoover capillary melting point apparatus and are uncorrected. All compounds were characterized by proton magnetic resonance spectra taken on a Varian XL-200 or XL-400 spectrometer and electron impact or fast atom bombardment (+FAB) mass spectra taken on either VG ZAB-1F or VG 70E-HF mass spectrometers. Preparative high-pressure liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

3,5-Bis(decyloxy)benzoic acid methyl ester

A mixture of 25.0 g (0.149 mol) of methyl 3,5-dihydroxy benzoate, 68 ml (0.327 mol) of 1-bromodecane and 41 g (0.298 mol) of anhydrous potassium carbonate in 500 ml of anhydrous DMF was stirred and heated at 75° for 23 hours. The reaction mixture was filtered and the filtrate was concentrated under reduced pressure (oil pump) at 60°. The residue was stirred with 650 ml of 0.5N HCl for 2 hours and the crude product was removed by filtration. Recrystallization from methanol gave 40.5 g (61% yield, mp 52°–53°) of 3,5-bis(decyloxy)benzoic acid methyl ester.

Anal. Calcd for $C_{28}H_{48}O_4$: C, 74.95; H, 10.78. Found: C, 75.11; H, 10.99.

Following the procedure of Example 1 and using 3,5-dihydroxybenzoic acid methyl(or phenylmethyl ester) and the appropriate alkyl bromide or epoxide the compounds in Table 1 were prepared. Following the procedure of Example 1 using 2,3-, 3,4-, 2,4-, and 2,5-dihydroxy benzoic acid methyl esters and the appropriate alkyl bromide the compounds in Table 1A were prepared.

TABLE 1

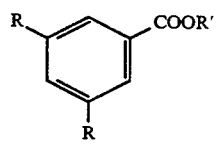

|  |  |  |  |  | Calcd | | Found | |
|---|---|---|---|---|---|---|---|---|
| Ex. | R | R' | mp (°C.) | E.F. | C | H | C | H |
| 1a | $OC_4H_9$ | $CH_3$ | liquid | $C_{16}H_{24}O_4$ | | | *N.O. | |
| 1b | $OC_6H_{13}$ | $CH_3$ | liquid | $C_{20}H_{32}O_4$ | | | N.O. | |
| 1c | $OC_8H_{17}$ | $CH_3$ | 38–40 | $C_{24}H_{40}O_4$ | | | N.O. | |
| 1d | $OC_{12}H_{25}$ | $CH_3$ | 59–61 | $C_{23}H_{56}O_4$ | | | N.O. | |
| 1e | $OC_{14}H_{29}$ | $CH_3$ | 67–69 | $C_{36}H_{64}O_4$ | | | N.O. | |
| 1f | $OC_{18}H_{37}$ | $CH_3$ | 78–80 | $C_{44}H_{80}O_4$ | 78.51 | 11.98 | 78.42 | 11.81 |
| 1g | $O(CH_2)_3C_6H_5$ | $CH_3$ | liquid | $C_{26}H_{28}O_4$ | | | N.O. | |
| 1h | $OCH_2CHOHC_8H_{17}$ | $CH_3$ | 60–62 | $C_{28}H_{48}O_6$ | 69.96 | 10.07 | 70.25 | 10.05 |
| 1i | $OCH_2CHOHC_{10}H_{21}$ | $CH_3$ | 66–68 | $C_{32}H_{56}O_6$ | 71.60 | 10.52 | 71.76 | 10.49 |
| 1j | $O(CH_2)_4COOCH_3$ | Bz | liquid | $C_{26}H_{32}O_8$ | | | N.O. | |
| 1k | $O(CH_2)_{10}COOCH_3$ | $CH_3$ | 76–77 | $C_{32}H_{52}O_8$ | 68.06 | 9.28 | 67.67 | 9.52 |
| 1m | $O(CH_2)_3OC_6H_4$-2-$C_6H_5$ | $CH_3$ | 77–79 | $C_{38}H_{36}O_6$ | | | N.O. | |
| 1n | $O(CH_2)_3OC_6H_4$-3-$C_6H_5$ | $CH_3$ | liquid | $C_{38}H_{36}O_6$ | | N.O. | | |
| 1o | $O(CH_2)_3OC_6H_4$-4-$C_6H_5$ | $CH_3$ | 145 | $C_{38}H_{36}O_6$ | 77.53 | 6.16 | 77.48 | 5.83 |
| 1p | $O(CH_2)_2O$-2-Naphthyl | $CH_3$ | 132–137 | $C_{32}H_{28}O_6$ | 75.58 | 5.55 | 75.19 | 5.44 |
| 1q | $O(CH_2)_2O$-1-Naphthyl | $CH_3$ | 116–118 | $C_{32}H_{28}O_6$ | | | | N.O. |

*Not Obtained

TABLE 1A

| Structure | Ex. | R | mp (°C.) | E.F. | Calcd C | Calcd H | Calcd N | Found C | Found H | Found N |
|---|---|---|---|---|---|---|---|---|---|---|
| R—[benzene]—COOCH3 (with R ortho and meta) | 1r | OC10H21 | oil | C28H48O4 | 74.95 | 10.78 | | 74.77 | 10.46 | |
| | 1s | OC14H29 | oil | C36H64O4 | | | | N.O.* | | |
| R—[benzene]—COOCH3 (3,4-disub) | 1t | OC10H21 | 40–41 | C28H48O4 | 74.95 | 10.78 | | 74.78 | 10.63 | |
| | 1u | OC14H29 | 49–50 | C36H64O4 | 77.09 | 11.50 | | 76.98 | 11.34 | |
| R—[benzene]—COOCH3 (2,4-disub) | 1v | OC10H21 | oil | C28H48O4 | | | | N.O. | | |
| | 1w | OC14H29 | 33–34 | C36H64O4 | | | | N.O. | | |
| R—[benzene]—COOCH3 (other isomer) | 1x | OC10H21 | oil | C28H48O4 | | | | N.O. | | |
| | 1y | OC14H29 | oil | C36H64O4 | | | | N.O. | | |

*Not Obtained

EXAMPLE 2

3,5-Bis(decyloxy)benzoic acid

A solution of 6.0 g (0.013 mol) of 3,5-bis(decyloxy)benzoic acid methyl ester in 300 ml of methanol and 40 ml of 1N sodium hydroxide was stirred at reflux for 3.5 hours. The reaction mixture was concentrated under reduced pressure and the residue was acidified with 6N HCl. The product was extracted with ethyl acetate and the dried extract was concentrated under reduced pressure to a yellow solid. Recrystallization from methanol-water gave 5.45 g (95% yield, mp 56°–58°) of 3,5-bis(decyloxy)benzoic acid.

Anal. Calcd for $C_{27}H_{46}O_4$: C, 74.61; H, 10.67. Found: C, 74.92; H, 10.83.

The compounds in Tables 2 and 2A were prepared from the ester precursors in Tables 1 and 1A, respectively, using the procedure of Example 2.

TABLE 2

R—[3,5-disubstituted benzene]—COOH

| Ex. | R | mp (°C.) | E.F. | Calcd C | Calcd H | Found C | Found H |
|---|---|---|---|---|---|---|---|
| 2a | OC4H9 | 78–79 | C15H22O4 | 67.75 | 8.33 | 67.57 | 8.29 |
| 2b | OC6H13 | 55–57 | C19H39O4 | 70.77 | 9.38 | 70.73 | 9.71 |
| 2c | OC8H17 | 54–55 | C23H38O4 | 72.98 | 10.12 | 72.93 | 10.04 |
| 2d | OC12H25 | 62–63 | C31H54O4 | 75.87 | 11.09 | 75.80 | 11.04 |
| 2e | OC14H29 | 62–64 | C35H62O4 | 76.87 | 11.43 | 77.15 | 11.71 |
| 2f | OC18H37 | 78–79 | C43H78O4 | 78.36 | 11.93 | 78.59 | 11.98 |
| 2g | O(CH2)3C6H5 | 107–109 | C25H26O4 | 76.90 | 6.71 | 76.42 | 6.77 |
| 2h | OCH2CHOHC8H17 | 103–106 | C27H46O6 | 69.49 | 9.94 | 69.64 | 9.80 |
| 2i | OCH2CHOHC10H21 | 104–106 | C31H54O6 | 71.23 | 10.41 | 71.20 | 10.33 |
| 2j | O(CH2)10COOH | 105–108 | C29H46O8 | 66.64 | 8.87 | 66.68 | 8.94 |
| 2k | O(CH2)10CH2OH | 69–72 | C29H50O6 | 70.41 | 10.19 | 70.10 | 10.11 |
| 2l | O(CH2)3OC6H4-2-C6H5 | 110–113 | C37H34O6 | | | N.O. | |
| 2m | O(CH2)3OC6H4-3-C6H5 | 65–69 | C37H34O6 | | | N.O. | |
| 2n | O(CH2)3OC6H4-4-C6H5 | 186–187 | C37H34O6 | 77.33 | 5.96 | 77.28 | 5.90 |
| 2o | O(CH2)2O-2-Naphthyl | 205–207 | C31H26O6 | 75.29 | 5.30 | 74.60 | 5.26 |
| 2p | O(CH2)2O-1-Naphthyl | 213–215 | C31H26O6 | 75.29 | 5.30 | 74.58 | 5.36 |

*Not Obtained

TABLE 2A

| Ex. | Structure | R | mp (°C.) | E.F. | Calcd C | Calcd H | Found C | Found H |
|---|---|---|---|---|---|---|---|---|
| 2r | 2,3-R,R-C6H3-COOH | $OC_{10}H_{21}$ | 57–58 | $C_{27}H_{46}O_4$ | 74.61 | 10.67 | 74.61 | 10.23 |
| 2s | | $OC_{14}H_{29}$ | 70–71 | $C_{35}H_{62}O_4$ | 76.87 | 11.43 | 76.32 | 11.33 |
| 2t | 3,4-R,R-C6H3-COOH | $OC_{10}H_{21}$ | 117–118 | $C_{27}H_{46}O_4$ | 74.61 | 10.67 | 74.88 | 10.88 |
| 2u | | $OC_{14}H_{29}$ | 112–113 | $C_{35}H_{62}O_4$ | 76.87 | 11.43 | 76.64 | 11.44 |
| 2v | 2,4-R,R-C6H3-COOH | $OC_{10}H_{21}$ | 50–52 | $C_{27}H_{46}O_4$ | 74.61 | 10.67 | 74.26 | 10.90 |
| 2w | | $OC_{14}H_{29}$ | 53–54 | $C_{35}H_{62}O_4$ | 76.87 | 11.43 | 76.77 | 11.09 |
| 2x | 2,5-R,R-C6H3-COOH | $C_{10}H_{21}$ | 64–66 | $C_{27}H_{46}O_4$ | 74.61 | 10.67 | 74.41 | 10.56 |
| 2y | | $C_{14}H_{29}$ | 72–73 | $C_{35}H_{62}O_4$ | 76.87 | 11.43 | 76.49 | 11.15 |

EXAMPLE 3

3,5-Bis(decyloxy)phenylcarbamic acid phenylmethyl ester

To a stirred, ice bath cooled solution of 5.0 g (0.0115 mol) of 3,5-bis(decyloxy)benzoic acid in 100 ml of anhydrous toluene was added dropwise 3.0 ml (0.0138 mol) of diphenylphosphoryl azide followed by dropwise solution of 1.9 ml (0.0138 mol) of triethylamine. The reaction mixture was stirred in the ice bath for 75 minutes and then was heated at 90° for 2 hours. Benzyl alcohol (100 ml) was added and the solution was stirred and heated at 90° for 3.5 hours. The solvent was removed under reduced pressure and most of the excess benzyl alcohol was removed at 80°/0.1 mm. Sodium bicarbonate solution (100 ml) was added to the residue and the product was extracted with ethyl acetate. The dried extract was concentrated at reduced pressure to an oil which was purified by HPLC using 25% hexane-ethyl acetate to give 4.87 g (79% yield) of 3,5-bis(decyloxy)phenylcarbamic acid phenylmethyl ester as an oil.

Anal. Calcd for $C_{34}H_{53}NO_4$: C, 75.65; H, 9.90; N, 2.59. Found: C, 75.52; H, 9.79; N, 2.68.

The compounds in Table 3 were prepared using the procedure in Example 3 starting with the appropriate carboxylic acid.

TABLE 3

3,5-R,R-C6H3-NHCOOR'

| Ex. | R | R' | mp (°C.) | E.F. | Calcd C | Calcd H | Calcd N | Found C | Found H | Found N |
|---|---|---|---|---|---|---|---|---|---|---|
| 3a | $OC_4H_9$ | Bz | 43–45 | $C_{22}H_{29}NO_4$ | 71.13 | 7.87 | 3.77 | 71.21 | 7.95 | 3.84 |
| 3b | $OC_6H_{13}$ | Bz | liquid | $C_{26}H_{37}NO_4$ | 73.04 | 8.72 | 3.28 | 72.63 | 8.92 | 3.35 |
| 3c | $OC_8H_{17}$ | Bz | liquid | $C_{30}H_{45}NO_4$ | 74.50 | 9.38 | 2.90 | 75.02 | 9.71 | 3.07 |
| 3d | $OC_{12}H_{25}$ | Bz | 48–50 | $C_{38}H_{61}NO_4$ | 76.59 | 10.32 | 2.35 | 76.27 | 10.20 | 2.23 |
| 3e | $OC_{14}H_{29}$ | Bz | 59–61 | $C_{42}H_{69}NO_4$ | 77.37 | 10.67 | 2.15 | 77.60 | 10.93 | 2.08 |
| 3f | $OC_{18}H_{37}$ | Bz | 74–76 | $C_{50}H_{85}NO_4$ | 78.58 | 11.21 | 1.83 | 78.66 | 11.01 | 1.75 |
| 3g | $O(CH_2)_3C_6H_5$ | Bz | 89–91 | $C_{32}H_{33}NO_4$ | 77.55 | 6.71 | 2.83 | 77.15 | 6.67 | 2.70 |
| 3h | $OCH_2CH(OAc)C_8H_{17}$ | Bz | liquid | $C_{38}H_{57}NO_8$ | | | | N.O. | | |
| 3i | $O(CH_2)_4COOCH_3$ | Bz | liquid | $C_{26}H_{33}NO_8$ | | | | N.O. | | |
| 3j | $O(CH_2)_{10}COOCH_3$ | Bz | liquid | $C_{38}H_{57}NO_8$ | | | | N.O. | | |
| 3k | $O(CH_2)_3OC_6H_4\text{-}2\text{-}C_6H_5$ | Bz | 84–90 | $C_{44}H_{41}NO_6$ | | | | N.O. | | |
| 3l | $O(CH_2)_3OC_6H_4\text{-}3\text{-}C_6H_5$ | Bz | 100–106 | $C_{44}H_{41}NO_6$ | | | | N.O. | | |
| 3m | $O(CH_2)_3OC_6H_4\text{-}4\text{-}C_6H_5$ | Bz | 125–129 | $C_{44}H_{41}NO_6$ | 77.74 | 6.08 | 2.06 | 77.18 | 6.28 | 2.02 |
| 3n | $O(CH_2)_2O\text{-}2\text{-Naphthyl}$ | Bz | 160–163 | $C_{38}H_{33}NO_6$ | 76.11 | 5.55 | 2.34 | 75.59 | 5.61 | 2.26 |
| 3o | $OCOC_9H_{19}$ | Bz | liquid | $C_{34}H_{49}NO_6$ | | | | N.O. | | |

*Not Obtained

EXAMPLE 4

3,5-bis(decyloxy)benzeneamine

A mixture of 34 g (0.063 mol) of 3,5-bis(decyloxy)-phenylcarbamic acid phenylmethyl ester and 4.0 g of 10% palladium on charcoal in 650 ml of ethyl acetate was shaken under a hydrogen atmosphere at room temperature for 4 hours. The reaction mixture was filtered to remove the catalyst and the filtrate was concentrated under reduced pressure to yield 25 g (98% yield, mp 48°–50°) of 3,5-bis(decyloxy)benzeneamine.

Anal. Calcd for $C_{26}H_{47}NO_2$: C, 76.98; H, 11.68; N, 3.45. Found: C, 76.82; H, 11.49; N, 3.39.

The compounds in Table 4 were prepared using the procedure of Example 4 starting with the appropriate phenyl carbamic acid benzyl ester.

tate, 2.65 (12.3 mmol) of 1,8-bis(dimethylamino)naphthalene (Proton sponge) and 0.21 g (1.38 mmol) of sodium iodide in 50 ml of anhydrous acetonitrile and 15 ml of anhydrous DMF was stirred at reflux under an argon atmosphere for 27 hours. The reaction mixture was concentrated under reduced pressure and the residue was extracted with ethyl acetate. The extract was washed with 0.5N HCl, dried and concentrated under reduced pressure to an oil which was purified by HPLC using 15% ethyl acetate-hexane to give 1.2 g (44% yield, mp 36°–38°) of N-(2-methoxy-2-oxoethyl)-N-[3,5-bis(decyloxy)phenyl]glycine methyl ester.

Anal. Calcd for $C_{32}H_{55}NO_6$: C, 69.91; H, 10.08; N, 2.55. Found: C, 69.59; H, 10.10; N, 2.38.

The compounds in Table 5 were prepared using the procedure of Example 5 starting with the appropriate amine and bromo ester.

TABLE 4

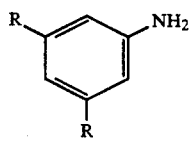

| | | | | Microanalytical Data | | | | | |
|---|---|---|---|---|---|---|---|---|---|
| | | | | Calcd | | | Found | | |
| Ex. | R | mp (°C.) | E.F. | C | H | N | C | H | N |
| 4a | $OC_4H_9$ | 39–41 | $C_{14}H_{23}NO_2$ | 70.85 | 9.77 | 5.90 | 70.63 | 9.64 | 5.99 |
| 4b | $OC_6H_{13}$ | 33–35 | $C_{18}H_{31}NO_2$ | 73.67 | 10.65 | 4.77 | 73.60 | 10.61 | 4.82 |
| 4c | $OC_8H_{17}$ | 41–43 | $C_{22}H_{39}NO_2$ | 75.59 | 11.25 | 4.01 | 76.06 | 11.17 | 3.84 |
| 4d | $OC_{12}H_{25}$ | 51–53 | $C_{30}H_{55}NO_2$ | 78.03 | 12.01 | 3.03 | 77.75 | 11.87 | 3.01 |
| 4e | $OC_{14}H_{29}$ | 57–58 | $C_{34}H_{63}NO_2$ | 78.85 | 12.26 | 2.70 | 79.06 | 12.31 | 2.60 |
| 4f | $OC_{18}H_{37}$ | 69–71 | $C_{42}H_{79}NO_2$ | 80.06 | 12.64 | 2.22 | 80.26 | 12.95 | 2.36 |
| 4g | $O(CH_2)_3C_6H_5$ | 78–80 | $C_{24}H_{27}NO_2$ | 79.74 | 7.53 | 3.87 | 80.87 | 7.71 | 3.90 |
| 4h | $OCH_2CH(OAc)C_8H_{17}$ | liquid | $C_{30}H_{51}NO_6$ | | | | N.O. | | |
| 4i | $O(CH_2)_4COOCH_3$ | liquid | $C_{18}H_{27}NO_6$ | | | | N.O. | | |
| 4j | $O(CH_2)_{10}COOCH_3$ | 57–59 | $C_{30}H_{51}NO_6$ | 69.06 | 9.85 | 2.68 | 69.23 | 9.96 | 2.68 |
| 4k | $O(CH_2)_3OC_6H_4$-2-$C_6H_5$ | 75–83 | $C_{36}H_{35}NO_4$ | | | | N.O. | | |
| 4l | $O(CH_2)_3OC_6H_4$-3-$C_6H_5$ | 40–45 | $C_{36}H_{35}NO_4$ | 79.24 | 6.47 | 2.57 | 78.82 | 6.52 | 2.57 |
| 4m | $O(CH_2)_3OC_6H_4$-4-$C_6H_5$ | 149–150 | $C_{36}H_{35}NO_4$ | 79.24 | 6.47 | 2.57 | 78.54 | 6.51 | 2.50 |
| 4n | $O(CH_2)_2O$-2-Naphthyl | 177–181 | $C_{30}H_{27}NO_4$ | | | | N.O. | | |
| 4o | $O(CH_2)_2O$-1-Naphthyl | 175–178 | $C_{30}H_{27}NO_4$ | | | | N.O. | | |
| 4p | $OCOC_9H_{19}$ | 43–44 | $C_{26}H_{43}NO_4$ | 72.02 | 10.00 | 3.23 | 71.78 | 9.82 | 3.31 |

EXAMPLE 5

N-(2-Methoxy-2-oxoethyl)-N-[3,5-bis(decyloxy)-phenyl]glycine methyl ester

A mixture of 2.0 g (4.93 mmol) of 3,5-bis(decyloxy)-benzenamine, 1.4 ml (14.8 mmol) of methyl bromoace-

TABLE 5

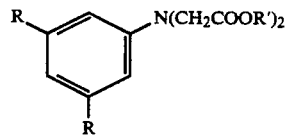

| | | | | | Microanalytical Data | | | | | |
|---|---|---|---|---|---|---|---|---|---|---|
| | | | | | Calcd | | | Found | | |
| Ex. | R | R' | mp (°C.) | E.F. | C | H | N | C | H | N |
| 5a | $OC_4H_9$ | $CH_3$ | liquid | $C_{20}H_{31}NO_6$ | 62.97 | 8.19 | 3.67 | 62.65 | 8.19 | 3.71 |
| 5b | $OC_6H_{13}$ | $CH_3$ | liquid | $C_{24}H_{39}NO_6$ | 65.88 | 8.98 | 3.20 | 65.76 | 8.97 | 3.22 |
| 5c | $OC_8H_{17}$ | $CH_3$ | liquid | $C_{28}H_{47}NO_6$ | 68.12 | 9.60 | 2.84 | 68.13 | 9.73 | 2.86 |
| 5d | $OC_{12}H_{25}$ | $CH_3$ | 43–44 | $C_{36}H_{63}NO_6$ | 71.36 | 10.48 | 2.31 | 71.40 | 10.60 | 2.46 |
| 5e | $OC_{14}H_{29}$ | Bz | 58–62 | $C_{52}H_{79}NO_6$ | 76.71 | 9.79 | 1.72 | 76.68 | 9.98 | 1.66 |
| 5f | $OC_{18}H_{37}$ | Bz | 64–66 | $C_{60}H_{95}NO_6$ | 77.79 | 10.34 | 1.51 | 77.57 | 10.06 | 1.52 |
| 5g | $O(CH_2)_3C_6H_5$ | Bz | liquid | $C_{42}H_{43}NO_6$ | | | | N.O. | | |
| 5h | $OCH_2CH(OAc)C_8H_{17}$ | $CH_3$ | liquid | $C_{36}H_{59}NO_{10}$ | 64.94 | 8.93 | 2.10 | 65.09 | 8.90 | 1.98 |
| 5i | $O(CH_2)_4COOCH_3$ | $CH_3$ | liquid | $C_{24}H_{35}NO_{10}$ | 57.94 | 7.09 | 2.82 | 57.73 | 6.95 | 2.81 |
| 5j | $O(CH_2)_3OC_6H_4$-2-$C_6H_5$ | Bz | liquid | $C_{54}H_{51}NO_8$ | | | | N.O. | | |
| 5k | $O(CH_2)_3OC_6H_4$-3-$C_6H_5$ | Bz | liquid | $C_{54}H_{51}NO_8$ | | | | N.O. | | |

TABLE 5-continued

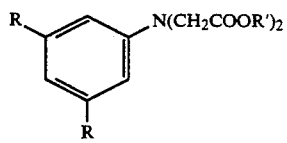

|  |  |  |  |  | Microanalytical Data | | | | | |
|---|---|---|---|---|---|---|---|---|---|---|
|  |  |  |  |  | Calcd | | | Found | | |
| Ex. | R | R' | mp (°C.) | E.F. | C | H | N | C | H | N |
| 5l | O(CH₂)₃OC₆H₄-4-C₆H₅ | Bz | 94–96 | C₅₄H₅₁NO₈ | 77.03 | 6.11 | 1.66 | 76.60 | 6.14 | 1.70 |
| 5m | O(CH₂)₂O-2-Naphthyl | Bz | 120–125 | C₄₈H₄₃NO₈ | 75.67 | 5.69 | 1.84 | 75.55 | 5.79 | 1.74 |
| 5n | O(CH₂)₂O-1-Naphthyl | Bz | 150–153 | C₄₈H₄₃NO₈ | 75.67 | 5.69 | 1.84 | 75.23 | 5.69 | 1.66 |
| 5o | CONHC₁₄H₂₉ | Bz | 110–111 | C₅₄H₈₁N₃O₆ | 74.40 | 9.40 | 4.84 | 74.77 | 9.31 | 4.82 |
| 5p | CONHC₁₈H₃₇ | Bz | 105–110 | C₆₂H₉₇N₃O₆ | 75.95 | 9.97 | 4.29 | 76.15 | 10.14 | 4.36 |
| 5q | CONH-1-Adamantyl | Bz | 169–171 | C₄₆H₅₃N₃O₆ | 74.27 | 7.18 | 5.65 | 74.07 | 7.15 | 5.62 |
| 5r | C₁₉H₃₉ | Bz | 50–51 | C₆₂H₉₉NO₄ | 80.72 | 10.82 | 1.52 | 80.54 | 10.59 | 1.51 |
| 5s | OCOC₉H₁₉ | Bz | liquid | C₄₄H₅₉NO₈ |  |  |  | N.O. |  |  |
| 5t | COOC₁₀H₂₁ | Bz | liquid | C₄₆H₆₃NO₈ |  |  |  | N.O. |  |  |

EXAMPLE 6

N-(Carboxymethyl)-N-[3,5-bis(decyloxy)phenyl]glycine

A solution of 0.205 g (0.373 mmol) of N-(2-methoxy-2-oxoethyl)-N-[3,5-bis(decyloxy)phenyl]glycine methyl ester and 1.5 ml (1.5 mmol) of 1.0N NaOH in 10 ml of methanol was stirred at reflux for 30 minutes. The solvent was removed under reduced pressure and the residue was acidified with 0.18 ml of acetic acid, the product was extracted with ethyl acetate and the dried extract was concentrated at reduced pressure to a solid. Recrystallization from methanol-water gave 61 mg (mp 110°–114°) of N-(carboxymethyl)-N-[3,5-bis(decyloxy)phenyl]glycine.

Anal. Calcd for C₃₀H₅₁NO₆: C, 69.06; H, 9.85; N, 2.68. Found: C, 69.09; H, 9.93; N, 2.57

The compounds in Table 6 were prepared using the procedure of Example 6 for methyl ester starting materials and using the procedure of Example 8 for benzyl ester stating materials.

TABLE 6

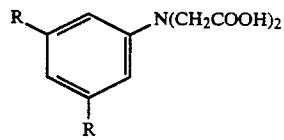

|  |  |  |  | Microanalytical Data | | | | | |
|---|---|---|---|---|---|---|---|---|---|
|  |  |  |  | Calcd | | | Found | | |
| Ex. | R | mp (°C.) | E.F. | C | H | N | C | H | N |
| 6a | OC₄H₉ | 147–149 | C₁₈H₂₇NO₆ | 61.17 | 7.70 | 3.96 | 61.12 | 7.60 | 3.97 |
| 6b | OC₆H₁₃ | 120–122 | C₂₂H₃₅NO₆ | 64.52 | 8.61 | 3.42 | 64.42 | 8.81 | 3.56 |
| 6c | OC₈H₁₇ | 119–123 | C₂₆H₄₃NO₆ | 67.07 | 9.31 | 3.01 | 67.11 | 9.51 | 2.90 |
| 6d | OC₁₂H₂₅ | 106–109 | C₃₄H₅₉NO₆ | 70.67 | 10.29 | 2.42 | 70.57 | 10.46 | 2.35 |
| 6e | OC₁₄H₂₉ | 103–106 | C₃₈H₆₇NO₆ | 72.00 | 10.65 | 2.21 | 72.01 | 10.54 | 2.13 |
| 6f | OC₁₈H₃₇ | 85–89 | C₄₆H₈₃NO₆ | 74.05 | 11.21 | 1.88 | 73.58 | 11.07 | 1.82 |
| 6g | O(CH₂)₃C₆H₅ | 150–153 | C₂₈H₃₁NO₆ | 70.42 | 6.54 | 2.93 | 70.54 | 6.64 | 2.85 |
| 6h | OCH₂CHOHC₈H₁₇ | 121–125 | C₃₀H₅₁NO₈ | 65.07 | 9.28 | 2.53 | 65.12 | 9.15 | 2.54 |
| 6i | O(CH₂)₄COOH | 172–174 | C₂₀H₂₇NO₁₀ | 54.42 | 6.17 | 3.17 | 54.56 | 6.23 | 3.20 |
| 6j | O(CH₂)₁₀COOCH₃ | 74–76 | C₃₄H₅₅NO₁₀ | 64.03 | 8.69 | 2.20 | 63.89 | 8.75 | 2.07 |
| 6k | O(CH₂)₁₀COOH | 146–147 | C₃₂H₅₁NO₁₀ | 63.03 | 8.43 | 2.30 | 62.69 | 8.40 | 2.32 |
| 6l | O(CH₂)₃OC₆H₄-2-C₆H₅ | 100–112 | C₄₀H₃₉NO₈ | 72.60 | 5.94 | 2.12 | 72.34 | 5.95 | 2.05 |
| 6m | O(CH₂)₃OC₆H₄-3-C₆H₅ | foam | C₄₀H₃₉NO₈ | 72.60 | 5.94 | 2.12 | 71.84 | 5.77 | 1.93 |
| 6n | O(CH₂)₃OC₆H₄-4-C₆H₅ | 155–159 | C₄₀H₃₉NO₈ | 72.60 | 5.94 | 2.12 | 72.17 | 5.97 | 2.08 |
| 6o | O(CH₂)₂O-2-Naphthyl | 185–192 | C₃₄H₃₁NO₈ | 70.21 | 5.37 | 2.41 | 68.40 | 5.19 | 2.40 |
| 6p | O(CH₂)₂O-1-Naphthyl | 169–170 | C₃₄H₃₁NO₈ | 70.21 | 5.37 | 2.41 | 69.53 | 5.68 | 2.31 |
| 6q | CONHC₁₃H₂₉ | 169–176 | C₄₀H₆₉N₃O₆ | 69.83 | 10.11 | 6.11 | 70.01 | 10.06 | 6.07 |
| 6r | CONHC₁₈H₃₇ | 175–181 | C₄₈H₈₅N₃O₆ | 72.05 | 10.71 | 5.25 | 72.14 | 11.04 | 5.24 |
| 6s | CONH-1-Adamantyl | 285–290 | C₃₂H₄₁N₃O₆ | 68.18 | 7.33 | 7.45 | 68.09 | 7.30 | 7.43 |
| 6t | C₁₉H₃₉ | 88–92 | C₄₈H₈₇NO₄ | 77.67 | 11.82 | 1.89 | 77.40 | 11.89 | 2.14 |
| 6u | OCOC₉H₁₉ | 140–145 | C₃₀H₄₇NO₈ | 65.55 | 8.62 | 2.55 | 65.27 | 8.73 | 2.68 |
| 6v | COOC₁₀H₂₁ | 100–102 | C₃₂H₅₁NO₈ | 66.52 | 8.90 | 2.42 | 66.51 | 8.99 | 2.50 |

EXAMPLE 7

N-[3,5-bis(Decyloxy)phenyl]-N-[2-oxo-2-(phenylmethoxy)ethyl]glycine phenylmethyl ester A mixture of 20.0 g (0.0493 mol) of 3,5-bis(decyloxy)benzenamine, 23.6 ml (0.148 mol) of benzyl bromoacetate, 26.4 (0.123 mol) of 1,8-bis(dimethylamino)naphthalene and 2.1 g of sodium iodide in 300 ml acetonitrile and 65 ml of DMF was stirred at reflux for 48 hours. The reaction mixture was concentrated under reduced pressure and the residue was extracted with ethyl acetate. The extract was washed with 0.5N HCl, with saturated NaHCO₃, dried and concentrated under reduced pressure to an oil. Purification by HPLC using 10% ethyl acetate-hexane gave 15.7 g (45% yield, mp 55°-57°) of N-[3,5-bis(decyloxy)phenyl]-N-[2-oxo-2-(phenylmethoxy)ethyl]glycine phenylmethyl ester.

Anal. Calcd for $C_{44}H_{63}NO_6$: C, 75.28; H, 9.04; N, 2.00. Found: C, 75.49; H, 9.14; N, 2.10.

EXAMPLE 8

N-(Carboxymethyl)-N-[3,5-bis(decyloxy)phenyl]glycine

A mixture of 10.2 g (0.0145 mol) of N-[3,5-bis(decyloxy)phenyl]-N-[2-oxo-2-(phenylmethoxy)ethyl]glycine phenylmethyl ester and 1.5 g of 10% palladium on charcoal in 500 ml of THF was shaken in a hydrogen atmosphere at room temperature for 7 hours. The catalyst was removed by filtration and the filtrate was concentrated under reduced pressure to a solid which was recrystallized from acetonitrile to give 5.66 g (75% yield, mp 110°-114°) of N-(carboxymethyl)-N-[3,5-bis(decyloxy)phenyl]glycine.

EXAMPLE 9

N,N'-Didecyl-5-nitro-1,3-benzenedicarboxamide

To 30 g (0.14 mol) of 5-nitroisophthalic acid suspended in 120 ml of thionyl chloride was added 2 ml of DMF and the solution was stirred at reflux for 3.5 hours. The excess thionyl chloride was removed at reduced pressure and the residue acid chloride was dissolved in 220 ml of anhydrous tetrahydrofuran. This solution was added dropwise to 64 ml (0.32 mol) of decyl amine and 44 ml (0.32 mol) of triethylamine in 350 mol of anhydrous tetrahydrofuran over 30 minutes with ice bath cooling. The reaction mixture was stirred at room temperature for 4 hours and then poured into 3 L of water. The resultant solid was removed by filtration and recrystallized from methanol to give 51.5 g (74% yield, mp 115°-116°) of N,N'-didecyl-5-nitro-1,3-benzenedicarboxamide.

Anal. Calcd for $C_{28}H_{47}N_3O_4$: C, 68.68; H, 9.67; N, 8.58. Found: C, 68.45; H, 9.56; N, 8.67.

The compounds in Table 7 were prepared by the procedure of Example 9.

TABLE 7

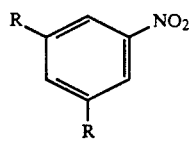

| Ex. | R | mp (°C.) | E.F. | Calcd C | Calcd H | Calcd N | Found C | Found H | Found N |
|---|---|---|---|---|---|---|---|---|---|
| 9a | $CONHC_{14}H_{29}$ | 110–114 | $C_{36}H_{63}N_3O_4$ | 71.84 | 10.55 | 6.98 | 72.15 | 10.70 | 6.93 |
| 9b | $CONHC_{18}H_{37}$ | 100–110 | $C_{44}H_{79}N_3O_4$ | 74.00 | 11.15 | 5.88 | 73.98 | 11.01 | 5.80 |
| 9c | CONH-1-Adamantyl | >350 | $C_{28}H_{35}N_3O_4$ | 70.42 | 7.39 | 8.80 | 70.20 | 7.51 | 8.95 |

EXAMPLE 10

5-Amino-N,N'-didecyl-1,3-benzenedicarboxamide

A mixture of 21 g (0.043 mol) of N,N'-didecyl-5-nitro-1,3-benzenedicarboxamide and 7.0 g of 10% palladium on carbon in 250 ml of tetrahydrofuran was shaken under hydrogen pressure (52 psi initially) on a Parr Hydrogenator for 17 hours. The catalyst was removed by filtration and the solvent was removed from the filtrate at reduced pressure to give a solid which was recrystallized from methanol-water to give 15.3 g (77% yield, mp 188°-189°) of 5-amino-N,N'-didecyl-1,3-benzenedicarboxamide.

Anal. Calcd for $C_{28}H_{49}N_3O_2$: C, 73.16; H, 10.74; N, 9.14. Found: C, 72.93; H, 10.70; N, 8.90.

Using the procedure of Example 10, hydrogenation of N,N'-ditetradecyl-5-nitro-1,3-benzenedicarboxamide gave 5-amino-N,N'-ditetradecyl-1,3-benzenedicarboxamide, mp 171°-178°.

Using the procedure of Example 10, hydrogenation of 5-nitro-N,N'-bis(tricyclo[3.3.1.1./3,7/]dec-1-yl)-1,3-benzenedicarboxamide gave 5-amino-N,N'-bis(tricyclo[3.3.1.1./3,7]dec-1-yl)-1,3-benzenedicarboxamide (mp >300°, Anal. Calcd for $C_{28}H_{37}N_3O_2$: C, 75.13; H, 8.33; N, 9.39. Found: C, 74.88; H, 8.25; N, 9.47.

EXAMPLE 11

N-[3,5-Bis[(decylamino)carbonyl]phenyl]glycine methyl ester

A mixture of 0.202 g (0.455 mmol) of 5-amino-N,N'-didecyl-1,3-benzenedicarboxamide, 0.17 ml (1.8 mmol) of methyl bromoacetate, 0.14 g (1 mmol) of potassium carbonate and 0.15 g (1 mmol) of sodium iodide in 10 ml of acetone and 2 ml of DMF was stirred at reflux for 20 hours. Water was added and the product was extracted with ethyl acetate. The dried extract was concentrated at reduced pressure to an oil which was crystallized from methanol-water to give 0.1608 g (67% yield, mp 108°-109°) of N-[3,5-bis[(decylamino)carbonyl]phenyl]glycine methyl ester.

Anal. Cacld for $C_{31}H_{53}N_3O_4$: C, 70.02; H, 10.05; N, 7.90. Found: C, 69.74; H, 10.21; N, 7.73.

EXAMPLE 12

N-[3,5-Bis[(decylamino)carbonyl]phenyl]glycine

A solution of 0.103 g (0.19 mmol) of N-[3,5-bis(decylamino)carbonyl]phenyl]glycine methyl ester and 0.4 ml (0.4 mmol) of 1.0N NaOH was kept at room temperature for 18 hours. Water (30 ml) was added and the pH was adjusted to 4 by the addition of acetic acid. The resultant solid was filtered and recrystallized from methanol-water to give 0.079 g (81% yield, mp 172°-173°) of N-[3,5-bis[(decylamino)carbonyl]phenyl glycine.

Anal. Calcd for $C_{30}H_{51}N_3O_4$: C, 69.60; H, 9.93; N, 8.12. Found: C, 69.29; H, 9.95; N, 8.11.

EXAMPLE 13

N-[3,5-Bis[(decylamino)carbonyl]phenyl]glycine phenylmethyl ester

A mixture of 7.0 g (15.2 mmol) of 5-amino-N,N'-didecyl-1,3-benzenedicarboxamide, 9.7 ml of benzylbromoacetate, 4.6 (30.4 mmol) of sodium iodide and 4.2 g (30.4 mmol) of potassium carbonate in 150 ml of acetone and 50 ml of DMF was stirred at reflux for 26 hours. The reaction mixture was filtered and the solvents were removed from the filtrate at reduced pressure. The residue was purified by HPLC using 35% ethyl acetate-hexane. The pure fractions were combined and recrystallized from methylene chloride-ether to give 4.3 g (47% yield, mp 102°–104°) of N-[3,5-bis[decylamino)-carbonyl]phenyl]glycine phenylmethyl ester. The nmr spectrum was consistent with the structure.

EXAMPLE 14

N-[3,5-bis[(decylamino)carbonyl]phenyl]glycine from the phenylmethyl ester

A mixture of 4.29 g (7.05 mmol) of N-[3,5-bis[(decylamino)carbonyl]phenyl]glycine phenylmethyl ester and 0.5 g of 10% palladium on carbon in 125 ml of tetrahydrofuran was shaken in a hydrogen atmosphere at room temperature for 16 hours. The catalyst was removed by filtration and the filtrate was concentrated at reduced pressure. The residue was triturated with ether and filtered to give 3.31 g (91% yield, mp 168°–171°) of N-[3,5-bis(decylamino)carbonyl]phenyl]glycine.

EXAMPLE 15

N-[3,5-Bis[(decylamino)carbonyl]phenyl]-N-(2-methoxy-2-oxoethyl)glycine methyl ester A mixture of 10.0 g (0.022 mol) of 5-amino-N,N'-didecyl-1,3-benzenedicarboxamide, 31 ml (0.33 mol) of methyl bromoacetate, 6.6 g (0.044 mol) of sodium iodide, 6.1 g (0.044 mol) of potassium carbonate and 0.32 g (0.001 mol) of tetrabutylammonium bromide in 100 ml of DMF was stirred and heated at 100° for 67 hours. The reaction mixture was concentrated on the oil pump and 100 ml of saturated NaHCO$_3$ solution was added to the residue. The product was extracted with ethyl acetate and the extract was washed with 10% sodium bisulfite solution. The dried extract was concentrated at reduced pressure to an oil which was purified by HPLC using 35% ethyl acetate-toluene. The combined pure fractions were crystallized from methanol-water to give 8.2 g (63% yield, mp 71°–75°) of N-[3,5-bis[(decylamino)carbonyl]phenyl]-N-(2-methoxy-2-oxoethyl)glycine methyl ester.

Anal. Calcd for C$_{34}$H$_{57}$N$_3$O$_6$: C, 67.63; H, 9.51; N, 6.96. Found: C, 67.42; H, 9.81; N, 6.88.

EXAMPLE 16

N-(Carboxymethyl)-N-[3,5-bis[(decylamino)carbonyl]phenyl]glycine

A solution of 8.2 g (0.0136 mol) of N-[3,5-bis[(decylamino)carbonyl]phenyl]-N-(2-methoxy-2-oxoethyl)glycine methyl ester and 54 ml (0.054 mol) of 1.0N NaOH in 425 ml of methanol was left at room temperature for 22 hours. The residue was dissolved in 250 ml of water and the pH was adjusted to 3.0 with 1N HCl. The resultant solid was removed by filtration and recrystallized from methanol-water to give 2.96 g (38% yield, mp 164°–167°) of N-(carboxymethyl)-N-[3,5-bis[(decylamino)carbonyl]phenyl]glycine.

Anal. Calcd for C$_{32}$H$_{53}$N$_3$O$_6$: C, 66.75; H, 9.28; N, 7.30. Found: C, 66.35; H, 9.20; N, 7.04.

EXAMPLE 17

3,5-bis[(1-Oxodecyl)amino]benzoic acid

To a mixture of 5 g (0.033 mol) of 3,5-diaminobenzoic acid in 100 ml of methylene chloride, 50 ml of THF and 18 ml (0.13 mol) of triethylamine stirred at room temperature was added 17 ml (0.08 mol) of decanoyl chloride dropwise over 10 minutes. The reaction mixture was stirred for 18 hours, filtered and the filtrate was concentrated at reduced pressure. Water was added to the residue and the product was extracted with ethyl acetate. The dried extract was concentrated at reduced pressure and the solid residue was recrystallized twice from methanol-water to give 8.6 g (57% yield, mp 208°–209°) of 3,5-bis[(1-oxodecyl)amino]benzoic acid.

Anal. Calcd for C$_{27}$H$_{44}$N$_2$O$_4$: C, 70.40; H, 9.63; N, 6.08. Found: C, 70.32; H, 9.60; N, 6.08.

The compounds in Table 8 were prepared using the procedure of Example 17 starting from the appropriate dihydroxybenzoic acid or diaminobenzoic acid.

TABLE 8

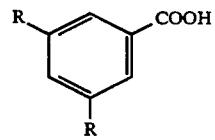

| | | | | Microanalytical Data | | | | | |
|---|---|---|---|---|---|---|---|---|---|
| | | | | Calcd | | | Found | | |
| Ex. | R | mp (°C.) | E.F. | C | H | N | C | H | N |
| 17a | OCOC$_9$H$_{19}$ | 50–52 | C$_{27}$H$_{42}$O$_6$ | 70.10 | 9.15 | | 70.05 | .08 | |
| 17b | NHCOC$_{11}$H$_{23}$ | 198–201 | C$_{31}$H$_{52}$N$_2$O$_4$ | 72.05 | 10.14 | 5.42 | 71.93 | 10.10 | 5.32 |
| 17c | NHCOC$_{13}$H$_{27}$ | 188–191 | C$_{35}$H$_{60}$N$_2$O$_4$ | 73.38 | 10.56 | 4.89 | 73.12 | 10.57 | 4.83 |
| 17d | NHCOC$_{15}$H$_{31}$ | 185–188 | C$_{39}$H$_{68}$N$_2$O$_4$ | 74.47 | 10.90 | 4.45 | 74.50 | 10.88 | 4.53 |
| 17e | OCONHC$_8$H$_{17}$ | 186–187 | C$_{25}$H$_{40}$N$_2$O$_6$ | 64.63 | 8.68 | 6.03 | 64.64 | 8.54 | 6.15 |
| 17f | NHCONHC$_{17}$H$_{35}$ | 250–2880 | C$_{43}$H$_{78}$N$_4$O$_4$ | 72.22 | 10.99 | 7.83 | 71.50 | 11.16 | 7.69 |
| 17g | NHCONHC$_8$H$_{17}$ | 229–231 | C$_{25}$H$_{42}$N$_4$O$_4$ | 64.91 | 9.15 | 12.11 | 63.84 | 9.15 | 11.81 |

EXAMPLE 18

[3,5-bis[(1-Oxodecyl)amino]phenyl]carbamic acid phenylmethyl ester

To a suspension of 5.0 g (10.85 mmol) of 3,5-bis[(1-oxodecyl)amino]benzoic acid in 150 ml of anhydrous toluene cooled in an ice bath and stirred under an argon atmosphere was added 2.8 ml (13.0 mmol) of diphenylphosphoryl azide followed by 1.8 ml (13.0 mmol) of triethylamine. The reaction mixture was stirred in the ice bath for 1.5 hours, at room temperature for 1 hour and then at 90° C. for 2 hours. Benzyl alcohol (39 ml, 0.38 mol) was added and heating at 90° was continued for 4 hours. The solvent was removed at reduced pressure and most of the excess benzyl alcohol was removed at 80°/1 mm. NaHCO$_3$ solution was added and the product was extracted with ethyl acetate. The dried extract was concentrated at reduced pressure and the residue was purified by HPLC using 25% ethyl acetate-hexane to give 27.8 g (45% yield) of [3,5-bis[(1-oxodecyl)amino]phenyl]carbamic acid phenylmethyl ester as a yellow foam. The nmr and mass spectra were compatible with the structure.

EXAMPLE 19

N,N'-(5-Amino-1,3-phenylene)bisdecanamide

A mixture of 2.77 g (4.9 mmol) of [3,5-bis[(1-oxodecyl)amino]phenyl]carbamic acid phenylmethyl ester and 0.6 g of 10% palladium on carbon in 60 ml of THF was shaken under a hydrogen atmosphere at room temperature and pressure for 8 hours. The catalyst was removed by filtration and the filtrate was concentrated at reduced pressure. The resultant solid was triturated with ether and filtered to give 1.94 g (92% yield, mp 152°-154°) of N,N'-(5-amino-1,3-phenylene)bisdecanamide.

Anal. Calcd for $C_{26}H_{45}N_3O_2$: C, 72.34; H, 10.51; N, 9.73. Found: C, 72.02; H, 10.29; N, 9.56.

EXAMPLE 20

N-[3,5-bis[(1-Oxodecyl)amino]phenyl]-N-[2-oxo-2-(phenylmethoxy)ethyl]glycine phenylmethyl ester A mixture of 1.92 g (4.45 mmol) of N,N'-(5-amino-1,3-phenylene)bisdecanamide, 10.6 ml (0.061 mol) of benzyl bromoacetate, 2.4 g (11.1 mmol) of 1,8-bis(dimethylamino)-naphthalene and 0.19 g (1.25 mmol) of sodium iodide in 50 ml of acetonitrile and 15 ml of DMF was stirred and refluxed under an argon atmosphere for 36 hours. The solvents were removed at reduced pressure and the residue was dissolved in ethyl acetate. The extract was washed with 0.05N HCl, with NaHCO$_3$ solution, dried and concentrated to a brown solid. Purification by HPLC using 25% ethyl acetate-hexane gave 0.9 g which was recrystallized from acetone-hexane to give 0.064 g (20% yield, mp 127°-129°) of N-[3,5-bis[(1-oxodecyl)amino]phenyl]-N-[2-oxo-2-(phenylmethoxy)ethyl]glycine phenylmethyl ester.

Anal. Calcd for $C_{44}H_{61}N_3O_6$: C, 72.60; H, 8.45; N, 5.7. Found: C, 72.28; H, 8.52; N, 5.71.

EXAMPLE 21

N-(Carboxymethyl)-N-3,5-bis[(1-oxodecyl)amino]phenyl]glycine

A mixture of 0.625 g (0.86 mmol) of N-[3,5-bis[(1-oxodecyl)amino]phenyl]-N-[2-oxo-2-(phenylmethoxy)ethyl]glycine phenylmethyl ester and 0.2 g of 10% palladium on carbon in 25 ml of THF was stirred in a hydrogen atmosphere at room temperature for 5 hours. The catalyst was removed by filtration and the filtrate was concentrated at reduced pressure to a solid which was recrystallized from methanol-water to give 0.29 g (62% yield, mp 100°-102°) of N-(carboxymethyl)-N-3,5-bis[(1-oxodecyl)amino]glycine.

Anal. Calcd for $C_{30}H_{49}N_3O_6$: C, 65.79; H, 9.02; N, 7.67. Found: C, 65.21; H, 8.86; N, 7.58.

EXAMPLE 22

5-Nitro-1,3-benzenedicarboxylic acid ditetradecyl ester

A mixture of 1.0 g (4.7 mmol) of 5-nitroisophthalic acid, 3.1 ml (10.3 mmol) of 1-bromotetradecane and 2.0 g (15 mmol) of potassium carbonate in 40 ml of anhydrous DMF was stirred and heated at 100° for 20 hours. Water was added to the cooled reaction mixture and the resultant solid was filtered and recrystallized from methylene chloride-methanol to give 2.1 g (74% yield, mp 60°-61°) of 5-nitro-1,3-benzenedicarboxylic acid ditetradecyl ester.

Anal. Calcd for $C_{36}H_{61}NO_6$: C, 71.60; H, 10.18; N, 2.32. Found: C, 71.68; H, 10.26; N, 2.34.

Using this procedure the reaction of 5-nitroisophthalic acid with 1-bromodecane gave 5-nitro-1,3-benzenedicarboxylic acid didecyl ester (mp 48°-50°, Anal. Calcd for $C_{28}H_{45}NO_6$: C, 68.40; H, 9.23; N, 2.85. Found: C, 67.68; H, 9.13; N, 2.86.

EXAMPLE 23

5-Amino-1,3-benzenedicarboxylic acid ditetradecyl ester

A mixture of 2.09 g of 5-nitro-1,3-benzenedicarboxylic acid ditetradecyl ester and 0.5 g of 10% palladium on carbon in 80 ml of ethyl acetate and 25 ml of THF was shaken under an initial hydrogen pressure of 53 psi for 17 hours. The catalyst was removed by filtration and the filtrate was concentrated to give 1.96 g of pure 5-amino-1,3-benzenedicarboxylic acid ditetradecyl ester, mp 74°-75°.

Anal. Calcd for $C_{36}H_{63}NO_4$: C, 75.34; H, 11.06; N, 2.44. Found: C, 75.49; H, 11.23; N, 2.49.

Using this procedure, the hydrogenation of 5-nitro-1,3-benzenedicarboxylic acid didecyl ester gave 5-amino-1,3-benzenedicarboxylic acid didecyl ester (mp 72°-73°, Anal. Calcd for $C_{28}H_{47}NO_4$: C, 72.84; H, 10.26; N, 3.03. Found: C, 73.09; H, 10.26; N, 2.99.

EXAMPLE 24

N-[3,5-bis[(tetradecyloxy)carbonyl]phenyl]-N-[2-oxo-2-(phenylmethoxy)ethyl]glycine phenylmethyl ester and N-[[3,5-bis(tetradecyloxy)carbonyl]phenyl]glycine phenylmethyl ester A mixture of 1.96 g (3.4 mmol) of 5-amino-1,3-benzenedicarboxylic acid ditetradecyl ester, 5.4 ml (34 mmol) of benzyl bromoacetate, 1.8 g (8.5 mmol) of 1,8-bis(dimethylamino) naphthalene and 0.2 g (1.36 mmol) of sodium iodide in 40 ml of acetonitrile and 20 ml of DMF was stirred at reflux for 48 hours. The solvents were removed at reduced pressure and the residue was dissolved in ethyl acetate. The extract was washed with 0.05N HCl twice, with NaHCO$_3$ solution, dried and concentrated. The residue was purified by chromatography on silica gel using 10% ethyl acetate-hexane to give 0.14 g of N-[[3,5-bis(tetradecyloxy)carbonyl]phenyl]glycine phenylmethyl ester and 0.43 g, 57°-58°, of N-[3,5-bis[(tetradecyloxy)carbonyl]phenyl]-N-[2-oxo-2-(phenylmethoxy)ethyl]glycine phenylmethyl ester.

Anal. Calcd for $C_{54}H_{79}NO_8$: C, 74.53; H, 9.15; N, 1.61. Found: C, 74.50; H, 9.22; N, 1.63.

EXAMPLE 25

N-(Carboxymethyl)-N-[3,5-bis[(tetradecyloxy)carbonyl]phenyl]glycine

A mixture of 0.43 g of N-[3,5-bis[(tetradecyloxy)carbonyl]phenyl]-N-[2-(phenylmethoxy)-2-oxoethyl]glycine phenylmethyl ester and 0.2 g of 10% palladium on carbon in 30 ml of ethyl acetate and 20 ml of THF was shaken under an initial hydrogen pressure of 51 psi for 2 hours. The catalyst was removed by filtration and the filtrate was concentrated at reduced pressure to a solid which was recrystallized from methanol-water to give 0.28 g (82% yield, mp 84°–87°) of N-(carboxy-methyl)-N-[3,5-bis[(tetradecyloxy)carbonyl]phenyl]glycine.

Anal. Calcd for $C_{40}H_{67}NO_8$: C, 69.63; H, 9.79; N, 2.03. Found: C, 69.65; H, 9.81; N, 1.98.

EXAMPLE 26

N-[[3,5-bis-(Tetradecyloxy)carbonyl]phenyl]glycine

A mixture of 0.14 g of N-[[3,5-bis-(tetradecyloxy)carbonyl]phenylglycine phenylmethyl ester and 0.2 g of 10% palladium on carbon in 15 ml of ethyl acetate and 10 ml of THF was shaken under an initial hydrogen pressure of 55 psi for 75 minutes. The catalyst was removed by filtration and the filtrate was concentrated at reduced pressure to give 0.10 g (83% yield, mp 88°–89°) of N-[[3,5-bis-(tetradecyloxy)carbonyl]phenyl]glycine.

Anal. Calcd for $C_{38}_{65}NO_6$: C, 72.23; H, 10.37; N, 2.22. Found: C, 72.54; H, 10.46; N, 2.26.

EXAMPLE 27

3,5-Didecylbenzenamine

To 5.2 g (0.011 mol) of nonyl triphenylphosphonium bromide suspended in 100 ml of anhydrous THF stirred in an ice bath under an argon atmosphere was added dropwise over 15 minutes 7.0 ml (0.011 mol) of 1.6M butyl lithium in hexane. The reaction mixture was stirred in the ice bath for 30 minutes and a solution of 0.97 g (0.0054 mol) of 5-nitroisophthaldehyde in 15 ml of THF was added dropwise over 15 minutes. The reaction mixture was stirred at room temperature for 17 hours and then the solvent was removed at reduced pressure. The residue was treated with 10 ml of 1N HCl and the product was extracted with ethyl acetate. The dried extract was concentrated at reduced pressure and the crude product was purified by chromatography on 100 g of silica gel using 20% methylene chloride-hexane to give 1.79 g (78% yield) of the desired olefin as an oil. This olefin and 0.5 g of 10% palladium on carbon in 75 ml of THF was shaken under an initial hydrogen pressure of 53 psi for 4 hours. The catalyst was removed by filtration and the filtrate was concentrated under reduced pressure to give 1.6 g of 3,5-didecylbenzenamine as a tan oil. The mass and nmr spectra were consistent with the structure.

Using this procedure, the reaction of octadecyl triphenylphosphonium bromide and butyl lithium gave the Wittig reagent, which was allowed to react with 5-nitroisophthaldehyde. The purified intermediate thus obtained was hydrogenated to yield 3,5-dinonadecylbenzenamine (mp 51°–53°, Anal. Calcd for $C_{44}H_{83}N$: C, 84.40; H, 13.36; N, 2.24. Found: C, 84.46; H, 13.15; N, 2.18.

Using this procedure, the reaction of octadecyl triphenylphosphonium bromide and butyl lithium gave the Wittig reagent, which was allowed to react with 3-nitrobenzaldehyde. The purified intermediate thus obtained was hydrogenated to yield 3-nonadecylbenzenamine (mp 50°–51°, Anal. Calcd for $C_{25}H_{45}N$: C, 83.49; H, 12.61; N, 3.89. Found: C, 83.50; H, 12.79; N, 3.86.

EXAMPLE 28

N-(3,5-Didecylphenyl)-N-[2-oxo-2-(phenylmethoxy)ethyl]glycine phenylmethyl ester A mixture of 1.6 g (4.28 mmol) of 3,5-didecylbenzenamine, 6.8 ml (0.0428 mol) of benzylbromoacetate, 3.0 g (0.021 mol) of potassium carbonate and 0.65 g (4.28 mmol) of sodium iodide in 50 ml of DMF was stirred and heated at 85° for 46 hours. The solvent was removed at reduced pressure and water was added to the residue. The product was extracted with ethyl acetate and the dried extract was concentrated at reduced pressure to an oil. Purification by HPLC using 10% ethyl acetate-hexane gave 1.69 g (59% yield) of N-(3,5-didecylphenyl)-N-[2-oxo-2-(phenylmethoxy)]glycine phenylmethyl ester as a yellow oil.

Anal. Calcd for $C_{44}H_{63}NO_4$: C, 78.88; N, 9.48; N, 2.09. Found: C, 78.71; H, 9.58; N, 1.97.

EXAMPLE 29

N-(Carboxymethyl)-N-(3,5-didecylphenyl) glycine

A mixture of 1.65 g of N-(3,5-didecylphenyl)-N-[2-(phenylmethoxy)-2-oxoethyl]glycine phenylmethyl ester and 0.5 g of 10% palladium on carbon in 100 ml of THF was shaken under an initial hydrogen pressure of 53 psi for 5 hours. The catalyst was removed by filtration and the filtrate was concentrated at reduced pressure to a solid which was recrystallized from methanol-water to give 0.98 g (81% yield, mp 78°–81°) of N-(carboxymethyl)-N-(3,5-didecylphenyl)glycine.

Anal. Calcd for $C_{30}H_{51}NO_4$. 0.5 $H_2O$: C, 72.25; H, 10.51; N, 2.80; $H_2O$, 1.80 Found: C, 72.44; H, 10.93; N, 2.65; $H_2O$, 2.27.

EXAMPLE 30

4-[3,5-bis(decyloxy)phenyl]2,6-morpholinedione

To 2.0 g (3.83 mmol) of N-(carboxymethyl)-N-[3,5-bis(decyloxy)phenyl]glycine in 100 ml of methylene chloride stirred at room temperature was added 0.9 g (4.37 mmol) of dicyclohexylcarbodiimide The reaction mixture was stirred at room temperature for 17 hours. After cooling in an ice bath, the precipitate was removed by filtration and the filtrate was concentrated at reduced pressure to a solid which was recrystallized from hexane to give 1.7 g (88% yield, mp 62°–62°) of 4-[3,5-bis(decyloxy)phenyl]2,6-morpholinedione.

Anal. Calcd for $C_{30}H_{49}NO_5$: C, 71.53; H, 9.80; N, 2.78. Found: C, 71.76; H, 10.03; N, 2.84.

EXAMPLE 31

N-(2-Methoxy-2-oxoethyl)-N-[3,5-bis(decyloxy)phenyl]glycine

A solution of 0.469 g of 4-[3,5-bis(decyloxy)phenyl]2,6-morpholinedione in 50 ml of methanol was warmed to 50° and then was left at room temperature for 17 hours. The solvent was removed at reduced pressure to give 0.44 g, mp 61°–62° of pure N-(2-methoxy-2-oxoethyl)-N-[3,5-bis(decyloxy)phenyl]glycine.

Anal. Calcd for $C_{31}H_{53}NO_6$: C, 69.50; H, 9.97; N, 2.61. C, 69.30; H, 10.01; N, 2.62.

EXAMPLE 32

N-(Carbamoylmethyl)-N-[3,5-bis(decyloxy)phenyl]glycine ammonium salt

Into a solution of 0.50 g of 4-[3,5bis(decyloxy)phenyl]2,6-morpholinedione dissolved in 50 ml of methylene chloride stirred at room temperature was bubbled ammonia gas for 10 minutes. After standing at room temperature for 17 hours, the precipitate was removed by filtration to give 0.51 g, mp 149°–152° of pure N-(carboxymethyl)-N-[3,5-bis(decyloxy)phenyl]glycine ammonium salt.

Anal. Calcd for $C_{30}H_{52}N_2O_5 \cdot NH_3$: C, 67.00; H, 10.31; N, 7.81. Found: C, 67.18; H, 10.39; N, 7.71.

EXAMPLE 33

N-(2-Diethylaminoethoxy-2-oxoethyl)-N-[3,5-bis(decyloxy)phenyl]glycine monohydrochloride salt A solution of 0.43 g (0.85 mmol) of 4-[3,5-bis(decyloxy)phenyl]2,6-morpholinedione and 0.23 ml (1.71 mmol) of N,N-diethylethanolamine in 40 ml of methylene chloride was kept at room temperature for 3.5 days. The solvent was removed at reduced pressure and the residue was dissolved in ethyl acetate. The extract was washed with water and then with 0.5N HCl, dried and concentrated at reduced pressure to a yellow foam which was dissolved in ether and cooled. Filtration gave 0.46 g (82% yield, mp 89°–91°) of N-(2-diethylaminoethoxy-2-oxoethyl)-N-[3,5-bis(decyloxy)phenyl]glycine monohydrochloride salt.

Anal. Calcd for $C_{36}H_{64}N_2O_6 \cdot HCl$: C, 65.78; H, 9.97; N, 4.26; Cl−, 5.39. Found: C, 66.19; H, 10.17; N, 4.20; Cl−, 5.11.

EXAMPLE 34

3-(Octadecyloxy)benzenamine a) A mixture of 4.0 g (0.029 mol) of 3-nitrophenol, 10.5 g (0.032 mol) of 1-bromooctadecane and 6.0 g (0.043 mol) of anhydrous potassium carbonate in 75 ml of anhydrous DMF was stirred and heated at 75° for 23 hours. The solvent was removed at reduced pressure and water was added to the residue. The product was extracted with ether and the dried extract was concentrated at reduced pressure to a solid which was purified by HPLC using 15% methylene chloride-hexane to give 9.0% g (80% yield) of 3-(oxtadecyloxy)nitrobenzene.

b) This was dissolved in 150 ml of THF, 2.0 g of 10% palladium on carbon was added and the mixture was shaken until an initial hydrogen pressure of 52 psi for 5.5 hours when uptake ceased. The catalyst was removed by filtration and the filtrate was concentrated at reduced pressure to a solid which was recrystallized from methanol to give 7.7 g (92% yield, mp 77°–78°) of 3-(octadecyloxy)benzenamine.

The compounds in Table 9 were prepared by alkylation of 3-nitrophenol with the required bromide using the procedure of Example 34a. Hydrogenation of the nitro compounds (in Table 9) as in procedure 34b gave the anilines in Table 10.

TABLE 9

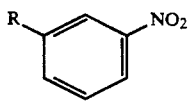

| | | | | | Microanalytical Data | | | | | |
| | | | | | Calcd | | | Found | | |
| Ex. | R | mp (°C.) | E.F. | | C | H | N | C | H | N |
| --- | --- | --- | --- | --- | --- | --- | --- | --- | --- | --- |
| 34a | $OC_{10}H_{21}$ | oil | $C_{16}H_{25}NO_3$ | | | | | N.O.* | | |
| 34b | $O(CH_2)_2O$-2-Naphthyl | 110–112 | $C_{18}H_{15}NO_4$ | | 69.89 | 4.89 | 4.53 | 69.69 | 4.74 | 4.24 |
| 34c | $O(CH_2)_3OC_6H_4$-3-$C_{15}H_{31}$ | 49–51 | $C_{30}H_{45}NO_4$ | | 74.50 | 9.38 | 2.90 | 74.34 | 9.15 | 2.89 |

*Not Obtained

TABLE 10

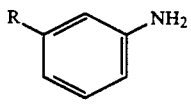

| | | | | | Microanalytical Data | | | | | |
| | | | | | Calcd | | | Found | | |
| Ex. | R | mp (°C.) | E.F. | | C | H | N | C | H | N |
| --- | --- | --- | --- | --- | --- | --- | --- | --- | --- | --- |
| 34d | $OC_{10}H_{21}$ | 49–52 | $C_{16}H_{25}NO_3$ | | | | | N.O.* | | |
| 34e | $O(CH_2)_2O$-2-Naphthyl | 145–147 | $C_{18}H_{17}NO_4$ | | 77.40 | 6.13 | 5.01 | 77.28 | 6.18 | 4.87 |
| 34f | $O(CH_2)_3OC_6H_4$-3-$C_{15}H_{31}$ | 64–66 | $C_{30}H_{47}NO_4$ | | 79.42 | 10.44 | 3.09 | 79.04 | 10.50 | 3.15 |

*Not Obtained

EXAMPLE 35

N-[2-Methoxy-2-oxoethyl)-N-[3-(octadecyloxy)phenyl]glycine methyl ester

A mixture of 1.0 g (2.77 mmol) of 3-(octadecyloxy)benzenamine, 0.8 ml (8.3 mmol) of methyl bromoacetate, 1.5 g (6.9 mmol) of 1,8-bis(dimethylamino)naphthalene and 0.116 g (0.78 mmol) of sodium iodide in 15 ml of acetonitrile was stirred at reflux under an argon atmosphere for 20 hours. The reaction mixture was diluted with 50 ml of toluene and washed with 0.05N HCl, with saturated $NaHCO_3$ solution dried and concentrated at reduced pressure to a solid which was recrystallized from ether-hexane three times to give 0.61 g (44% yield, mp 75°–77°) of N-(2-methoxy-2-oxoethyl)-N-[3-(octadecyloxy)phenyl]glycine methyl ester.

Anal. Calcd for $C_{30}H_{51}NO_5$: C, 71.25; H, 10.16; N, 2.77. Found: C, 71.01; H, 10.14; N, 2.83.

The compounds in Table 11 were prepared by the procedure of Example 35.

TABLE 11

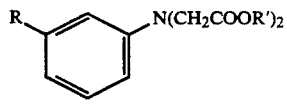

R—[phenyl]—N(CH$_2$COOR')$_2$

| | | | | | Microanalytical Data | | | | | |
|---|---|---|---|---|---|---|---|---|---|---|
| | | | | | Calcd | | | Found | | |
| Ex. | R | R' | mp (°C.) | E.F. | C | H | N | C | H | N |
| 35a | OC$_{10}$H$_{21}$ | CH$_3$ | 56–57 | C$_{22}$H$_{35}$NO$_5$ | 67.15 | 8.96 | 3.56 | 67.12 | 9.17 | 3.48 |
| 35b | OCOC$_{17}$H$_{35}$ | Bz | 60–63 | C$_{42}$H$_{57}$NO$_6$ | 75.08 | 8.55 | 2.08 | 74.92 | 8.61 | 2.11 |
| 35c | OCONHC$_{17}$H$_{35}$ | Bz | 63–64 | C$_{42}$H$_{58}$N$_2$O$_6$ | 73.44 | 8.51 | 4.08 | 73.22 | 8.32 | 4.08 |
| 35d | CONHC$_{10}$H$_{21}$ | CH$_3$ | 72–74 | C$_{23}$H$_{36}$N$_2$O$_5$ | 65.69 | 8.63 | 6.66 | 64.88 | 8.51 | 6.39 |
| 35e | NHCONHC$_{18}$H$_{37}$ | Bz | 72–75 | C$_{43}$H$_{61}$N$_3$O$_5$ | 73.78 | 8.78 | 6.00 | 73.64 | 8.70 | 5.88 |
| 35f | C$_{19}$H$_{39}$ | Bz | oil | C$_{43}$H$_{61}$NO$_4$ | | | | N.O. | | |
| 35g | O(CH$_2$)$_2$O-2-Naphthyl | Bz | 68–71 | C$_{36}$H$_{33}$NO$_6$ | 75.11 | 5.78 | 2.43 | 74.73 | 5.56 | 2.38 |
| 35h | CONH-1-Adamantyl | Bz | 115–117 | C$_{35}$H$_{38}$N$_2$O$_5$ | 74.18 | 6.76 | 4.94 | 74.10 | 6.80 | 4.88 |
| 35i | O(CH$_2$)$_3$OC$_6$H$_4$-3-C$_{15}$H$_{31}$ | Bz | 51–53 | C$_{48}$H$_{63}$NO$_6$ | 76.87 | 8.47 | 1.87 | 77.06 | 8.37 | 1.76 |

*Not Obtained

EXAMPLE 36

N-(Carboxymethyl)-N-[3-(octadecyloxy)phenyl]glycine

A solution of 0.56 g (1.11 mol) of N-(2-methoxy-2-oxoethyl)-N-[3-(octadecyloxy)phenyl]glycine methyl ester and 4.4 ml (4.4 mmol) of 1N NaOH in 50 ml of methanol was stirred at reflux under argon atmosphere for 75 minutes. After standing at room temperature for 17 hours the precipitate was removed by filtration. The solid was suspended in 100 ml of 1N HCl and extracted with ethyl acetate. The dried extract was concentrated at reduced pressure and the resultant solid was recrystallized from methanol-water to give 0.31 g (60% yield, mp 135°–138°) of N-(carboxymethyl)-N-[3-(octadecyloxy)phenyl]glycine.

Anal. Calcd for $C_{28}H_{47}NO_5$: C, 70.40; H, 9.92; N; 2.93. Found: C, 70.75; H, 10.23; N, 2.97.

The compounds in Table 12 were prepared using the procedure of Example 36 if the precursor was a methyl ester or the procedure of Example 38 if the precursor was a benzyl ester.

EXAMPLE 37

N-[3-(Octadecyloxy)phenyl]-N-[2-oxo-2-(phenylmethoxy)ethyl]glycine phenylmethyl ester A mixture of 5.5 g (0.015 mol) of 3-(octadecyloxy)-benzenamine, 7.3 ml (0.046 mol) of benzyl bromoacetate, 8.2 g (0.038 mol) of 1,8-bis(dimethylamino)naphthalene, 0.64 g (4.26 mmol) of sodium iodide in 100 ml of anhydrous acetonitrile and 25 ml of anhydrous DMF was stirred at reflux under an argon atmosphere for 48 hours. The solvents were removed at reduced pressure and the residue was dissolved in ethyl acetate and washed with 0.05N HCl, with saturated NaHCO$_3$ solution dried and concentrated at reduced pressure. Purification by HPLC using 15% ethyl acetate-hexane gave, after recrystallization of the combined pure fractions from ether-hexane, 6.56 g (69% yield, mp 55°–57°) of N-[3-(octadecyloxy)phenyl]-N-[2-oxo-2-(phenylmethoxy)ethyl]glycine phenylmethyl ester.

Anal. Calcd for $C_{42}H_{59}NO_5$: C, 76.67; H, 9.04; N, 2.13. Found: C, 76.40; H, 9.01; N, 1.78.

EXAMPLE 38

N-(Carboxymethyl)-N-[3-(octadecyloxy)phenyl]glycine from the phenylmethyl ester

A mixture of 6.9 g (0.01 mol) of N-[3-(octadecyloxy)-phenyl]-N-2[-oxo-2-(phenylmethoxy)ethyl]glycine phenylmethyl ester and 1.0 g of 10% palladium on carbon on 150 ml of THF was shaken under an initial hydrogen

TABLE 12

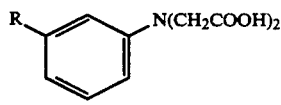

R—[phenyl]—N(CH$_2$COOH)$_2$

| | | | | Microanalytical Data | | | | | |
|---|---|---|---|---|---|---|---|---|---|
| | | | | Calcd | | | Found | | |
| Ex. | R | mp (°C.) | E.F. | C | H | N | C | H | N |
| 36a | OC$_{10}$H$_{21}$ | 142–145 | C$_{20}$H$_{31}$NO$_5$ | 65.73 | 8.55 | 3.83 | 65.66 | 8.76 | 3.85 |
| 36b | OCOC$_{17}$H$_{35}$ | 131–133 | C$_{28}$H$_{45}$NO$_6$ | 68.40 | 9.23 | 2.85 | 68.15 | 9.49 | 3.01 |
| 36c | OCONHC$_{17}$H$_{35}$ | 166–169 | C$_{28}$H$_{46}$N$_2$O$_6$ | 66.37 | 9.15 | 5.53 | 66.40 | 9.05 | 5.62 |
| 36d | CONHC$_{10}$H$_{21}$ | 152–154 | C$_{21}$H$_{32}$N$_2$O$_5$ | 64.26 | 8.22 | 7.14 | 64.27 | 8.37 | 7.13 |
| 36e | NHCONHC$_{18}$H$_{37}$ | 152–155 | C$_{29}$H$_{49}$N$_3$O$_5$ | 67.02 | 9.50 | 8.08 | 67.23 | 9.56 | 8.10 |
| 36f | C$_{19}$H$_{39}$ | 123–125 | C$_{29}$H$_{49}$NO$_4$ | 73.22 | 10.38 | 2.94 | 73.18 | 10.43 | 2.97 |
| 36g | O(CH$_2$)$_2$O-2-Naphthyl | 147–149 | C$_{22}$H$_{21}$NO$_6$ | 66.85 | 5.35 | 3.54 | 66.90 | 5.47 | 3.51 |
| 36h | CONH-1-Adamantyl | 154–156 | C$_{21}$H$_{26}$N$_2$O$_5$ | 65.27 | 6.78 | 7.25 | 65.20 | 6.67 | 7.37 |
| 36i | O(CH$_2$)$_3$OC$_6$H$_4$-3-C$_{15}$H$_{31}$ | 129–132 | C$_{34}$H$_{51}$NO$_6$ | 71.67 | 9.02 | 2.06 | 71.53 | 9.17 | 2.35 | pressure of 50 psi until uptake ceased after 5 hours. The catalyst was removed by filtration and the filtrate was concentrated at reduced pressure to a solid which was recrystallized from ethyl acetate to give 4.43 g (88% yield, mp 130°–133°) of N-(carboxymethyl)-N-[3-(octadecyloxy)phenyl]glycine.

EXAMPLE 39

N-(Carboxymethyl)-N-(3-tetradecylphenyl)glycine

A mixture of 1.0 g (3.45 mmol) of 4-tetradecylphenyl aniline (Aldrich Chemical Company), 5.0 ml (0.052 mol) of methyl bromoacetate, 0.95 g (6.9 mmol) of potassium carbonate and 0.5 g (3.45 mmol) of sodium iodide in 15 ml of DMF was stirred and heated at 100° for 45 hours. The solvent was removed at reduced pressure and water was added to the residue. The product was extracted with ethyl acetate and the extract was washed with sodium bisulfite solution, dried and concentrated. The residue was purified by chromatography on silica gel using 25% ethyl acetate-hexane to give 0.7 g of N-(2-methoxy-2-oxoethyl)-N-(4-tetradecylphenyl)glycine methyl ester. This dimethyl ester was hydrolyzed by treatment with 1.5 ml of 6N NaOH in 50 ml of methanol. The mixture was warmed briefly to dissolve the ester and then was kept at room temperature for 3 days. The solvent was removed at reduced pressure and the residue was acidified to pH 2. The product was extracted with ethyl acetate and the dried extract was concentrated at reduced pressure to a solid which was recrystallized from methanol-water to give 0.26 g, mp 160°–165°, of N-(carboxymethyl)-N-(4-tetradecylphenyl)glycine.

Anal. Calcd for $C_{24}H_{39}NO_4$: C, 71.07; H, 9.69; N, 3.45. Found: C, 70.58; H, 9.73; N, 3.43.

The compounds in Table 13 were prepared using the procedure of Example 39.

TABLE 13

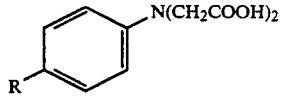

| | | | Microanalytical Data | | | | | |
|---|---|---|---|---|---|---|---|---|
| | | | Calcd | | | Found | | |
| Ex. | R | mp (°C.) | E.F. | C | H | N | C | H | N |
| 39a | H | 152–154 | $C_{10}H_{11}NO_4$ | known compound | | | | | |
| 39b | $C_4H_9$ | 107–109 | $C_{14}H_{19}NO_4$ | 63.38 | 7.22 | 5.28 | 63.52 | 7.31 | 5.27 |
| 39c | $C_8H_{17}$ | 130–140 | $C_{18}H_{27}NO_4$ | 67.26 | 8.47 | 4.36 | 66.73 | 8.23 | 4.38 |
| 39d | $C_{10}H_{21}$ | 112–115 | $C_{20}H_{31}NO_4$ | 68.74 | 8.94 | 4.01 | 68.38 | 8.84 | 3.96 |

EXAMPLE 40

3-Amino-N-octadecylbenzamide

To a mixture of 1.45 g (5.38 mmol) of octadecylamine and 1.1 ml (8 mmol) of triethylamine in 20 ml of methylene chloride stirred and cooled in an ice bath was added 1.00 g (5.38 mmol) of 3-nitrobenzoyl chloride in 30 ml of methylene chloride. The reaction mixture was stirred at room temperature for 17 hours and then was washed with 1N HCl. Some of the product was insoluble and was removed by filtration. The methylene chloride layer was concentrated at reduced pressure to give additional product which was combined with the original insoluble product and recrystallized from methanol to give 0.86 g, mp 98°–99°, of 3-nitro-N-octadecylbenzamide. This and 0.3 g of 10% palladium on carbon in 125 ml of THF was shaken under an initial hydrogen pressure of 52 psi until uptake ceased after 75 minutes. The catalyst was removed by filtration and the residue was recrystallized from methanol-water to give 0.6 g, mp 76°–77°, of 3-amino-N-octadecylbenzamide.

Anal. Calcd for $C_{25}H_{44}N_2O$: C, 77.26; H, 11.41; N, 7.21. Found: C, 77.07; H, 11.24; N, 7.03.

Using this procedure 3-nitrobenzoyl chloride was treated with decylamine to give 3-nitro-N-decylbenzamide, mp 86°–88°, which was hydrogenated to give 3-amino-N-decylbenzamide, mp 56°–58°, which gave nmr and mass spectra consistent with the structure.

Using this procedure 3-nitrobenzoyl chloride was treated with 1-adamantanamine to give 3-nitro-N-tricyclo[3.3.1.1/3,7/]dec-1-ylbenzamide (mp 157°–159°, Anal. Calcd for $C_{17}H_{20}N_2O_3$: C, 67.98;; H, 6.71; N, 9.33. Found: C, 67.22; H, 6.68; N, 9.34) which was hydrogenated to give 3-amino-N-tricyclo[3.3.1.1/3,7/]dec-1-ylbenzamide (mp 172°–173°, Anal. Calcd for $C_{17}H_{22}N_2O$: C, 75.52; H, 8.20; N, 10.36. Found: C, 75.47; H, 8.27; N, 10.35.

EXAMPLE 41

N-[3-[(Octadecylamino)carbonyl]phenyl-N-[2-oxo-2-(phenylmethoxy)ethyl]glycine phenylmethyl ester A mixture of 0.6 g (1.54 mmol) of 3-amino-N-octadecylbenzamide 1.2 ml (7.72 mmol) of benzyl bromoacetate, 1.32 g (6.16 mmol) of 1,8-bis(dimethylamino)naphthalene and 0.23 g (1.54 mmol) of sodium iodide in 40 ml of acetonitrile was stirred at reflux for 65 hours. The solvent was removed at reduced pressure and the residue was dissolved in ethyl acetate and washed with 0.05N HCl, with saturated NaHCO$_3$ solution, dried and concentrated to a solid. Chromatography on 70 g of 230–400 mesh silica gel using 30% ethyl acetate-hexane gave 0.4 g (38% yield, mp 70°–71°) of N-3-[(octadecylamino)carbonyl]-N-[2-oxo-2-(phenylmethoxy)ethyl]glycine phenylmethyl ester.

Anal. Calcd for $C_{43}H_{60}N_2O_5$: C, 75.40; H, 8.83; N, 4.09. Found: C, 75.13; H, 8.83; N, 4.19.

EXAMPLE 42

N-(Carboxymethyl)-N-[3-(octadecylamino)carbonyl]-phenyl[glycine

A mixture of 0.4 g of N-3-[(octadecylamino)carbonyl]-N-[2-oxo-2-(phenylmethoxy)ethyl]glycine phenylmethyl ester and 0.2 g of 10% palladium on carbon in 40 ml of ethyl acetate was shaken under an initial hydrogen pressure of 53 psi until uptake ceased after 2 hours. The catalyst was removed by filtration and the filtrate was concentrated at reduced pressure to a solid which was recrystallized from methanol-water to give 0.22 g, mp 143°–147°, of N-(carboxymethyl)-N-[3-(octadecylamino)carbonyl]phenyl]glycine.

Anal. Calcd for $C_{29}H_{48}N_2O_5$: C, 69.01; H, 9.59; N, 5.55. Found: C, 68.96; H, 9.57; N, 5.54.

EXAMPLE 43

N-(3-Nitrophenyl)octadecanamide

To 2.0 g (14.5 mmol) of 3-nitroaniline and 4.5 ml (32 mmol) of triethylamine in 60 ml of methylene chloride stirred at room temperature was added 5.4 ml (16 mmol) of octadecanoyl chloride in 10 ml of methylene chloride. The reaction mixture was kept at room temperature for 18 hours and then was washed with 1N HCl, dried and concentrated at reduced pressure to a solid. Recrystallization from methanol gave 5.6 g (95% yield, mp 75°–76°) of N-(3-nitrophenyl)octadecanamide.

Anal. Calcd for $C_{24}H_{40}N_2O_3$: C, 71.25; H, 9.97; N, 6.92. Found: C, 71.10; H, 10.25; N, 6.70.

EXAMPLE 44

N-(3-Aminophenyl)octadecanamide

A mixture of 5.5 g of N-(3-nitrophenyl)octadecanamide and 0.6 g of 10% palladium on carbon in 100 ml of ethyl acetate was shaken under an initial hydrogen pressure of 52 psi until uptake ceased after 23 hours. The catalyst was removed by filtration and the filtrate was concentrated at reduced pressure to a solid which was recrystallized from methanol-water to give 4.6 g (90% yield, mp 98°–102°) of N-(3-aminophenyl)octadecanamide.

Anal. Calcd for $C_{24}H_{42}N_2O$: C, 76.95; H, 11.30; N, 7.48. Found: C, 76.90; H, 11.27; N, 7.56.

EXAMPLE 45

N-(2-Methoxy-2-oxoethyl)-N-[3-[(1-oxooctadecyl)amino]phenyl]glycine methyl ester A mixture of 2.0 g (5.3 mmol) of N-(3-aminophenyl)octadecanamide, 2.5 ml (26.5 mmol) of methyl bromoacetate, 4.5 g (21 mmol) of 1,8-bis(dimethylamino)-naphthalene and 0.8 g (5.3 mmol) of sodium iodide in 100 ml of acetonitrile was stirred at reflux under an argon atmosphere for 46 hours. The solvent was removed at reduced pressure and the residue was dissolved in ethyl acetate. The extract was washed with 0.05N HCl, dried and concentrated at reduced pressure to a solid which was recrystallized twice from methanol-water to give 1.83 g (67% yield, mp 78°–79°) of N-(2-methoxy-2-oxoethyl)-N-[3-[(1-oxooctadecyl)amino]phenyl]glycine methyl ester.

Anal. Calcd for $C_{30}H_{50}N_2O_5$: C, 69.46; H, 9.72; N, 5.40. Found: C, 69.45; H, 9.48; N, 5.31.

EXAMPLE 46

N-(Carboxymethyl)-N-[3-[(1-oxooctadecyl)amino]phenyl]glycine

A mixture of 1.8 g N-(2-methoxy-2-oxoethyl)-N-[3-[(1-oxooctadecyl)amino]phenyl]glycine methyl ester and 2.4 ml of 6N NaOH in 30 ml of dioxane and 30 ml of methanol was heated to dissolve the solid and left at room temperature for 18 hours. The solid which precipitated was filtered, treated with 1N HCl and filtered again. Recrystallization from methanol-THF-water gave 1.35 g (79% yield, mp 135°–140°) of N-(carboxymethyl)-N-[3-[(1-oxooctadecyl)amino]phenyl]glycine.

Anal. Calcd for $C_{28}H_{46}N_2O_5$: C, 68.54; H, 9.45; N, 5.71. Found: C, 68.59; H, 9.63; N, 5.72.

EXAMPLE 47

N-(3-Hydroxyphenyl)-N-(2-methoxy-2-oxoethyl)glycine methyl ester

A mixture of 1.85 g (9.3 mmol) of 3-benzyloxyaniline, 4.4 ml (46.5 mmol) of methyl bromoacetate, 8.0 g (37 mmol) of 1,8 bis(dimethylamino)naphthalene and 1.4 g (9.3 mmol) of sodium iodide in 100 ml of acetonitrile was stirred at reflux for 41 hours. The solvent was removed at reduced pressure and the residue was dissolved in ethyl acetate. The extract was washed with 0.05N HCl, with saturated $NaHCO_3$ solution, dried and concentrated to an oil. Purification by chromatography on silica gel using 30% ethyl acetate-hexane gave 2.73 g (88% yield) of N-[3-(phenylmethoxy)phenyl]-N-(2-methoxy-2-oxoethyl)glycine methyl ester. The nmr and mass spectra was consistent with the structure. This material and 0.5 g of 10% palladium on carbon in 60 ml of ethyl acetate was shaken under an initial hydrogen pressure of 53 psi until uptake ceased after 24 hours. The catalyst was removed by filtration and the filtrate was concentrated at reduced pressure to an oil which was purified by chromatography on silica gel using 50% ethyl acetate-hexane to give 1.15 g (58% yield) of N-(3-hydroxyphenyl)-N-[2-methoxy-2-oxoethyl)glycine methyl ester as an oil. The nmr spectrum was consistent with the structure.

EXAMPLE 48

N-(2-Methoxy-2-oxoethyl)-N-[3-[(Z)-(9-octadecenyl)oxy]phenyl]glycine methyl ester A mixture of 0.24 g (0.95 mmol) of N-(3-hydroxyphenyl)-N-(2-methoxy-2-oxoethyl)glycine methyl ester, 0.33 g (1 mmol) of oleyl bromide, 0.15 g (1 mmol) of sodium iodide and 0.41 g (3 mmol) of potassium carbonate in 10 ml of acetone was stirred at reflux under argon for 18 hours. DMF (5 ml) was added and reflux was continued for 3 days. The solvents were removed at reduced pressure and the residue was dissolved in ethyl acetate. The extract was dried and concentrated at reduced pressure to an oil which was purified by chromatography on 230–400 mesh silica gel using 25% ethyl acetate-hexane to give 0.25 g (50% yield, mp 36°–37°) of N-(2-methoxy-2-oxoethyl)-N-[3-[(Z)-(9-octadecenyl)oxy]phenyl]glycine methyl ester. The nmr and spectra were consistent with the structure.

Using this procedure, the reaction of N-(3-hydroxyphenyl-N-(2-methoxy-2-oxoethyl)glycine methyl ester with linoleyl bromide gave N-(2-methoxy-2-oxoethyl)-N-[3-[(9Z,12Z)-(9,12-octadecadienyl)oxy]phenyl]glycine methyl ester as an oil. The structure was confirmed by nmr and mass spectra.

EXAMPLE 49

N (Carboxymethyl)-N-[3-[(Z)-(9-octadecenyl)oxy]-phenyl]glycine

A mixture of 0.29 g (0.57 mmol) of N-(2-methoxy-2-oxoethyl)-N-[3-[(Z)-(9-octadecenyl)oxy]phenyl]glycine methyl ester and 0.4 ml (2.4 mmol) of 6N NaOH in 2 ml of dioxane and 10 ml of methanol was warmed to dissolve the solid and left at room temperature for 16 hours. The solid was stirred with 1N HCl, filtered again and recrystallized from ethyl acetate-methanol-hexane to give 0.22 g, mp 128°–135°, of N-(carboxymethyl)-N-

[3-(Z)-(9-octadecenyl)oxy]phenylglycine. The nmr and mass spectra were consistent with the structure.

Using this procedure, base hydrolysis of N-(2-methoxy-2-oxoethyl)-N-[3-[(9Z,12Z)-(9,12-octadecadienyl]oxy]phenyl]glycine methyl ester gave N-(carboxymethyl)-N-[3-[(9Z,12Z)-(9,12-octadecadienyl]oxy]phenyl]glycine as a semisolid. The structure was confirmed by nmr and mass spectra.

EXAMPLE 50

N-(3-Aminophenyl)-N-(2-methoxy-2-oxoethyl)glycine methyl ester

A mixture of 5.0 g (0.036 mol) of 3-nitroaniline, 11 ml (0.11 mol) of methyl bromoacetate and 10 ml of diisopropylethyl amine in 10 ml of acetonitrile was stirred at reflux under an argon atmosphere for 3 days. The solvent was removed at reduced pressure and the residue was dissolved in ethyl acetate and washed with 0.1N HCl, with saturated $NaHCO_3$ solution, dried and concentrated at reduced pressure to an oil. Purification by HPLC using 5% ethyl acetate-hexane gave 4.95 g (49% yield, mp 54°–57°) of N-(3-nitrophenyl)-N-(2-methoxy-2-oxoethyl)glycine methyl ester. The nmr spectrum was consistent with the structure. This material and 0.5 g of 10% palladium on carbon in 100 ml of ethyl acetate was shaken under an initial hydrogen pressure of 53 psi for 23 hours. The catalyst was removed by filtration and the filtrate was concentrated at reduced pressure to 4.0 g of pure N-(3-aminophenyl)-N-(2-methoxy-2-oxoethyl)glycine methyl ester. The nmr spectrum was consistent with the structure.

EXAMPLE 51

N-(Carboxymethyl)-N-[3-[(Z)-(1-oxo-9-octadecenyl)amino]phenyl]glycine

To a solution of 0.486 g (1.94 mmol) of N-(3-aminophenyl)-N-(2-methoxy-2-oxoethyl)glycine methyl ester and 0.56 ml (4 mmol) of triethylamine in 25 ml of methylene chloride stirred at room temperature was added 0.86 ml (2.6 mmol) of oleoyl chloride (70%). The reaction mixture was stirred at room temperature for 3 hours and then was washed with 1N HCl, dried and concentrated to an oil. Purification by chromatography on silica gel using 50% ethyl acetate-hexane gave 0.97 g of N-(2-methoxy-2-oxoethyl)-N-3-[(Z)-(1-oxooctadecenyl)amino]phenyl]glycine methyl ester. This material was hydrolyzed by treatment with 1.6 ml (9.6 mmol) of 6N NaOH in 20 ml of methanol and 10 ml of dioxane at room temperature for 17 hours. The solvents were removed at reduced pressure and the residue was stirred with excess 1N HCl. The product was removed by filtration and recrystallized from methanol-water to give 0.75 g of N-(carboxymethyl)-N-[3-[(Z)-(1-oxo-9-octadecenyl)amino]phenyl]glycine as a waxy solid.

Anal. Calcd for $C_{28}H_{44}N_2O_5$: C, 68.82; H, 9.08; N, 5.73. Found: C, 67.60; H, 8.79; N, 5.49.

Using this procedure, the reaction of N-(3-aminophenyl)-N-(2-methoxy-2-oxoethyl)glycine methyl ester with linoleyl chloride gave N-(carboxymethyl)-N-[3-[(9Z,12Z)-(1-oxo-9,12-octadecadienyl)amino]phenyl]glycine (mp 135°–140°, Anal. Calcd for $C_{28}H_{42}N_2O_5$: C, 69.11; H, 8.70; N, 5.76. Found: C, 69.03; H, 8.79; N, 5.79.

EXAMPLE 52

3-Hydroxy-5-(octadecyloxy)benzoic acid phenylmethyl ester

A mixture of 30 g (0.123 mol) of 3,5-dihydroxybenzoic acid phenylmethyl ester, 40.9 g (0.123 mol) of 1-bromooctadecane, 17 g (0.123 mol) of anhydrous potassium carbonate in 500 ml of acetone and 10 ml of DMF was stirred at reflux for 25 hours. The reaction mixture was filtered and the filtrate was concentrated at reduced pressure to a solid. The residue was treated with water and the product was extracted with methylene chloride. The dried extract was concentrated at reduced pressure to a solid which was purified by HPLC using 1% ethyl acetate-methylene chloride to give 22 g (36% yield, mp 72°–75°) of 3-hydroxy-5-(octadecyloxy)benzoic acid phenylmethyl ester. The structure was confirmed by nmr and mass spectra.

EXAMPLE 53

3-(Octadecyloxy)-5-(3-phenoxypropoxy)benzoic acid phenylmethyl ester

A mixture of 12 g (0.024 mol) of 3-hydroxy-5-(octadecyloxy)benzoic acid phenylmethyl ester, 6 ml (0.038 ml) of 3-phenoxypropyl bromide, 3.6 g (0.024 mol) of sodium iodide and 10 g (0.072 mol) of potassium carbonate in 40 ml of acetone and 80 ml of DMF was stirred at reflux for 46 hours. The reaction mixture was filtered and the filtrate was concentrated to dryness at reduced pressure. Water was added to the residue and the product was extracted with ethyl acetate. The dried extract was concentrated at reduced pressure to an oil which was purified by HPLC using 5% ethyl acetate-hexane. The pure fractions were combined, triturated with hexane and filtered to give 14.6 g (96% yield, mp 46°–47°) of 3-(octadecyloxy)-5-(3-phenoxypropoxy)benzoic acid phenylmethyl ester. The structure was confirmed by nmr and mass spectra.

Anal. Calcd for $C_{41}H_{58}O_5$: C, 78.05; H, 9.27. Found: C, 77.89; H, 9.03.

The compounds in Table 14 were prepared using the procedure of Example 53.

TABLE 14

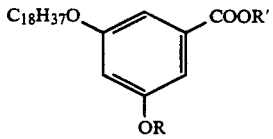

| Ex. | R | R' | mp (°C.) | E.F. | Calcd C | Calcd H | Calcd N | Found C | Found H | Found N |
|---|---|---|---|---|---|---|---|---|---|---|
| 53a | (CH$_2$)$_2$OH | Bz | 47–49 | C$_{34}$H$_{52}$O$_5$ | | | | | | N.O. |
| 53b | (CH$_2$)$_2$OAc | Bz | 44–46 | C$_{36}$H$_{54}$O$_6$ | | | | | | N.O. |
| 53c | CH$_2$COOCH$_3$ | Bz | 56–58 | C$_{35}$H$_{52}$O$_6$ | 73.91 | 9.21 | | 74.00 | 9.04 | |
| 53d | (CH$_2$)$_4$COOCH$_3$ | Bz | 40–42 | C$_{38}$H$_{58}$O$_6$ | | | | | | N.O. |
| 53e | (CH$_2$)$_{10}$COOCH$_3$ | Bz | 37–38 | C$_{44}$H$_{70}$O$_6$ | 76.04 | 10.15 | | 76.03 | 10.33 | |

TABLE 14-continued

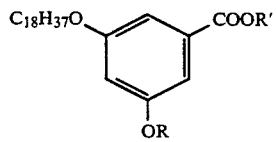

|  |  |  |  |  | Microanalytical Data | | | | | |
|  |  |  |  |  | Calcd | | | Found | | |
| Ex. | R | R' | mp (°C.) | E.F. | C | H | N | C | H | N |
| 53f | CO-1-Adamantyl | Bz | oil |  |  |  |  | N.O. |  |  |
| 53g | COCH($C_6H_5$)$_2$ | Bz | 47–49 | $C_{46}H_{58}O_5$ |  |  |  | N.O. |  |  |
| 53h | ($CH_2$)$_2$O-2-Naphthyl | Bz | 62–65 | $C_{44}H_{58}O_5$ | 79.24 | 8.77 |  | 78.90 | 8.93 |  |
| 53i | ($CH_2$)$_3$O-3-Pyridyl | Bz | 43–45 | $C_{40}H_{57}NO_5$ | 76.03 | 9.09 | 2.22 | 76.33 | 9.10 | 2.22 |
| 53j | ($CH_2$)$_3$O$C_6H_4$-3-$OCH_3$ | Bz | 54–55 | $C_{42}H_{60}O_6$ |  |  |  | N.O. |  |  |
| 53k | ($CH_2$)$_3$O$C_6H_4$-4-$OCH_3$ | Bz | 45–49 | $C_{42}H_{60}O_6$ |  |  |  | N.O. |  |  |
| 53l | ($CH_2$)$_3$O$C_6H_4$-4-OBz | $CH_3$ | 75–77 | $C_{42}H_{60}O_6$ | 76.33 | 9.15 |  | 76.04 | 9.09 |  |
| 53m | ($CH_2$)$_3$O$C_6H_4$-3-$NO_2$ | $CH_3$ | 76–78 | $C_{35}H_{53}NO_7$ | 70.09 | 8.91 | 2.34 | 69.89 | 8.99 | 2.27 |
| 53n | ($CH_2$)$_3$O$C_6H_4$-4-$COOCH_3$ | Bz | 59–61 | $C_{43}H_{60}O_7$ | 79.97 | 8.78 |  | 74.99 | 8.79 |  |
| 53o | ($CH_2$)$_2$O($CH_2$)$_2$O($CH_2$)$_2$O$C_2H_5$ | Bz | oil | $C_{40}H_{64}O_7$ |  |  |  | N.O. |  |  |

*Not Obtained

EXAMPLE 54

3-(Octadecyloxy)-5-(3-phenoxypropoxy)benzoic acid

A mixture of 14.6 g of 3-(octadecyloxy)-5-(3-phenoxypropoxy)benzoic acid phenylmethyl ester and 3 g of 10% palladium on carbon was shaken in a hydrogen atmosphere at room temperature for 2 hours. The catalyst was removed by filtration and the filtrate was concentrated to a solid which was recrystallized from ether-hexane to give 11.8 g (95% yield, mp 79°–81°) of 3-(octadecyloxy)-5-(3-phenoxypropoxy)benzoic acid.

Anal. Calcd for $C_{34}H_{52}O_5$: C, 75.52; H, 9.69. Found: C, 75.09; H, 9.80.

The compounds in Table 15 were prepared using the procedure of Example 54 if the precursor was a benzyl ester or by basic hydrolysis using sodium hydroxide, if the precursor was a methyl ester.

EXAMPLE 55

3-(Octadecyloxy)-5-(3-phenoxypropoxy)phenylcarbamic acid phenylmethyl ester

To a suspension of 10.7 g (0.02 mol) 3-(octadecyloxy)-5-(3-phenoxypropoxy)benzoic acid in 250 ml of anhydrous toluene cooled in an ice bath was added 5.1 ml (0.024 mol) of diphenylphosphoryl azide followed by 3.8 ml (0.028 mol) of triethylamine. The reaction mixture was stirred in an ice bath for 1 hour and then heated at 90° for 2 hours. After cooling to room temperature, 70 ml of benzyl alcohol was added. The reaction mixture was then stirred and heated at 90° for 18 hours. The solvent was removed at reduced pressure and the residue was dissolved in ethyl acetate. The extract was washed with saturated $NaHCO_3$ solution, dried and concentrated to an oil which was purified by HPLC using 10% ethyl acetate-hexane to give 10.9 g (85% yield, mp 68°–69°) of 3-(octadecyloxy)-5-(3-phenoxypropoxy)phenylcarbamic acid phenylmethyl ester. The structure was confirmed by nmr and mass spectra.

TABLE 15

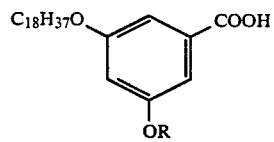

|  |  |  |  | Microanalytical Data | | | | | |
|  |  |  |  | Calcd | | | Found | | |
| Ex. | R | mp (°C.) | E.F. | C | H | N | C | H | N |
| 54a | ($CH_2$)OAc | 68–71 | $C_{29}H_{48}O_6$ |  |  |  | N.O. |  |  |
| 54b | ($CH_2$)$_2$OH | 105–106 | $C_{27}H_{46}O_5$ | 71.96 | 10.29 |  | 72.00 | 10.09 |  |
| 54c | $CH_2COOCH_3$ | 95–97 | $C_{28}H_{46}O_6$ | 70.26 | 9.69 |  | 70.00 | 9.73 |  |
| 54d | ($CH_2$)$_{10}COOCH_3$ | 68–71 | $C_{37}H_{64}O_6$ | 73.47 | 10.66 |  | 73.26 | 10.97 |  |
| 54e | CO-1-Adamantyl | 44–47 | $C_{36}H_{56}O_5$ | 76.01 | 9.92 |  | 76.15 | 10.21 |  |
| 54f | COCH($C_6H_5$)$_2$ | 83–86 | $C_{39}H_{52}O_5$ | 77.96 | 8.72 |  | 77.63 | 8.79 |  |
| 54g | ($CH_2$)$_2$O-2-Naphthyl | 98–103 | $C_{37}H_{52}O_5$ | 77.04 | 9.09 |  | 76.81 | 9.22 |  |
| 54h | ($CH_2$)$_3$O-3-Pyridyl | 93–94 | $C_{33}H_{51}NO_5$ | 73.16 | 9.49 | 2.59 | 73.17 | 9.45 | 3.07 |
| 54i | ($CH_2$)$_3$O$C_6H_5$ | 79–81 | $C_{34}H_{52}O_5$ | 75.52 | 9.69 |  | 75.09 | 9.80 |  |
| 54j | ($CH_2$)$_3$O$C_6H_4$-4-$OCH_3$ | 86–87 | $C_{35}H_{54}O_6$ | 73.65 | 9.54 |  | 73.85 | 9.73 |  |
| 54k | ($CH_2$)$_3$O$C_6H_4$-4-OBz | 99–101 | $C_{41}H_{58}O_6$ | 76.12 | 9.04 |  | 75.92 | 9.02 |  |
| 54l | ($CH_2$)$_3$O$C_6H_4$-4-OH | 92–95 | $C_{34}H_{52}O_6$ | 73.35 | 9.41 |  | 73.07 | 9.43 |  |
| 54m | ($CH_2$)$_3$O$C_6H_4$-3-$NO_2$ | 91–93 | $C_{34}H_{51}NO_7$ | 69.71 | 8.78 | 2.39 | 69.53 | 8.84 | 2.33 |
| 54n | ($CH_2$)$_3$O$C_6H_4$-4-$COOCH_3$ | 88–90 | $C_{36}H_{54}O_7$ | 72.21 | 9.09 |  | 72.02 | 9.17 |  |
| 54o | ($CH_2$)$_2$O($CH_2$)$_2$O($CH_2$)$_2$O$C_2H_5$ | 38–40 | $C_{33}H_{58}O_7$ | 69.93 | 10.31 |  | 69.62 | 10.15 |  |

*Not Obtained

The compounds in Table 16 were prepared using the procedure of Example 55, except for the compounds 55j and k, which were prepared using t-butyl alcohol in place of benzyl alcohol.

TABLE 16

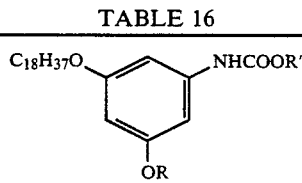

| Ex. | R | R' | mp (°C.) | E.F. | Calcd C | Calcd H | Calcd N | Found C | Found H | Found N |
|---|---|---|---|---|---|---|---|---|---|---|
| 55a | (CH$_2$)$_2$OAc | Bz | 45–52 | C$_{36}$H$_{55}$NO$_6$ | | | | N.O. | | |
| 55b | CH$_2$COOCH$_3$ | Bz | 81–84 | C$_{35}$H$_{53}$NO$_6$ | | | | N.O. | | |
| 55c | (CH$_2$)$_{10}$COOCH$_3$ | Bz | 46–48 | C$_{44}$H$_{71}$NO$_6$ | 74.43 | 10.08 | 1.97 | 74.00 | 9.60 | 1.64 |
| 55d | CO-1-Adamantyl | Bz | oil | C$_{43}$H$_{63}$NO$_5$ | | | | N.O. | | |
| 55e | COCH(C$_6$H$_5$)$_2$ | Bz | oil | C$_{46}$H$_{59}$NO$_5$ | | | | N.O. | | |
| 55f | (CH$_2$)$_2$O-2-Naphthyl | Bz | 95–97 | C$_{44}$H$_{59}$NO$_5$ | 77.50 | 8.72 | 2.05 | 77.66 | 8.84 | 2.06 |
| 55g | (CH$_2$)$_2$O-3-Pyridyl | Bz | 65–67 | C$_{40}$H$_{58}$N$_2$O$_5$ | | | | N.O. | | |
| 55h | (CH$_2$)$_3$OC$_6$H$_4$-3-OCH$_3$ | Bz | 58–60 | C$_{42}$H$_{61}$NO$_5$ | | | | N.O. | | |
| 55i | (CH$_2$)$_3$OC$_6$H$_4$-4-OCH$_3$ | Bz | 70–71 | C$_{42}$H$_{61}$NO$_5$ | | | | N.O. | | |
| 55j | (CH$_2$)$_3$OC$_6$H$_4$-4-OBz | tBu | 90–92 | C$_{45}$H$_{67}$NO$_6$ | | | | N.O. | | |
| 55k | (CH$_2$)$_3$OC$_6$H$_4$-3-NO$_2$ | tBu | 98–100 | C$_{38}$H$_{60}$N$_2$O$_7$ | | | | N.O. | | |
| 55l | (CH$_2$)$_3$OC$_6$H$_4$-4-COOCH$_3$ | Bz | 63–67 | C$_{43}$H$_{61}$NO$_7$ | | | | N.O. | | |

*Not Obtained

EXAMPLE 56

3-(Octadecyloxy)-5-(3-phenoxypropoxy)benzenamine

A mixture of 10.9 g of 3-(octadecyloxy)-5-(3-phenoxypropoxy)phenylcarbamic acid phenylmethyl ester and 1.2 g of 10% palladium on carbon in 200 ml of THF and 50 ml of ethyl acetate was stirred under a hydrogen atmosphere at room temperature for 17 hours. The catalyst was removed by filtration and the filtrate was concentrated to a solid which was recrystallized from ethyl acetate-hexane to give 8.0 g (92% yield, mp 74°–76°) of 3-(octadecyloxy)-5-(3-phenoxypropoxy)benzenamine. The structure was confirmed by nmr and mass spectra.

The compounds in Table 17 were prepared using the procedure of Example 56 if the precursor was a benzyl ester or the procedure of Example 91 if the precursor was a t-butylester.

TABLE 17

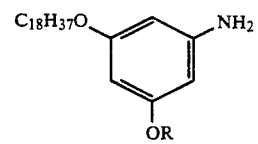

| Ex. | R | mp (°C.) | E.F. | Calcd C | Calcd H | Calcd N | Found C | Found H | Found N |
|---|---|---|---|---|---|---|---|---|---|
| 56a | (CH$_2$)$_2$OAc | 79–80 | C$_{28}$H$_{49}$NO$_4$ | | | | N.O. | | |
| 56b | CH$_2$COOCH$_3$ | 69–71 | C$_{27}$H$_{47}$NO$_4$ | | | | N.O. | | |
| 56c | (CH$_2$)$_{10}$COOCH$_3$ | 44–45 | C$_{36}$H$_{65}$NO$_4$ | 75.03 | 11.38 | 2.43 | 75.31 | 11.31 | 2.28 |
| 56d | CO-1-Adamantyl | 80–81 | C$_{35}$H$_{57}$NO$_3$ | 77.87 | 10.64 | 2.59 | 77.17 | 10.47 | 2.46 |
| 56e | COCH(C$_6$H$_5$)$_2$ | 62–63 | C$_{38}$H$_{53}$NO$_3$ | 79.82 | 9.34 | 2.45 | 79.98 | 9.56 | 2.33 |
| 56f | (CH$_2$)$_2$O-2-Naphthyl | 100–102 | C$_{36}$H$_{53}$NO$_3$ | 78.93 | 9.75 | 2.56 | 78.71 | 9.77 | 2.50 |
| 56g | (CH$_2$)$_2$O-3-Pyridyl | 64–68 | C$_{32}$H$_{52}$N$_2$O$_3$ | 74.96 | 10.22 | 5.46 | 74.80 | 10.27 | 5.38 |
| 56h | (CH$_2$)$_3$OC$_6$H$_4$-3-OCH$_3$ | 52–53 | C$_{34}$H$_{55}$NO$_4$ | 75.37 | 10.23 | 2.59 | 75.22 | 10.51 | 2.50 |
| 56i | (CH$_2$)$_3$OC$_6$H$_4$-4-OCH$_3$ | 64–66 | C$_{34}$H$_{55}$NO$_4$ | 75.37 | 10.23 | 2.59 | 75.43 | 10.26 | 2.57 |
| 56j | (CH$_2$)$_3$OC$_6$H$_4$-4-OBz | 80–82 | C$_{40}$H$_{59}$NO$_4$ | | | | N.O. | | |
| 56k | (CH$_2$)$_3$OC$_6$H$_4$-3-NO$_2$ | 81–83 | C$_{33}$H$_{52}$N$_2$O$_5$ | | | | N.O. | | |
| 56l | (CH$_2$)$_3$OC$_6$H$_4$-4-COOCH$_3$ | 78–79 | C$_{35}$H$_{55}$NO$_5$ | 73.77 | 9.73 | 2.46 | 73.15 | 9.76 | 2.32 |
| 56m | (CH$_2$)$_2$O(CH$_2$)$_2$O(CH$_2$)$_2$OC$_2$H$_5$ | oil | C$_{32}$H$_{59}$NO$_5$ | | | | N.O. | | |

*Not Obtained

EXAMPLE 57

N-[3-(Octadecyloxy)-5-(3-phenoxypropoxy)phenyl]-N-[2-oxo-2-(phenylmethoxy)ethyl]glycine phenylmethyl ester A mixture of 8.0 g (0.016 mol) of 3-(octadecyloxy)-5-(3-phenoxypropoxy)benzenamine, 25 ml (0.157 mol) of benzylbromoacetate, 8.4 g (0.04 mol) of 1,8-bis(dimethylamino) naphthalene and 1.2 g (0.008 mol) of sodium iodide in 400 ml of acetonitrile was heated at reflux for 48 hours. The solvent was removed at reduced pressure and the residue was dissolved in ethyl acetate. The extract was washed with 0.05N HCl, with NaHCO$_3$ solution, dried and concentrated to an oil which was purified by HPLC using 12.5% ethyl acetate-hexane to give 7.4 g (59% yield, mp 59°–61°) of N-[3-(octadecyloxy)-5-(3-phenoxypropoxy)phenyl]-N-[2-oxo-2-(phenylmethoxy)ethyl]glycine phenylmethyl ester. The structure was confirmed by nmr and mass spectra.

The compounds in Table 18 were prepared by the procedure of Example 57 using benzyl bromoacetate or methyl bromoacetate.

99°–102°) of N-(carboxymethyl)-N-[3-(octadecyloxy)-5-(3-phenoxypropoxy)phenyl]glycine.

Anal. Calcd for $C_{37}H_{57}NO_7$: C, 70.78; H, 9.15; N,

TABLE 18

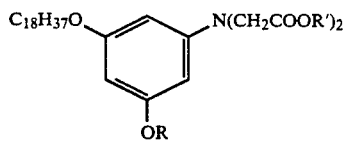

| Ex. | R | R' | mp (°C.) | E.F. | Calcd C | Calcd H | Calcd N | Found C | Found H | Found N |
|---|---|---|---|---|---|---|---|---|---|---|
| 57a | $(CH_2)_2OAc$ | $CH_3$ | 64–66 | $C_{34}H_{57}NO_8$ | | | | N.O.* | | |
| 57b | $(CH_2)COOCH_3$ | Bz | 72–74 | $C_{45}H_{63}NO_8$ | 72.45 | 8.51 | 1.88 | 72.21 | 8.83 | 1.95 |
| 57c | $(CH_2)_4COOCH_3$ | Bz | 48–50 | $C_{48}H_{69}NO_8$ | | | | N.O | | |
| 57d | CO-1-Adamantyl | Bz | oil | $C_{53}H_{73}NO_7$ | | | | N.O. | | |
| 57e | $COCH(C_6H_5)_2$ | Bz | oil | $C_{56}H_{59}NO_7$ | | | | N.O. | | |
| 57f | $(CH_2)_2O$-2-Naphthyl | Bz | 68–71 | $C_{54}H_{69}NO_7$ | 76.83 | 8.24 | 1.66 | 76.78 | 8.36 | 1.56 |
| 57g | $(CH_2)_3O$-3-Pyridyl | Bz | oil | $C_{50}H_{68}N_2O_7$ | | | | N.O. | | |
| 57h | $(CH_2)_3OC_6H_4$-3-$OCH_3$ | Bz | 58–61 | $C_{52}H_{71}NO_8$ | 74.52 | 8.54 | 1.67 | 74.30 | 8.41 | 1.74 |
| 57i | $(CH_2)_3OC_6H_4$-4-$OCH_3$ | Bz | 50–52 | $C_{52}H_{71}NO_8$ | | | | N.O. | | |
| 57j | $(CH_2)_3OC_6H_4$-4-OBz | Bz | 59–61 | $C_{58}H_{75}NO_8$ | | | | N.O. | | |
| 57k | $(CH_2)_3OC_6H_4$-3-$NO_2$ | $CH_3$ | 70–71 | $C_{39}H_{60}N_2O_9$ | | | | N.O. | | |
| 57l | $(CH_2)_3OC_6H_4$-4-$COOCH_3$ | Bz | 75–78 | $C_{53}H_{71}NO_9$ | 73.50 | 8.26 | 1.62 | 73.81 | 8.44 | 1.73 |
| 57m | $(CH_2)_2O(CH_2)_2O(CH_2)_2OC_2H_5$ | $CH_3$ | oil | $C_{38}H_{67}NO_9$ | 66.93 | 9.90 | 2.05 | 66.76 | 10.20 | 1.97 |

*Not Obtained

EXAMPLE 58

N-(Carboxymethyl)-N-[3-(octadecyloxy)-5-(3-phenoxypropoxy)phenyl]glycine

A mixture of 7.4 g of N-[3-(octadecyloxy)-5-(3-phenoxypropoxy)phenyl]-N-2-(phenylmethoxy)-2-oxoethyl]glycine phenylmethyl ester and 1.8 g of 10% palladium on carbon in 100 ml of THF and 100 ml of ethyl acetate was shaken under a hydrogen atmosphere at room temperature for 3.5 hours. The catalyst was removed by filtration and the filtrate was concentrated at reduced pressure to a solid which was triturated with ether-hexane and filtered to give 5.35 g (93% yield, mp 2.23. Found: C, 70.93; H, 9.30; N, 2.24.

The compounds in Table 19 were prepared using the procedure of Example 58, if the precursor was a benzyl ester, or base hydrolysis using sodium hydroxide if the precursor was a methyl ester.

TABLE 19

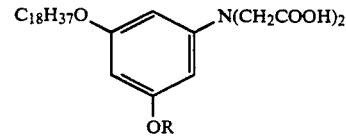

| Ex. | R | mp (°C.) | E.F. | Calcd C | Calcd H | Calcd N | Found C | Found H | Found N |
|---|---|---|---|---|---|---|---|---|---|
| 58a | $(CH_2)_2OH$ | 136–138 | $C_{30}H_{51}NO_7$ | 67.01 | 9.57 | 2.60 | 67.32 | 9.23 | 2.58 |
| 58b | $CH_2COOCH_3$ | 110–113 | $C_{31}H_{51}NO_8$ | 65.81 | 9.09 | 2.48 | 65.48 | 8.73 | 2.44 |
| 58c | $CH_2COOH$ | 160–190 | $C_{30}H_{49}NO_8$ | 65.31 | 8.95 | 2.54 | 64.96 | 8.67 | 2.55 |
| 58d | $(CH_2)_{10}COOCH_3$ | 42–45 | $C_{40}H_{69}NO_8$ | | | | N.O.* | | |
| 58e | $(CH_2)_{10}COOH$ | 43–45 | $C_{39}H_{67}NO_8$ | | | | N.O. | | |
| 58f | CO-1-Adamantyl | foam | $C_{39}H_{61}NO_7$ | | | | N.O. | | |
| 58g | $COCH(C_6H_5)_2$ | 105–108 | $C_{42}H_{57}NO_7$ | | | | N.O. | | |
| 58h | $(CH_2)_2O$-2-Naphthyl | 126–129 | $C_{40}H_{57}NO_7$ | 72.37 | 8.65 | 2.11 | 71.62 | 8.65 | 2.01 |
| 58i | $(CH_2)_3O$-3-Pyridyl | 118–121 | $C_{36}H_{56}N_2O_7$ | 68.76 | 8.98 | 4.45 | 67.05 | 8.91 | 4.31 |
| 58j | $(CH_2)_3OC_6H_4$-3-$OCH_3$ | 78–82 | $C_{38}H_{59}NO_8$ | 69.38 | 9.04 | 2.13 | 69.38 | 9.24 | 2.05 |
| 58k | $(CH_2)_3OC_6H_4$-4-$OCH_3$ | 127–129 | $C_{38}H_{59}NO_8$ | 69.38 | 9.04 | 2.13 | 69.09 | 8.91 | 2.09 |
| 58l | $(CH_2)_3OC_6H_4$-4-OH | 142–144 | $C_{37}H_{57}NO_8$ | 69.02 | 8.92 | 2.18 | 68.78 | 8.74 | 2.13 |
| 58m | $(CH_2)_3OC_6H_4$-3-$NO_2$ | 87–89 | $C_{37}H_{56}N_2O_9$ 0.25 $H_2O$ | 65.61 $H_2O$ | 8.41 0.66 | 4.14 | 65.54 $H_2O$ | 8.35 0.52 | 4.13 |
| 58n | $(CH_2)_3OC_6H_4$-3-$NH_2$ | 155–157 | $C_{37}H_{58}N_2O_7$ | 69.13 | 9.09 | 4.36 | 68.60 | 9.31 | 4.19 |
| 58o | $(CH_2)_3OC_6H_4$-4-$COOCH_3$ | 143–146 | $C_{39}H_{59}NO_9$ | 68.29 | 8.67 | 2.04 | 68.00 | 8.91 | 1.92 |
| 58p | $(CH_2)_3OC_6H_4$-4-COOH | 135–136 | $C_{38}H_{57}NO_9$ | 67.93 | 8.55 | 2.08 | 68.00 | 8.62 | 1.97 |

*Not obtained

EXAMPLE 59

3-(Octadecyloxy)-5-[(5-methoxy-5-oxopentyl)oxy]benzoic acid phenylmethyl ester

A mixture of 10.0 g (0.02 mol) of 3-hydroxy-5-(octadecyloxy)benzoic acid phenylmethyl ester, 4.3 ml (0.03 mol) of methyl 5-bromovalerate, 5.6 (0.04 mol) of potassium carbonate and 3.0 g (0.02 mol) of sodium iodide in 300 ml of acetone and 75 ml of DMF was stirred at reflux under argon for 40 hours. The reaction mixture was filtered and the filtrate was concentrated at reduced pressure to a solid which was recrystallized from methylene chloride-methanol to give 11.3 g (92% yield, mp 40°-42°) of 3-(octadecyloxy)-5-[(5-methoxy-5-oxopentyl)oxy]benzoic acid phenylmethyl ester. The structure was confirmed by nmr and mass spectra.

EXAMPLE 60

3-(Octadecyloxy)-5-[(5-methoxy-5-oxopentyl)oxy]benzoic acid

A mixture of 11.3 g of 3-(octadecyloxy)-5-[(5-methoxy-5-oxopentyl)oxy]benzoic acid phenylmethyl ester and 1.5 g of 10% palladium on carbon in 250 ml of THF was stirred in a hydrogen atmosphere at room temperature for 4 hours. The catalyst was removed by filtration and the filtrate was concentrated at reduced pressure to a solid which was triturated with hexane and filtered to give 9.37 g (98% yield, mp 68°-70°) of 3-(octadecyloxy)-5-[(5-methoxy-5-oxopentyl)oxy]benzoic acid.

Anal. Calcd for $C_{31}H_{52}O_6$: C, 71.50; H, 10.07. Found: C, 71.17; H, 10.21.

EXAMPLE 61

3-(Octadecyloxy)-5-[(5-methoxy-5-oxopentyl)oxy]pentyl]carbamic acid phenylmethyl ester To a stirred solution of 9.37 g (0.018 mol) of 3-(octadecyloxy)-5-[(5-methoxy-5-oxopentyl)oxy]benzoic acid in 200 ml of anhydrous toluene stirred with ice bath cooling under an argon atmosphere was added 4.7 ml (0.021 mol) of diphenylphosphoryl azide followed by 3.0 ml (0.021 mol) of triethylamine added dropwise over 15 minutes. The reaction mixture was stirred in the ice bath for 2 hours and then was heated at 90° for 2 hours. Benzyl alcohol (65 ml) was added and heating at 90° was continued for 4 hours. The solvent and excess benzyl alcohol were removed at reduced pressure and the residue was dissolved in ethyl acetate. The extract was washed with NaHCO₃ solution, dried and concentrated at reduced pressure to a solid. Purification by chromatography on 150 g of silica gel using methylene chloride gave 8.9 g (79% yield, mp 59°-62°) of 3-(octadecyloxy)-5-[(5-methoxy-5-oxopentyl)oxy]phenylcarbamic acid phenylmethyl ester. The structure was confirmed by the nmr spectrum.

EXAMPLE 62

5-[3-Amino-5-(octadecyloxy)phenoxy]pentanoic acid methyl ester

A mixture of 8.9 g of 3-(octadecyloxy)-5-[(5-methoxy-5-oxopentyl)oxy]phenylcarbamic acid phenylmethyl ester and 1.5 g of 10% palladium on carbon in 250 ml of THF was stirred in a hydrogen atmosphere at room temperature for 2.5 hours. The catalyst was removed by filtration and the filtrate was concentrated at reduced pressure to a solid which was triturated with hexane and filtered to give 6.8 g (97% yield, mp 57°-59°) of 5-[3-amino-5(octadecyloxy)phenoxy]pentanoic acid methyl ester.

Anal. Calcd for $C_{30}H_{53}NO_4$: C, 73.27; H, 10.86; N, 2.85. Found: C, 72.86; H, 10.77; N, 2.95.

EXAMPLE 63

N-[3-(Octadecyloxy)-5-[(5-methoxy-5-oxopentyl)oxy]phenyl]-N-[2-oxo-2-(phenylmethoxy)ethyl]glycine phenylmethyl ester A mixture of 6.77 g (13.8 mmol) of 5-[3-amino-5-(octadecyloxy)phenoxy]pentanoic acid methyl ester, 6.6 ml (41.3 mmol) of benzyl bromoacetate, 7.4 g (34.4 mmol) of 1,8-bis(dimethylamino)naphthalene and 0.6 g (3.9 mmol) of sodium iodide in 150 ml of acetonitrile and 50 ml of DMF was stirred at reflux under an argon atmosphere for 48 hours. The reaction mixture was concentrated at reduced pressure to remove the solvents and ethyl acetate was added to the residue. The extract was washed with 0.5N HCl, with NaHCO₃ solution, dried and concentrated at reduced pressure to an oil. Purification by HPLC using 20% ethyl acetate-hexane gave 6.55 g (60% yield, mp 48°-50°) of N-[3-(octadecyloxy)-5-[(5-methoxy-5-oxopentyl)oxy]phenyl]-N-[2-oxo-2-(phenylmethoxy)ethyl]glycine phenylmethyl ester.

Anal. Calcd for $C_{48}H_{69}NO_8$: C, 73.16; H, 8.83; N, 1.78. C, 73.02; H, 8.91; N, 1.75.

EXAMPLE 64

N-(Carboxymethyl)-N-[3-octadecyloxy)-5-[(5-methoxy-5-oxopentyl)oxy]phenyl]glycine A mixture of 6.5 g of N-[3-(octadecyloxy)-5-[(5-methoxy-5-oxopentyl)oxy]phenyl]-N-[2-(phenylmethoxy)-2-oxoethyl]glycine phenylmethyl ester and 1.5 g of 10% palladium on carbon in 200 ml of THF was stirred in a hydrogen atmosphere at room temperature for 2.5 hours. The catalyst was removed by filtration and the filtrate was concentrated at reduced pressure to a solid which was triturated with hexane. Filtration gave 4.73 g (94% yield, mp 91°-94°) of N-(carboxymethyl)-N-[3-(octadecyloxy)-5-[(5-methoxy-5-oxopentyl)oxy]phenyl]glycine.

Anal. Calcd for $C_{35}H_{57}NO_8$: C, 67.19; H, 9.45; N, 2.30. Found: C, 67.02; H, 9.41; N, 2.19.

EXAMPLE 65

N-[3-(4-Carboxybutoxy)-5-(octadecyloxy)phenyl]-N-(carboxymethyl)glycine

A solution of 2.0 g (3.3 mmol) of N-(carboxymethyl)-N-[3-(octadecyloxy)-5-[(5-methoxy-5-oxopentyl)oxy]phenyl]glycine and 2.8 ml (16.5 mmol) of 6N NaOH in 100 ml of methanol was stirred at reflux under argon for 16 hours. After cooling to room temperature, the precipitated sodium salt was removed by filtration, dissolved in 300 ml of water and the mixture was acidified with 4 ml of 6N HCl. The product was extracted with ethyl acetate and the dried extract was concentrated at reduced pressure to a solid which was recrystallized from acetone-hexane to give 1.8 g (92% yield, mp 126°-128°) of N-[3-(4-carboxybutoxy)-5-(octadecyloxy)phenyl]-N-(carboxymethyl)glycine.

Anal. Calcd for $C_{33}H_{55}NO_8$: C, 66.75; H, 9.34; N, 2.36. Found: C, 66.90; H, 9.61; N, 2.33.

EXAMPLE 66

3-Nitro-5-(octadecyloxy)benzoic acid methyl ester

A mixture of 1.7 g (8.6 mmol) of 3-hydroxy-5-nitrobenzoic acid methyl ester [prepared as described by D. J. Abraham, D. M. Gazze, P. E. Kennedy and M. Mokotoff, J. Med. Chem. 27, 1549 (1984], 3.2 g (9.5 mmol) of 1-bromooctadecane and 1.8 g (12.9 mmol) of potassium carbonate in 35 ml of anhydrous DMF was stirred and heated at 75° for 25 hours. After cooling, 150 ml of methylene chloride was added and the insoluble salts were removed by filtration. The filtrate was concentrated at reduced pressure to a solid which was purified by HPLC using 30% methylene chloride-hexane to give 3.57 g (92% yield, mp 64°-66°) of 3-nitro-5-(octadecyloxy)benzoic acid methyl ester.

Anal. Calcd for $C_{26}H_{43}NO_5$: C, 69.45; H, 9.64; N, 3.12. Found: C, 69.39; H, 9.66; N, 3.04.

The compounds in Table 20 were prepared using the procedure of Example 66.

TABLE 20

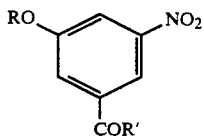

| | | | | | Microanalytical Data | | | | | |
|---|---|---|---|---|---|---|---|---|---|---|
| | | | | | Calcd | | | Found | | |
| Ex. | R | R' | mp (°C.) | E.F. | C | H | N | C | H | N |
| 66a | $C_{14}H_{29}$ | $OCH_3$ | 50-53 | $C_{22}H_{35}NO_5$ | | | | N.O. | | |
| 66b | $C_{10}H_{21}$ | $OCH_3$ | 42-44 | $C_{18}H_{27}NO_5$ | | | | N.O. | | |

*Not Obtained

The compounds in Table 21 were prepared using the procedure of Example 67.

TABLE 21

| | | | | | Microanalytical Data | | | | | |
|---|---|---|---|---|---|---|---|---|---|---|
| | | | | | Calcd | | | Found | | |
| Ex. | R | R' | mp (°C.) | E.F. | C | H | N | C | H | N |
| 67a | $C_{14}H_{29}$ | $OCH_3$ | 84-87 | $C_{22}H_{37}NO_3$ | | | | N.O. | | |
| 67b | $C_{10}H_{21}$ | $OCH_3$ | 77-79 | $C_{18}H_{29}NO_3$ | | | | N.O. | | |

*Not Obtained

EXAMPLE 68

N-[3-(Methoxycarbonyl)-5-(octadecyloxy)phenyl]-N-[2-oxo-2-(phenylmethoxy)ethyl]glycine phenylmethyl ester A mixture of 3.25 g (7.74 mmol) of 3-amino-5-(octadecyloxy)benzoic acid methyl ester, 3.7 ml (23 mmol) of benzyl bromoacetate, 4.2 g (19.4 mmol) of 1,8-bis(dimethylamino)naphthalene and 0.3 g (2.2 mmol) of sodium iodide in 65 ml of acetonitrile and 20 ml of DMF was stirred and heated at reflux under argon for 48 hours. The reaction mixture was concentrated at reduced pressure and ethyl acetate was added to the residue. The extract was washed with 0.05N HCl, with saturated $NaHCO_3$ solution, dried and concentrated at reduced pressure to a solid which was purified by HPLC using 15% ethyl acetate-hexane to give 2.6 g (48% yield, mp 62°-63°) of N-[3-(methoxycarbonyl)-5-(octadecyloxy)phenyl]-N-[2-oxo-2-(phenylmethoxy)ethyl]glycine phenylmethyl ester.

Ana. Calcd for $C_{44}H_{61}NO_7$: C, 73.81; H, 8.59; N, 1.96. Found: C, 73.46; H, 8.69; N, 2.01.

The compounds in Table 22 were prepared using the procedure of Example 68.

EXAMPLE 67

3-Amino-5-(octadecyloxy)benzoic acid methyl ester

A mixture of 3.55 g of 3-nitro-5-(octadecyloxy)benzoic acid methyl ester and 0.75 g of 10% palladium on carbon in 100 ml of THF was shaken under an initial hydrogen pressure of 52 psi until uptake ceased after 1.5 hours. The catalyst was removed by filtration and the filtrate was concentrated at reduced pressure to give 3.28 g of pure 3-amino-5-(octadecyloxy)benzoic acid methyl ester.

Ana. Calcd for $C_{26}H_{45}NO_3$: C, 74.43; H, 10.81; N, 3.34. Found: C, 74.10; H, 10.90; N, 3.04.

TABLE 22

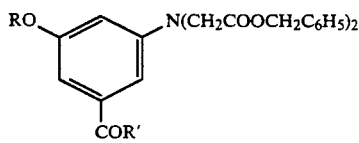

| Ex. | R | R' | mp (°C.) | E.F. | Microanalytical Data Calcd C H N | Found C H N |
|---|---|---|---|---|---|---|
| 68b | C₁₄H₂₉ | OCH₃ | 52–54 | C₄₀H₅₃NO₇ | *N.O. | |
| 68c | C₁₀H₂₁ | OCH₃ | oil | C₃₆H₄₅NO₇ | N.O. | |

*Not obtained

EXAMPLE 69

N-(Carboxymethyl)-N-[3-(methoxycarbonyl)-5-(octadecyloxy)phenyl]glycine

A mixture of 2.63 g (3.67 mmol) of N-[3-(methoxycarbonyl)-5-(octadecyloxy)phenyl]-N-[2-(phenylmethoxy)-2-oxoethyl]glycine phenylmethyl ester and 0.5 g of 10% palladium on carbon in 150 ml of THF was shaken in a hydrogen atmosphere at room temperature for 3 hours. The catalyst was removed by filtration and the filtrate was concentrated to a solid which was recrystallized from methanol-water to give 1.84 g (93% yield, mp 119°–123°) of N-(carboxymethyl)-N-[3-(methoxycarbonyl)-5-(octadecyloxy)phenyl]glycine.

Ana. Calcd for C₃₀H₄₉NO₇: C, 67.26; H, 9.22; N, 2.61. Found: C, 67.35; H, 9.57; N, 2.53.

Compounds 69a and c in Table 23 were prepared using the procedure of Example 69. Compounds 69b and d were prepared by base hydrolysis of 69a and c respectively, as in Example 70.

TABLE 23

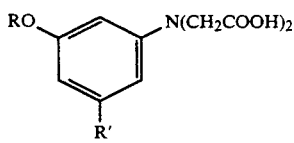

| Ex. | R | R' | mp (°C.) | E.F. | Microanalytical Data Calcd C H N | | | Found C H N | | |
|---|---|---|---|---|---|---|---|---|---|---|
| 69a | C₁₄H₂₉ | COOCH₃ | 121–124 | C₂₆H₄₁NO₇ | 65.11 | 8.62 | 2.92 | 65.15 | 8.75 | 2.90 |
| 69b | C₁₄H₂₉ | COOH | 153–156 | C₂₅H₃₉NO₇ 0.25 H₂O | 63.88 H₂O | 8.47 0.96 | 2.98 | 64.55 H₂O | 8.39 1.12 | 2.70 |
| 69c | C₁₀H₂₁ | COOCH₃ | 126–128 | C₂₂H₃₃NO₇ | 62.39 | 7.85 | 3.31 | 62.12 | 7.80 | 3.26 |
| 69d | C₁₀H₂₁ | COOH | 160–162 | C₂₁H₃₁NO₇ 0.25 H₂O | 60.93 H₂O | 7.67 1.09 | 3.38 | 61.06 H₂O | 261 0.94 | 3.29 |

EXAMPLE 70

N-[3-Carboxy-5-(octadecyloxy)phenyl]-N-(carboxymethyl)glycine

A solution of 1.0 g (1.87 mmol) of N-(carboxymethyl)-N-[3(methoxycarbonyl)-5-(octadecyloxy)phenyl]glycine and 3.1 ml (9.35 mmol) of 3N NaOH in 100 ml of methanol was stirred at reflux under argon for 48 hours. The warm solution was acidified with 3N HCl to pH 2 and the methanol was removed at reduced pressure. Water was added and the product was filtered and recrystallized from methanol-water to give 0.78 g (80% yield, mp 149°–155°) of N-[3-carboxy-5-(octadecyloxy)phenyl]-N-(carboxymethyl)glycine as a hydrate with 0.75 mole of water.

Ana. Calcd for C₂₉H₄₇NO₇. 0.75 H₂O: C, 65.08; H, 9.13; N, 2.62; H₂O, 2.52. Found: C, 6455; H, 9.01; N, 2.57; H₂O, 2.38.

EXAMPLE 71

3-Nitro-5-(octadecyloxy)benzoic acid

A solution of 4.5 g of 3-nitro-5-(octadecyloxy)benzoic acid methyl ester and 4 ml of 6N NaOH in 200 ml of methanol and 50 ml of dioxane was stirred at reflux for 2.5 hours. The solvents were removed at reduced pressure and the residue was acidified with 1N HCl. The solid was filtered and recrystallized from methanol-water to give 2.7 g (62% yield, mp 101°–103°) of 3-nitro-5-(octadecyloxy)benzoic acid.

Ana. Calcd for C₂₅H₄₁NO₅: C, 68.93; H, 9.49; N, 3.22. Found: C, 67.94; H, 9.55; N, 3.02.

EXAMPLE 72

3-Nitro-5-(octadecyloxy)benzamide

A solution of 5.0 g of 3-nitro-5-(octadecyloxy)benzoic acid in 50 ml of thionyl chloride was refluxed for 3 hours. The excess thionyl chloride was removed at reduced pressure and the resultant solid acid chloride was dissolved in 100 ml of methylene chloride. Ammonia gas was bubbled through the solution for 10 minutes and the reaction mixture was left at room temperature for 1 hour. The solvent was removed at reduced pressure and the solid residue was triturated with THF and the product was removed by filtration to give 4.75 g, mp 117°–120°, of 3-nitro-5-(octadecyloxy)benzamide. The structure was confirmed by nmr and mass spectra.

EXAMPLE 73

3-Amino-5-(octadecyloxy)benzamide

A mixture of 4.75 g of 3-nitro-5-(octadecyloxy)benzamide and 1.0 g of 10% palladium on carbon in 750 ml of THF was shaken in a hydrogen atmosphere at room temperature until uptake ceased after 4 hours. The catalyst was removed by filtration and the filtrate was concentrated at reduced pressure to a solid which was recrystallized from methanol to give 4.0 g (91% yield, mp 139°-143°) of 3-amino-5-(octadecyloxy)benzamide.

Ana. Calcd for $C_{25}H_{44}N_2O_2$: C, 74.21; H, 10.96; N, 6.92. Found: C, 74.12; H, 11.07; N, 6.81.

EXAMPLE 74

N-[(3-Carbamoyl)-5-(octadecyloxy)phenyl]-N-[2-oxo-2-(phenylmethoxy)ethyl]glycine phenylmethyl ester A mixture of 3.0 g (7.4 mmol) of 3-amino-5-(octadecyloxy)benzamide, 3.6 ml (22 mmol) of benzyl bromoacetate, 4.0 g (18.5 mmol) of 1,8-bis(dimethylamino)naphthalene and 0.3 g (2.1 mmol) of sodium iodide in 60 ml of acetonitrile and 20 ml of DMF was stirred and heated at reflux under argon for 48 hours. The solvents were removed at reduced pressure and the residue was dissolved in ethyl acetate. The extract was washed with 0.05N HCl, with NaHCO$_3$ solution, dried and concentrated at reduced pressure to a solid. Purification by HPLC using 20% ethyl acetate-toluene gave 2.24 g (43% yield, mp 112°-114°) of N-[(3-carbamoyl)-5-(octadecyloxy)phenyl]-N-[2-oxo-2-(phenylmethoxy)ethyl]glycine phenylmethyl ester.

Anal. Calcd for $C_{43}H_{60}N_2O_6$: C, 73.68; H, 8.63; N, 4.00. Found: C, 73.69; H, 8.64; N, 3.90.

EXAMPLE 75

N-(Carboxymethyl)-N-[(3-carbamoyl)-5-(octadecyloxy)phenyl]glycine

A mixture of 2.2 g of N-[(3-carbamoyl)-5-(octadecyloxy)phenyl-N-[2-(phenylmethoxy)-2-oxoethyl]glycine phenylmethyl ester and 0.5 g of 10% palladium on carbon in 100 ml of THF was stirred in a hydrogen atmosphere at room temperature until uptake ceased after 3 hours. DMF (150 ml) was added and the mixture was heated to dissolve the precipitated product. The hot mixture was filtered to remove the catalyst and the filtrate was concentrated at reduced pressure to a solid. Recrystallization from THF gave 1.1 g (69% yield, mp 213°-216°) of N-(carboxymethyl)-N-[(3-carbamoyl)-5-(octadecyloxy)phenyl]glycine.

Ana. Calcd for $C_{29}H_{48}N_2O_6$: C, 66.89; H, 9.29; N, 5.38. Found: C, 66.58; H, 9.30; N, 5.19.

EXAMPLE 76

3-Acetyloxy-5-(octadecyloxy)benzenecarboxylic acid

To a stirred and ice bath cooled solution of 5.0 g (0.01 mol) of 3-hydroxy-5-(octadecyloxy)benzoic acid phenylmethyl ester in 7.5 ml of methylene chloride and 2.8 ml (0.02 mol) of triethylamine was added 0.86 ml (0.012 mol of acetyl chloride. The reaction mixture was stirred in an ice bath for 1 hour, at room temperature for 2 hours and then was washed with 1N HCl, with NaHCO$_3$ solution, dried and concentrated at reduced pressure to a solid. Trituration with methanol and filtration gave 5.17 g (96% yield, mp 55°-56°) of 3-acetyloxy-5-(octadecyloxy)benzenecarboxylic acid.

Ana. Calcd for $C_{27}H_{44}O_5$: C, 72.28; H, 9.89. Found: C, 72.16; H, 9.79.

EXAMPLE 77

3-Acetyloxy-5-(octadecyloxy)phenylcarbamic acid phenylmethyl ester

To a solution of 3.0 g (6.7 mmol) of 3-acetyloxy-5-(octadecyloxy)benzenecarboxylic acid in 70 ml of dry toluene and 10 ml of dry DMF cooled in an ice bath was added 1.7 ml (8 mmol) of diphenylphosphoryl azide followed by 1.1 ml (8 mmol) of triethylamine. The reaction mixture was stirred in the ice bath for 1.5 hours and then was heated at 90° for 5 hours. Benzyl alcohol (20 ml) was added and heating at 90° was continued for 16 hours. The solvents were removed at reduced pressure and ethyl acetate was added to the residue. The extract was washed with NaHCO$_3$ solution and then cooled at −18°. The precipitate was removed by filtration and the filtrate was concentrated at reduced pressure to an oil which was purified by chromatography on 150 g of silica gel using 25% ethyl acetate-hexane to give 1.87 g (50% yield, mp 57°-59°) of 3-acetyloxy-5-(octadecyloxy)phenylcarbamic acid phenylmethyl ester.

Ana. Calcd for $C_{34}H_{51}NO_5$: C, 73.34; H, 9.28; N, 2.53. Found: C, 73.53; H, 9.26; N, 2.45.

EXAMPLE 78

3-Acetyloxy-5-(octadecyloxy)benzenamine

A mixture of 1.87 g of 3-acetyloxy-5-(octadecyloxy)phenylcarbamic acid phenylmethyl ester and 1 g of 10% palladium on carbon in 100 ml of THF was shaken under an initial hydrogen pressure of 53 psi until uptake ceased after 16 hours. The catalyst was removed by filtration and the filtrate was concentrated at reduced pressure to give 1.26 g, mp 73°-74°, of pure 3-acetyloxy-5-(octadecyloxy)benzenamine.

Ana. Calcd for $C_{26}H_{45}NO_3$: C, 74.42; H, 10.81; N, 3.34. Found: C, 74.53; H, 10.48; N, 3.19.

EXAMPLE 79

N-[(3-Acetyloxy)-5-(octadecyloxy)phenyl]-N-[2-oxo-2-(phenylmethoxy)ethyl]glycine phenylmethyl ester A mixture of 1.26 g (0.03 mol) of 3-acetyloxy-5-(octadecyloxy)benzene amine, 2.4 ml (0.015 mol) of benzyl bromoacetate 2.1 g (0.01 mol) of 1,8-bis(dimethylamino)naphthalene and 0.45 g (0.003 mol) of sodium iodide in 75 mo of acetronitrile was stirred at reflux for 114 hours. The solvent was removed at reduced pressure and ethyl acetate was added to the residue. The extract was washed with 1N HCl, with NaHCO$_3$ solution, dried and concentrated to a solid which was purified by chromatography on 150 g of silica gel using 17% ethyl acetate to give 1.0 g, mp 52°-53°, of N-[(3-acetyloxy)-5-(octadecyloxy)phenyl]-N-[2-oxo-2-(phenylmethoxy)-ethyl]glycine phenylmethyl ester. The structure was confirmed by nmr and mass spectra.

EXAMPLE 80

N-[3-(Acetyloxy)-5-(octadecyloxy)phenyl-N-(carboxymethyl)glycine

A mixture of 1.0 g of N-[(3-acetyloxy)-5-(octadecyloxy)phenyl]-N-[2-(phenylmethoxy)-2-oxoethyl]glycine phenylmethyl ester and 0.5 g of 10% palladium on carbon in 40 ml of ethyl acetate was shaken under an initial hydrogen pressure of 50 psi until uptake ceased after 2.5 hours. The mixture was heated to boiling and filtered hot to remove the catalyst from the precipitated product. The filtrate was concentrated at reduced pressure to give pure N-[3-(acetyloxy)-5-(octadecyloxy)-phenyl-N-(carboxymethyl)glycine, mp 122°–127°. The structure was confirmed by nmr and mass spectra.

EXAMPLE 81

N-(Carboxymethyl)-N-[3-hydroxy-5-(octadecyloxy)-phenyl]glycine

To solution of 1.0 g (1.87 mmol) of N-[3-(acetyloxy)-5-(octadecyloxy)phenyl-N-(carboxymethyl)glycine in 30 ml of dioxane and 70 ml of methanol was added 1.6 mol (9.6 mmol) of 6N NaOH The solution was kept at room temperature for 60 hours. The solvent was removed at reduced pressure and the residue wa acidified with 3N HCl. The resultant solid was filtered to give 0.546 g, mp 143°–146°, of pure N-carboxymethyl)-N-[3-hydroxy-5-(octadecyloxy)phenyl]glycine.

Ana. Calcd for $C_{28}H_{47}NO_6$: C, 68.12; H, 9.60; N, 2.84. Found: C, 67.96; H, 9.86; N, 2.34.

EXAMPLE 82

3-(3-Bromopropoxy)-5-(octadecyloxy)benzoic acid phenylmethyl ester

A mixture of 5.0 g (0.01 mol) of 3-hydroxy-5-(octadecyloxy)benzoic acid phenylmethyl ester, 10.2 ml (0.1 mol) of 1,3-dibromopropane and 7.0 g (0.05 mol) of potassium carbonate in 75 ml of acetone and 15 ml of DMF was stirred at reflux for 22 hours. The reaction mixture was filtered and the filtrate was concentrated at reduced pressure to an oil. Purification by HPLC using 5% ethyl acetate-hexane gave 4.91 g (79% yield, mp 57°–58°) of 3-(3-bromopropoxy)-5-(octadecyloxy)benzoic acid phenylmethyl ester. The structure was confirmed by the nmr spectrum.

EXAMPLE 83

3-[3-(Octadecyloxy)-5-(phenylmethoxycarbonyl)-phenoxy]propylphosphonic acid diethyl ester A mixture of 4.91 g (7.95 mmol) of 3-(3-bromopropoxy)-5-(octadecyloxy)benzoic acid phenylmethyl ester and 1.5 ml (8.74 mmol) of triethyl phosphite was stirred and heated at 150° for 32 hours. Purification by chromatography on 250 g of silica gel gave 3.2 g (60% yield) of 3-[3-(octadecyloxy)-5-(phenylmethoxycarbonyl)phenoxy]propylphosphonic acid diethyl ester as an oil. The structure was confirmed by the nmr spectrum.

EXAMPLE 84

3-[3-Carboxy-5-(octadecyloxy)phenoxy]propylphosphonic acid diethyl ester

A mixture of 3.2 g of 3-[3-(octadecyloxy)-5-(phenylmethoxycarbonyl)phenoxy]propylphosphonic acid diethyl ester and 0.5 g of 10% palladium on carbon in 100 ml of THF was stirred in a hydrogen atmosphere at room temperature for 2 hours. The catalyst was removed by filtration and the filtrate was concentrated at reduced pressure to give 2.65 g, mp 53°–55°, of 3-[3-carboxy-5-(octadecyloxy)phenoxy]propylphosphonic acid diethyl ester.

Anal. Calcd for $C_{32}H_{57}O_7P$: C, 65.73; H, 9.82; P, 5.30. Found: C, 65.85; H, 9.77; P, 5.18.

EXAMPLE 85

[3-[3-(Diethoxyphosphinyl)propoxy]-5-(octadecyloxy)-phenyl]carbamic acid phenylmethyl ester To 2.55 g (4.36 mmol) of 3-[3-carboxy-5-(octadecyloxy)phenoxy]propylphosphonic acid diethyl ester in 75 ml of toluene stirred and cooled in an ice bath was added 1.12 ml (5.23 mmol) of diphenylphosphoryl azide followed by 0.73 ml (5.23 mmol) of triethylamine added dropwise. After stirring in the ice bath for 2 hours, the reaction mixture was stirred and heated at 90° for 2 hours. Benzyl alcohol (16 ml) was added and heating at 90° was continued for 4 hours. The solvent and the excess benzyl alcohol were removed at reduced pressure and the residue was dissolved in ethyl acetate. The extract was washed with $NaHCO_3$ solution, dried and concentrated at reduced pressure to an oil which was purified by HPLC using 50% ethyl acetate-hexane to give 2.47 g (82% yield) of [3-[3-(diethoxyphosphinyl)propoxy]-5-(octadecyloxy)-phenyl]carbamic acid phenylmethyl ester as an oil. The structure was confirmed by nmr and mass spectra.

EXAMPLE 86

[3-[3-Amino-5-(octadecyloxy)phenoxy]propyl]phosphonic acid ethyl ester

A mixture of 2.47 g of [3-[3-(diethoxyphosphinyl)-propoxy]-5-(octadecyloxy)phenyl]carbamic acid phenylmethyl ester and 0.4 g of 10% palladium on carbon in 100 ml of THF was stirred in a hydrogen atmosphere at room temperature for 2.5 hours. The catalyst was removed by filtration and the filtrate was concentrated at reduced pressure to a solid which was recrystallized from ether-hexane to give 1.83 g (92% yield, mp 63°–65°) of [3-[3-amino-5-(octadecyloxy)phenoxy]-propyl]phosphonic acid diethyl ester. The structure was confirmed by nmr and mass spectra.

EXAMPLE 87

N-[3-[3-(Diethoxyphosphinyl)propoxy]-5-(octadecyloxy)phenyl]-N-[2-oxo-2-(phenylmethoxy)ethyl]glycine phenylmethyl ester A mixture of 1.82 g (3.27 mmol) of [3-[3-amino-5-(octadecyloxy)phenoxy]propyl]phosphonic acid diethyl ester, 1.6 ml (9.82 mmol) of benzyl bromoacetate, 1.8 g (8.19 mmol) of 1,8-bis-(dimethylamino)naphthalene and 0.14 g (0.92 mmol) of sodium iodide in 40 ml of acetonitrile and 15 ml of DMF was stirred at reflux in argon for 48 hours. The reaction mixture was concentrated at reduced pressure and the residue was dissolved in ethyl acetate. The extract was washed with 0.05N HCl, dried and concentrated a reduced pressure to an oil which was purified by HPLC using 55% ethyl acetate-hexane. This gave 2.41 g (86% yield) of N-[3-[3-(diethoxyphosphinyl)propoxy-5-(octadecyloxy)-phenyl]-N-[2-oxo-2-(phenylmethoxy)ethyl]glycine phenylmethyl ester as an oil. The structure was confirmed by nmr and mass spectra.

EXAMPLE 88

N-(Carboxymethyl)-N-[3-[3-(diethoxyphosphinyl)-propoxy]-5-(octadecyloxy)phenyl]glycine A mixture of 2.4 g of N-[3-[3-(diethoxyphosphinyl)-propoxy-5-(octadecyloxy)phenyl]-N-[2-oxo-2-(phenylmethoxy)ethyl]glycine phenylmethyl ester and 0.5 g of 10% palladium on carbon in 100 ml of THF was stirred in a hydrogen atmosphere at room temperature for 9 hours. The catalyst was removed by filtration and the filtrate was concentrated at reduced pressure to an oil which was dissolved in 25 ml of ether and cooled in an ice bath. Filtration of the solid which crystallized gave 1.14 g (60% yield, mp 92°–94°) of N-(carboxymethyl)-N-[3-[3-diethoxyphosphinyl)propoxy-5-(octadecyloxy)-phenyl]glycine.

Anal. Calcd for $C_{35}H_{62}NO_9P$: C, 62.57; H, 9.30; N, 2.08; P, 4.61. Found: C, 62.66; H, 9.46; N, 2.21; P, 4.32.

EXAMPLE 89

N-(Carboxymethyl)-N-[3-[3-(ethoxyphosphinyl)-propoxy]-5-(octadecyloxy)phenyl]glycine A solution of 0.226 g (0.336 mmol) of N-(carboxymethyl)-N-[3-[3-(diethoxyphosphinyl)propoxy-5-(octadecyloxy)phenyl]glycine and 1.5 ml (1.5 mmol) of 1N NaOH in 20 ml of DMSO was stirred at 100° under argon for 24 hours. After cooling to room temperature, the solid was removed by filtration and it was dissolved in water and the solution was acidified with 6N HCl to pH 2. Filtration gave 0.193 g (89% yield, mp 105°–108°) of N-(carboxymethyl)-N-[3-[3-(ethoxyphosphinyl)-propoxy]-5-(octadecyloxy)phenyl]glycine. The structure was confirmed by nmr and mass spectra.

EXAMPLE 90

3-Nitro-5-(octadecyloxy)phenylcarbamic acid dimethylethyl ester

A mixture of 5.0 g (11.5 mmol) of 3-nitro-5-(octadecyloxy)benzoic acid, 3.0 ml (13.8 mmol) of diphenylphosphoryl azide and 2.0 ml (13.8 mmol) of triethylamine in 45 ml of t-butylalcohol (freshly distilled from sodium) was stirred at reflux under argon for 20 hours. The excess t-butylalcohol was removed at reduced pressure and methylene chloride was added to the residue. The extract was washed with $NaHCO_3$ solution, dried and concentrated at reduced pressure to an oil which was purified by HPLC using 5% ethyl acetate-hexane to give 4.6 g (79% yield, mp 70°–72°) of 3-nitro-5-(octadecyloxy)phenylcarbamic acid dimethylethyl ester. The structure was confirmed by nmr and mass spectra.

EXAMPLE 91

3-Nitro-5-(octadecyloxy)benzenamine

To a solution of 4.6 g of 3-nitro-5-(octadecyloxy)-phenylcarbamic acid dimethylethyl ester in 100 ml of methylene chloride stirred at room temperature was added 20 ml of trifluoroacetic acid. The reaction mixture was kept at room temperature for 3.5 hours and the solvent was then removed at reduced pressure. The residue was treated with water and the product was filtered and recrystallized from ethyl acetate-hexane to give 3.6 g (97% yield, mp 106°–108°) of 3-nitro-5-(octadecyloxy)benzenamine.

Anal. Calcd for $C_{24}H_{42}N_2O_3$: C, 70.89; H, 10.41; N, 6.89. Found: C, 70.79; H, 10.44; N, 6.74.

EXAMPLE 92

N-(2-Methoxy-2-oxoethyl)-N-[3-nitro-5-(octadecyloxy)phenyl]glycine methyl ester

A mixture of 2.5 g (6.1 mmol) of 3-nitro-5-(octadecyloxy)benzenamine, 5.8 ml (61 mmol) of methyl bromoacetate, 3.3 g (15.4 mmol) of 1,8-bis(dimethylamino)naphthalene and 0.5 g (3.3 mmol) of sodium iodide in 50 ml of acetronitrile and 15 ml of DMF was stirred at reflux under argon for 32 hours. Methyl bromoacetate (3 ml), 1.5 g of 1,8-bis(dimethylamino)naphthalene and 0.5 g of sodium iodide were added and reflux was continued for 16 hours. The solvents were removed and reduced pressure and methylene chloride was added to the residue. The extract was washed with 0.05N HCl, dried and concentrated to an oil which was purified by HPLC using hexane:ethyl acetate:methylene chloride (75:15:10) to give 1.44 g (43% yield, mp 68°–74°) of N-(2-methoxy-2-oxoethyl)-N-[3-nitro-5-(octadecyloxy)phenyl]glycine methyl ester. The structure was confirmed by nmr and mass spectra.

EXAMPLE 93

N-(Carboxymethyl)-N-[3-nitro-5-(octadecyloxy)-phenyl]glycine

A solution of 1.44 g (2.6 mmol) of N-(2-methoxy-2-oxoethyl)-N-[3-nitro-5-(octadecyloxy)phenyl]glycine methyl ester and 15 ml of 1N NaOH in 65 ml of methanol, 10 ml of dioxane and 20 ml of water was stirred reflux for 5 hours. The solvents were removed at reduced pressure and the residue was dissolved in 400 ml of hot water. After cooling to room temperature, 6N HCl was added to acidify and the resultant precipitate was filtered. Purification by chromatography on 40 g of silica gel using 20% methanol-chloroform gave 1.1 g (81% yield, mp 131°–134°) of N-(carboxymethyl)-N-[3-nitro-5-(octadecyloxy)phenyl]glycine.

Anal. Calcd for $C_{28}H_{46}N_2O_7$: C, 64.34; H, 8.87; N, 5.36. Found: C, 64.15; H, 8.85; N, 5.18.

EXAMPLE 94

N-(Carboxymethyl)-N-[3-amino-5-(octadecyloxy)-phenyl]glycine

A mixture of 0.6 g of N-(carboxymethyl)-N-[3-nitro-5-(octadecyloxy)phenyl]glycine and 0.2 g of 10% palladium on carbon in 170 ml of THF and 10 ml of DMF was stirred in a hydrogen atmosphere at room temperature until uptake ceased after 4 hours. The reaction mixture was heated to dissolve the precipitated product and the catalyst was removed by filtration. The filtrate was concentrated at reduced pressure and the solid residue was dissolved in THF and the solution was passed through a SEP-PAK silica cartridge (Waters Associates). The eluent was concentrated at reduced pressure to a solid which was triturated with ethyl acetate and filtered to give 0.25 g (44% yield, mp 185°–195°) of N-(carboxymethyl)-N-[3-amino-5-(octadecyloxy)phenyl]glycine. The structure was confirmed by nmr and mass spectra.

EXAMPLE 95

3-(Acetylamino)-5-(octadecyloxy)nitrobenzene

To a solution of 1.4 g (3.44 mmol) of 3-nitro-5-(octadecyloxy)benzenamine and 0.75 ml (5.4 mmol) of triethylamine in 85 ml of THF stirred in an ice bath was added 0.25 ml (3.44 mmol) of acetyl chloride. The ice bath was removed after 15 minutes and the reaction mixture was stirred at room temperature for 17 hours. Triethylamine (0.3 ml) and acetyl chloride (0.15 ml) were added and stirring was continued for 5 hours. The solvent was removed at reduced pressure and the residue was crystallized from ethyl acetate-hexane to give 1.3 g (84% yield, mp 103°–107°) of 3-(acetylamino)-5-(octadecyloxy)nitrobenzene. The structure was confirmed by nmr and mass spectra.

EXAMPLE 96

3-(Acetylamino)-5-(octadecyloxy)benzenamine

A mixture of 1.3 g of 3-(acetylamino)-5-(octadecyloxy)nitrobenzene and 0.2 g of 10% palladium on carbon in 30 ml of THF and 25 ml of ethyl acetate was stirred in a hydrogen atmosphere until uptake ceased after 5 hours. The catalyst was removed by filtration and the filtrate was concentrated at reduced pressure to a solid which was recrystallized from ethyl acetate-hexane to give 1.0 mp 115°–117°, of 3-(acetylamino)-5-(octadecyloxy)benzenamine.

Anal. Calcd for $C_{26}H_{46}N_2O_2$: C, 74.59; H, 11.07; N, 6.69. Found: C, 74.38; H, 11.17; N, 6.60.

EXAMPLE 97

N-[3-(Acetylamino)-5-(octadecyloxy)phenyl]-N-[2-oxo-2-(phenylmethoxy)ethyl]glycine phenylmethyl ester A mixture of 1.1 g (2.63 mmol) of 3-(acetylamino)-5-(octadecyloxy)benzenamine, 4.2 ml (26 mmol) of benzyl bromoacetate, 1.4 g (6.6 mmol) of 1,8-bis(dimethylamino)naphthalene and 0.4 g (2.63 mmol) of sodium iodide in 40 ml of acetronitrile and 5 ml of DMF was stirred at reflux for 48 hours. The solvents were removed at reduced pressure and the residue was purified by HPLC using 35% ethyl acetate-hexane to give 0.3 g (16% yield, mp 89°–90°) of N-[3-(acetylamino)-5-(octadecyloxy)phenyl]-N-[2-oxo-2-(phenylmethoxy)ethyl]glycine benzyl ester. The structure was confirmed by nmr and mass spectra.

EXAMPLE 98

N-(Carboxymethyl)-N-[3-(acetylamino)-5-(octadecyloxy)phenylglycine

A mixture of 0.30 g of N-[3-(acetylamino)-5-(octadecyloxy)phenyl]-N-2-(phenylmethoxy)-2-oxoethyl]-glycinephenylmethyl ester and 0.10 g of 10% palladium on carbon in 15 ml of THF and 15 ml of ethyl acetate was stirred in a hydrogen atmosphere at room temperature until uptake ceased after 7 hours. The catalyst was removed by filtration and the filtrate was concentrated at reduced pressure to a solid which was recrystallized from ethyl acetate to give 0.13 g (59% yield, mp 156°–165°) of N-(carboxymethyl)-N-[3-(acetylamino)-5-(octadecyloxy)phenylglycine.

Anal. Calcd for $C_{30}H_{50}N_2O_6$: C, 67.38; H, 9.42; N, 5.24. Found: C, 67.28; H, 9.42; N, 5.05.

EXAMPLE 99

3-Hydroxy-5-(octadecyloxy)benzoic acid methyl ester

A mixture of 50.0 g (0.297 mol) of methyl 3,5-dihydroxybenzoate, 99.2 g (0.297 mol) of 1-bromooctadecane and 41 g (0.297 mol) of potassium carbonate in 100 ml of acetone and 50 ml of DMF was stirred at reflux under argon for 24 hours. The solvents were removed at reduced pressure and the residue was heated with methylene chloride and filtered hot. The filtrate was concentrated at reduced pressure to a solid which was recrystallized from methylene chloride-methanol to give the 3,5-dialkylated product. The filtrate was concentrated to dryness and the residue was recrystallized from methylene chloride-methanol to give more of the dialkylated product. The filtrate was concentrated to dryness and recrystallized from ether-hexane to give 40.2 g (32% yield, mp 95°–97°) of 3-hydroxy-5-(octadecyloxy)benzoic acid methyl ester.

Anal. Calcd for $C_{26}H_{44}O_4$: C, 74.24; H, 10.54. Found: C, 73.69; H, 10.57.

EXAMPLE 100

3-(Octadecyloxy)-5-(phenylmethoxy)benzoic acid methyl ester

A mixture of 50.9 g (0.12 mol) of 3-hydroxy-5-(octadecyloxy)benzoic acid methyl ester, 21.6 ml (0.18 mol) of benzyl bromide and 50 g (0.36 mol) of potassium carbonate in 750 ml of DMF was stirred and heated at 85° for 65 hours. The reaction mixture was filtered and the filtrate was concentrated at reduced pressure. The residue was recrystallized from methylene chloride-methanol to give 46.3 g (75% yield, mp 61°–63°) of 3-(octadecyloxy)-5-(phenylmethoxy)benzoic acid methyl ester. The structure was confirmed by the nmr spectrum.

EXAMPLE 101

3-(Octadecyloxy)-5-(phenylmethoxy)benzoic acid

A mixture of 46.3 g (0.091 mol) of 3-(octadecyloxy)-5-(phenylmethoxy)benzoic acid methyl ester and 45 ml (0.27 mol) of 6N NaOH in 750 ml of methanol and 300 ml of dioxane was stirred at reflux for 4 hours. The reaction mixture was filtered and the filtrate was concentrated at reduced pressure. The residue was suspended in water, acidified and filtered to give 44.4 g (99% yield, mp 97°–99°) of 3-(octadecyloxy)-5-(phenylmethoxy)benzoic acid.

Anal. Calcd for $C_{32}H_{48}O_4$: C, 77.38; H, 9.74. Found: C, 77.38; H, 9.75.

EXAMPLE 102

3-(Octadecyloxy)-5-(phenylmethoxy)phenylcarbamic acid dimethylethyl ester

A solution of 25 g (0.05 mol) of 3-(octadecyloxy)-5-(phenylmethoxy)benzoic acid, 13 ml (0.06 mol) of diphenylphosphoryl azide and 8.4 ml (0.06 mol) of triethylamine in 165 ml of t-butyl alcohol (freshly distilled from sodium) was stirred at reflux under argon for 19 hours. The excess t-butyl alcohol was removed at reduced pressure and the residue was extracted with methylene chloride. The dried extract was concentrated to a solid which was purified by chromatography on 200 g of 35–70 mesh silica gel using 50% ethyl acetate-hexane to give 28 g of slightly impure 3-(octadecyloxy)-5-(phenylmethoxy)phenylcarbamic acid dimethylethyl ester which was suitable for use in the next step.

EXAMPLE 103

3-(Octadecyloxy)-5-(phenylmethoxy)benzenamine

A solution of 28 g of 3-(octadecyloxy)-5-(phenylmethoxy)phenylcarbamic acid dimethylethyl ester and 76 ml of trifluoroacetic acid in 700 ml of methylene chloride was kept at room temperature for 2 hours. The solution was concentrated at reduced pressure and the residue was extracted with methylene chloride. The extract was washed with $NaHCO_3$ solution, dried and concentrated to a solid which was dissolved in 1000 ml of ether. The solution was treated with 21 ml of 3N HCl in ethanol. The hydrochloride salt which precipitated was filtered and treated with excess $NaHCO_3$ to liberate the free base which was extracted with methylene chloride. The dried extract was concentrated at reduced pressure to give 20.4 g (89% yield, mp 57°-59°) of 3-(octadecyloxy)-5-(phenylmethoxy)benzenamine.

Anal. Calcd for $C_{31}H_{49}NO_2$: C, 79.60; H, 10.56; N, 2.99. Found: C, 79.33; H, 10.53; N, 2.98.

EXAMPLE 104

N-(2-Methoxy-2-oxoethyl)-N-[3-(octadecyloxy)-5-(phenylmethoxy)phenyl]glycine methyl ester A mixture of 20.3 g (0.043 mol) of 3-(octadecyloxy)-5-(phenylmethoxy)benzenamine, 12 ml (0.13 mol) of methyl bromoacetate, 23 g (0.11 mol) of 1,8-bis(dimethylamino)naphthalene and 1.8 g (0.012 mol) of sodium iodide in 450 ml of acetonitrile and 150 ml of DMF was stirred at reflux under argon for 48 hours. The reaction mixture was filtered and the filtrate was concentrated at reduced pressure. The residue was extracted with ethyl acetate and the extract was washed with 0.5N HCl, dried and concentrated to a solid which was purified by HPLC using 20% ethyl acetate-hexane to give 15.6 g (59% yield, mp 66°-68°) of N-(2-methoxy-2-oxoethyl)-N-[3-(octadecyloxy)-5-(phenylmethoxy)phenyl]glycine methyl ester.

Anal. Calcd for $C_{35}H_{57}NO_6$: C, 72.63; H, 9.39; N, 2.29. Found: C, 72.60; H, 9.55; N, 2.29.

EXAMPLE 105

N-[3-Hydroxy-5-(octadecyloxy)phenyl]-N-(2-methoxy-2-oxoethyl)glycine methyl ester A mixture of 15.55 g of N-(2-methoxy-2-oxoethyl)-N-[3-(octadecyloxy)-5-(phenylmethoxy)phenyl]glycine methyl ester and 3.0 g of 10% palladium on carbon in 500 ml of THF was stirred in a hydrogen atmosphere at room temperature until uptake ceased after 23 hours. The catalyst was removed by filtration and the filtrate was concentrated at reduced pressure to a solid which was triturated with hexane and filtered to give 12.8 g (97% yield, 96°-98°) of N-[3-hydroxy-5-(octadecyloxy)phenyl]-N-(2-methoxy-2-oxoethyl)glycine methyl ester.

Anal. Calcd for $C_{30}H_{51}NO_6$: C, 69.06; H, 9.85; N, 2.68. Found: C, 69.12; H, 10.06; N, 2.72.

EXAMPLE 106

3-(3-Bromopropoxy)bromobenzene

A mixture of 5.0 g (0.029 mol) of 3-bromophenol, 29 ml (0.29 mol) of 1,3-dibromopropane and 12 g (0.087 mol) of potassium carbonate in 75 ml of acetone was stirred at reflux for 22 ours. The reaction mixture was filtered and the filtrate was concentrated at reduced pressure. The residue was purified by HPLC using 3% ethyl acetate-hexane to give 4.9 g (58% yield) of 3-(3-bromopropoxy)bromobenzene. The structure was confirmed by the nmr spectrum.

EXAMPLE 107

N-(2-methoxy-2-oxoethyl)-N-[3-[3-(3-bromophenoxy)-propoxy]-5(octadecyloxy)phenyl]glycine methyl ester A mixture of 1.0 g (1.92 mol) of N-(2-methoxy-2-oxoethyl)-N-[3-hydroxy-5-(octadecyloxy)phenyl]glycine methyl ester, 0.59 g (2.01 mmol) of 3-(3-bromopropoxy)bromobenzene, 0.53 g (3.83 mmol) of potassium carbonate and 0.29 g (1.92 mmol) of sodium iodide in 30 ml of acetone and 6 ml of DMF was stirred at reflux under argon for 65 hours. The solvents were removed at reduced pressure and the residue was treated with methylene chloride and filtered. The filtrate was concentrated and crystallized from methylene chloride-methanol to give 0.99 g (70%, mp 48°-50°) of N-(2-methoxy-2-oxoethyl)-N-[3-[3-(3-bromophenoxy)propoxy]-5-(octadecyloxy)phenyl]glycine methyl ester.

Anal. Calcd for $C_{39}H_{60}BrNO_7$: C, 63.75; H, 8.23; N, 1.91; Br, 10.87. Found: C, 63.43; H, 8.32; Br, 10.77.

EXAMPLE 108

N-(Carboxymethyl)-N-3-[3-[3-(bromophenoxy)propoxy]-5-(octadecyloxy)phenyl]glycine A solution of 0.95 g (1.29 mmol) of N-(2-methoxy-2-oxoethyl)-N-[3-[3-(3-bromophenoxy)propoxy]-5-(octadecyloxy)phenyl]glycine methyl ester and 0.86 ml (5.17 mmol) of 6N NaOH in 20 ml of methanol and 10 ml of dioxane was stirred at reflux under argon for 4.5 ours. The solvents were removed at reduced pressure and the residue was dissolved in water and acidified to pH 3 with 6N HCl. The product was extracted with ethyl acetate and the extract was concentrated to dryness and the resultant solid was recrystallized from methanol-water to give 0.75 g (83% yield, mp 93°-95°) of N-(carboxymethyl)-N-3-[3-[3-(3-bromophenoxy)-propoxy]-5-(octadecyloxy)phenyl]glycine.

Anal. Calcd for $C_{37}H_{56}BrNO_7$: C, 62.88; H, 7.99; N, 1.98; Br; 11.31. Found: C, 62.85; H, 8.08; N, 1.87; Br, 11.60.

EXAMPLE 109

3,5-Bis(phenylmethoxy)benzoic acid methyl ester

A mixture of 25.0 g (0.15 mol) of 3,5-dihydroxybenzoic acid methyl ester, 44 ml (0.37 mol) of benzyl bromide and 82 g (0.60 mol) of potassium carbonate in 300 ml of DMF was stirred and heated at 85° under argon for 45 hours. The cooled reaction mixture was filtered and the filtrate was concentrated at reduced pressure. The residue was treated with methylene chloride and the extract was filtered again to remove salts. Crystallization from methylene chloride-methanol gave 41.9 g (81% yield, mp 64°-66°) of 3,5-bis(phenylmethoxy)benzoic acid methyl ester.

Anal. Calcd for $C_{22}H_{20}O_4$: C, 75.84; H, 5.79. Found: C, 75.26; H, 5.62.

EXAMPLE 110

3,5-Bis(phenylmethoxy)benzoic acid

A solution of 41.4 g (0.12 mol) of 3,5-bis(phenylmethoxy)benzoic acid methyl ester and 59 ml (0.36 mol) of 6N NaOH in 700 ml of methanol and 350 ml of dioxane was stirred at reflux for 17 hours. The solvents were removed at reduced pressure and the residue was dissolved in water and acidified to pH 3 with 6N HCl. The resultant solid was filtered and recrystallized from methylene chloride-methanol to give 38.6 g (97% yield, mp 211°-213°) of 3,5-bis(phenylmethoxy)benzoic acid.

Anal. Calcd for $C_{21}H_{18}O_4$: C, 75.43; H, 5.43. Found: 74.82; H, 5.34.

EXAMPLE 111

3,5-Bis(phenylmethoxy)phenyl carbamic acid dimethylethyl ester

A mixture of 2.0 g (5.98 mmol) of 3,5-bis(phenylmethoxy)benzoic acid, 1.6 ml (7.18 mmol) of diphenylphosphoryl azide, 1.0 ml (7.18 mmol) of triethyl amine and 6 ml (64 mmol) of t-butyl alcohol (freshly distilled from sodium) in 15 ml of anhydrous toluene was stirred at reflux under argon for 18 hours. The reaction mixture was washed with NaHCO₃ solution, dried and concentrated at reduced pressure to an oil. Chromatography on 25 g of 230–400 mesh silica gel using 10% ethyl acetate-hexane gave 2.25 g (93% yield, mp 96°–98°) of 3,5-bis(phenylmethoxy) phenyl carbamic acid dimethylethyl ester.

Anal. Calcd for $C_{25}H_{27}NO_4$: C, 74.05; H, 6.71; N, 3.45. Found: C, 73.69; H, 6.84; N, 3.45

EXAMPLE 112

3,5-Bis(phenylmethoxy)benzenamine

A solution of 2.21 g of 3,5-bis(phenylmethoxy)phenyl carbamic acid dimethylethyl ester and 2.1 ml of trifluoroacetic acid in 50 ml of methylene chloride was left at room temperature for 18 hours. The reaction mixture was concentrated at reduced pressure and the residue was dissolved in methylene chloride and the extract was washed with NaHCO₃ solution, dried and concentrated to an oil which was triturated with methanol and filtered to give 0.70 g, mp 77°–80°, of 3,5-bis-(phenylmethoxy)benzenamine. The filtrate was concentrated to dryness, dissolved in ether and treated with 1.6 ml of 3N HCl in ethanol. The precipitated hydrochloride salt was filtered, treated with excess NaHCO₃ solution and extracted with methylene chloride. The dried extract was concentrated to give 0.57 g more of 3,5-bis(phenylmethoxy)benzenamine.

Anal. Calcd for $C_{20}H_{19}NO_2$: C, 78.66; H, 6.27; N, 4.59. Found: C, 78.47; H, 6.37; N, 4.51.

EXAMPLE 113

N-(2-Methoxy-2-oxoethyl)-N-[3,5-(bis(phenylmethoxy)phenyl]glycine methyl ester A mixture of 29.27 g (0.097 mol) of 3,5-bis(phenylmethoxy)benzenamine, 27 ml (0.29 mol) of methyl bromoacetate, 51.7 g (0.24 mol) of 1,8-bis(dimethylamino)-naphthalene and 4 g (0.027 mol) of sodium iodide in 500 ml of acetonitrile and 150 ml of DMF was stirred at reflux under argon for 48 hours. The solvents were removed at reduced pressure and the residue was extracted with ethyl acetate. The extract was washed with 0.5 N HCl, with NaHCO₃ solution, dried and concentrated to a solid. Purification by HPLC using 4% ethyl acetate-toluene and recrystallization from methylene chloride-hexane gave 28.65 g (66% yield, mp 98°–100°) of N-(2-methoxy-2-oxoethyl)-N-[3,5-(bis(phenylmethoxy)phenyl]glycine methyl ester.

Anal. Calcd for $C_{26}H_{27}NO_6$: C, 69.47; H, 6.05; N, 3.12. Found: C, 69.36; H, 5.98; N, 2.73.

EXAMPLE 114

N-[3,5-Dihydroxy)phenyl]-N-(2-methoxy-2-oxoethyl)glycine methyl ester

A mixture of 28.6 g of N-(2-methoxy-2-oxomethyl)-N-[3,5-(bis(phenylmethoxy)phenyl]glycine methyl ester and 5.0 g of 10% palladium on carbon in 500 ml of THF was shaken in a hydrogen atmosphere for 23 hours. The catalyst was removed by filtration and the filtrate was concentrated at reduced pressure to a solid which was triturated with hexane and filtered to give 16.2 g (94% yield, mp 200°–202°) of N-[(3,5-Dihydroxy)phenyl]-N-(2-methoxy-2-oxoethyl)glycine methyl ester.

Anal. Calcd for $C_{12}H_{15}NO_6$: C, 53.53; H, 5.62; N, 5.20. Found: C, 53.65; H, 5.51; N, 4.96.

EXAMPLE 115

N-(2-Methoxy-2-oxoethyl)-N-[3,5-bis(decyloxy)phenyl]glycine methyl ester

A mixture of 0.50 g (1.86 mmol) of N-[(3,5-Dihydroxy)phenyl]-N-(2-methoxy-2-oxoethyl)glycine methyl ester, 0.81 ml (3.9 mmol) of 1-bromodecane and 0.77 g (5.57 mmol) of potassium carbonate in 15 ml of acetone was stirred at reflux for 24 hours. An additional 0.8 ml of 1-bromodecane was added and reflux was continued for 48 hours. The reaction mixture was filtered through a Celite pad and the filtrate was concentrated at reduced pressure to an oil which was purified by HPLC using 15% ethyl acetate-hexane to give 0.54 g (52% yield) of N-(2-methoxy-2-oxoethyl)-N-[3,5-bis-(decyloxy)phenyl]glycine methyl ester as an oil. The nmr and mass spectra of this product were identical to those obtained using the procedure of Example 5.

EXAMPLE 116

3,4-Bis(tetradecyloxy)nitrobenzene

A mixture of 1.0 g (6.45 mmol) of 4-nitrocatechol, 4.8 ml (16.1 mmol) of 1-bromotetradecane and 2.5 g (17.4 mmol) of potassium carbonate in 20 ml of acetone and 10 ml of DMF was stirred at reflux under argon for 24 hours. The reaction mixture was filtered while hot and the filtrate was allowed to cool to room temperature and 3.5 g (99% yield, mp 64°–66°) of 3,4-bis(tetradecyloxy) nitrobenzene was obtained by filtration. The structure was confirmed by nmr and mass spectra.

Using this procedure, the reaction of 4-nitrocatechol with 1-bromodecane gave 3,4-bis-(decyloxy)nitrobenzene (mp 60°–61°, Anal, Calcd for $C_{26}H_{45}NO_4$: C, 71.68; H, 10.41; N, 3.22. Found: C, 71.63; H, 10.55; N, 3.21.

EXAMPLE 117

3,4-Bis(tetradecyloxy)benzenamine

A mixture of 3.5 g of 3,4-bis(tetradecyloxy)nitrobenzene and 0.5 g of 10% palladium on carbon in 80 ml of THF and 40 ml of ethyl acetate was stirred in a hydrogen atmosphere for 4 hours when uptake ceased. The catalyst was removed by filtration and the filtrate was concentrated at reduced pressure to a solid which was recrystallized from ethyl acetate-hexane to give 2.9 g (88% yield, mp 55°–58°) of 3,4-bis(tetradecyloxy)benzenamine.

Anal. Calcd for $C_{34}H_{63}NO_2$; C, 78.85; H, 12.26; N, 2.70. Found: C, 78.77; H, 12.01; N, 2.65.

The compounds in Table 24 were prepared using the procedure of Example 117.

TABLE 24

RO—⟨benzene⟩—NH₂ (with RO at 3,4 positions)

| Ex. | R | mp (°C.) | E.F. | Calcd C | Calcd H | Calcd N | Found C | Found H | Found N |
|---|---|---|---|---|---|---|---|---|---|
| 117a | C₁₀H₂₁ | 41–42 | C₂₆H₄₇NO₂ | 76.98 | 11.68 | 3.45 | 75.95 | 11.51 | 3.37 |
| 117b | COC₁₃H₂₇ | 66–69 | C₃₄H₅₉NO₄ | 74.81 | 10.89 | 2.57 | 74.95 | 10.70 | 2.63 |
| 117c | COC₁₇H₃₅ | 82–84 | C₄₂H₇₅NO₄ | 76.66 | 11.49 | 2.13 | 75.95 | 10.87 | 1.98 |
| 117d | CONHC₁₈H₃₇ | 129–133 | C₄₄H₈₁N₃O₄ | 73.80 | 11.40 | 5.87 | 73.97 | 11.35 | 5.80 |
| 117e | CONHC₁₄H₂₉ | 127–131 | C₃₆H₆₅N₃O₄ | 71.60 | 10.85 | 6.96 | 71.50 | 10.89 | 6.77 |

EXAMPLE 118

N-[2-oxo-2-(phenylmethoxy)ethyl]-N-[3,4-bis(tetradecyloxy)phenyl]glycine phenylmethyl ester A mixture of 2.8 g (5.4 mmol) of 3,4-bis(tetradecyloxy)benzenamine, 8.6 ml (54 mmol) of benzyl bromoacetate, 2.9 g (13.5 mmol) of 1,8-bis(dimethylamino)naphthalene and 0.3 g of sodium iodide in 60 ml of acetonitrile and 10 ml of DMF was stirred under argon for 48 hours. The solvents were removed at reduced pressure and the residue was treated with water and extracted with ethyl acetate. The dried extract was concentrated and purified by HPLC using 10% ethyl acetate-hexane to give 3.2 g (73% yield, mp 52°-52°) of N-[2-oxo-2-(phenylmethoxy)ethyl]-N-[3,4-bis(tetradecyloxy)-phenyl]glycine phenylmethyl ester. The structure was confirmed by nmr and mass spectra.

The compounds in Table 25 were prepared using the procedure of Example 118.

EXAMPLE 119

N-(Carboxymethyl)-N-[3,4-bis(tetradecyloxy)phenyl]glycine

A mixture of N-[2-oxo-2-(phenylmethoxy)ethyl]-N-[3,4-bis(tetradecyloxy)phenyl]glycine phenylmethyl ester and 0.5 g of 10% palladium on carbon in 40 ml of THF and 20 ml of ethyl acetate was stirred in a hydrogen atmosphere at room temperature for 2.5 hours when uptake cased. The catalyst was removed by filtration and the filtrate was concentrated a reduced pressure to a solid which was triturated with hexane and filtered to give 1.4 g (56% yield, mp 89°–93°) of pure N-(carboxymethyl)-N-[3,4-bis(tetrahydecyloxy)-phenyl]glycine.

Anal. Calcd for C₃₈H₆₇NO₆: C, 72.00; H, 10.65; N, 2.21. Found: C, 71.98; H, 10.41; N, 2.08.

The compounds in Table 26 were prepared using the procedure of Example 119.

TABLE 25

RO—⟨benzene⟩—N(CH₂COOCH₂C₆H₅)₂ (with RO at 3,4 positions)

| Ex. | R | mp (°C.) | E.F. | Calcd C | Calcd H | Calcd N | Found C | Found H | Found N |
|---|---|---|---|---|---|---|---|---|---|
| 118a | C₁₀H₂₁ | liquid | C₄₄H₆₃NO₆ | | | | N.O. | | |
| 118b | COC₁₃H₂₇ | liquid | C₅₂H₇₅NO₈ | | | | N.O. | | |
| 118c | COC₁₇H₃₅ | 52–54 | C₆₀H₉₁NO₈ | | | | | | N.O. |
| 118d | CONHC₁₈H₃₇ | 116–119 | C₆₂H₉₇N₃O₈ | | | | | | N.O. |
| 118e | CONHC₁₄H₂₉ | 115–119 | C₅₄H₈₁N₃O₈ | 72.05 | 9.07 | 4.67 | 71.92 | 9.15 | 4.77 |

*Not Obtained

TABLE 26

RO—⟨benzene⟩—N(CH₂COOH)₂ (with RO at 3,4 positions)

| Ex. | R | mp (°C.) | E.F. | Calcd C | Calcd H | Calcd N | Found C | Found H | Found N |
|---|---|---|---|---|---|---|---|---|---|
| 119a | C₁₀H₂₁ | semisolid | C₃₀H₅₁NO₆ | | | | N.O. | | |
| 119b | COC₁₃H₂₇ | 129–131 | C₃₈H₆₃NO₈ | 68.95 | 9.59 | 2.12 | 68.96 | 9.58 | 2.13 |
| 119c | COC₁₇H₃₅ | 115–120 | C₄₆H₇₉NO₈ | 71.37 | 10.29 | 1.81 | 71.74 | 10.52 | 1.87 |
| 119d | CONHC₁₈H₃₇ | 151–156 | C₄₈H₈₅N₃O₈ | 69.28 | 10.30 | 5.05 | 69.53 | 10.23 | 5.04 |
| 119e | CONHC₁₄H₂₉ | 155–159 | C₄₀H₆₉N₃O₈ | 66.73 | 9.66 | 5.84 | 66.80 | 9.53 | 5.82 |

EXAMPLE 120

3,4-Bis[(1-oxodecyl)oxy]nitrobenzene

To a stirred, ice bath cooled solution of 1.0 g (6.45 mmol) of 4-nitrocatechol and 2 ml of pyridine in 25 ml of methylene chloride and 5 ml of THF under argon was added 3.2 ml (15.5 mmol) of decanoyl chloride in 5 ml of THF. The reaction mixture was allowed to warm to room temperature and stirred for 18 hours when it was poured into water and extracted with methylene chloride. The dried extract was concentrated to an oil which was purified by chromatography on 70 g of silica gel using 5% ethyl acetate-hexane to give 2.9 g (97% yield, mp 45°–47°) of 3,4-bis-[(1-oxo]nitrobenzene.

Anal. Calcd for $C_{26}H_{41}NO_6$: C, 67.36; H, 8.91; N, 3.02. Found: C, 67.47; H, 8.84; N, 2.97.

Using this procedure, the reaction of 4-nitrocatechol with tetradecanoyl chloride gave 3,4-bis [(1-oxotetradecyl)oxy]nitrobenzene (mp 58°–60°, Anal. Calcd for $C_{34}H_{57}NO_6$: C, 70.72; H, 9.98; N, 2.43. Found: C, 70.91; H, 9.61; N, 2.41.

Using this procedure, the reaction of 4-nitrocatechol with octadecanoyl chloride gave 3,4-bis [(1-oxooctadecyl)oxy]nitrobenzene (mp 68°–70°) The structure was confirmed by the nmr spectrum.

Using this procedure, the reaction of 4-nitrocatechol with octadecyl isocyannate gave 3,4-bis[[(octadecylamino)carbonyl]oxy]nitrobenzene (mp 117°–121°). The structure was confirmed by the nmr spectrum.

Using this procedure, the reaction of 4-nitrocatechol with tetradecyl isocyanate gave 3,4-bis [[(tetradecylamino)carbonyl]oxy]nitrobenzene (mp 100°–104°). The structure was confirmed by the nmr spectrum.

EXAMPLE 121

3,4-Bis[(1-oxodecyl)oxy]benzenamine

A mixture of 2.9 g of 3,4-bis[(1-oxodecyl)oxy]nitrobenzene and 0.5 g of 10% palladium on carbon in 50 ml of ethyl acetate and 10 ml of THF was stirred in a hydrogen atmosphere at room temperature for 5 hours when uptake ceased. The catalyst was removed by filtration and the filtrate was concentrated to an oil which was crystallized from ethyl acetate-hexane to give 2.5 g (92% yield, mp 44°–46°) of 3,4-bis[(1-oxodecyl)oxy]benzenamine.

Anal. Calcd for $C_{26}H_{43}NO_4$: C, 72.02; H, 10.00; N, 3.23. Found: C, 72.28; H, 9.59; N, 3.25.

EXAMPLE 122

N-[3,4-bis[(1-Oxodecyl)oxy]phenyl]-N-[2-oxo-2-(phenylmethoxy)ethyl]glycine phenylmethyl ester A mixture of 2.5 g (5.77 mmol) of 3,4-bis[(1-oxodecyl)oxy]benzenamine, 9.1 ml (57.7 mmol) of benzyl bromoacetate, 3.1 g (14.4 mmol) of 1,8-bis(dimethylamino)-naphthalene and 0.34 g (2.3 mmol) of sodium iodide in 50 ml of acetonitrile and 10 ml of DMF was stirred at reflux for 48 hours. The solvents were removed at reduced pressure and the residue was treated with methylene chloride and water. The organic phase was separated, dried and concentrated to an oil which was purified by HPLC using 20% ethyl acetate-hexane to give 2.2 g (52% yield) of N-[3,4-bis[(1-oxodecyl)oxy]-phenyl]-N-[2-oxo-2-phenylmethoxy)ethyl]glycine phenylmethyl ester as an oil. The structure was confirmed by nmr and mass spectra.

EXAMPLE 123

N-(Carboxymethyl)-N-[3,4-bis[(1-oxodecyl)oxy]-phenyl]glycine

A mixture of 2.2 g of N-[3,4-bis[(1-oxodecyl)oxy]-phenyl]-N-[2-oxo-2-(phenylmethoxy)ethyl]glycine phenylmethyl ester and 0.5 g of 10% palladium on carbon in 20 ml of ethyl acetate and 30 ml of THF was stirred in a hydrogen atmosphere at room temperature until uptake ceased after 10 hours. The catalyst was removed by filtration and the filtrate was concentrated at reduced pressure to a semisolid which was crystallized from ethyl acetate-hexane to give 1.3 g (78% yield, mp 131°–133°) of N-(carboxymethyl)-N-[3,4-bis[(1-oxodecyl)oxy]phenyl]glycine.

Anal. Calcd for $C_{30}H_{47}NO_8$: C, 65.55; H, 8.62; N, 2.55. Found: C, 65.46; H, 8.43; N, 2.49.

EXAMPLE 124

N-[3-(Octadecyloxy)phenyl]glycine phenylmethyl ester

A mixture of 1.08 g (3.0 mmol) of 3-(oxtadecyloxy)-benzenamine, 0.52 ml (3.3 mmol) of benzyl bromoacetate and 0.8 g (6.0 mmol) of potassium carbonate in 40 ml of acetone was stirred at reflux under argon for 18 hours. The reaction mixture was filtered and the filtrate was concentrated at reduced pressure to an oil which was purified by chromatography on 150 g of silica gel using 20% ethyl acetate-hexane to give 1.1 g (72% yield, mp 55°–60°) of N-[3-(octadecyloxy) phenyl]glycine phenylmethyl ester.

Anal. Calcd for $C_{33}H_{51}NO_3$: C, 77.75; H, 10.08; N, 2.75. Found: C, 77.98; H, 10.09; N, 2.79.

The compounds in Table 27 were prepared using the procedure of Example 124.

TABLE 27

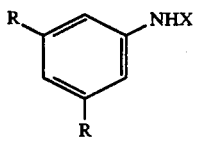

| | | | | | Microanalytical Data | | | | | |
|---|---|---|---|---|---|---|---|---|---|---|
| | | | | | Calcd | | | Found | | |
| Ex. | R | X | mp (°C.) | E.F. | C | H | N | C | H | N |
| 124a | CONHC$_{10}$H$_{21}$ | (CH$_2$)$_2$COOC$_2$H$_5$ | 81–83 | C$_{33}$H$_{57}$N$_3$O$_4$ | 70.80 | 10.26 | 7.51 | 70.73 | 9.99 | 7.41 |
| 124b | CONHC$_{10}$H$_{21}$ | (CH$_2$)$_3$COOC$_2$H$_5$ | 102–104 | C$_{34}$H$_{54}$N$_3$O$_4$ | 71.16 | 10.36 | 7.32 | 71.02 | 10.21 | 7.14 |
| 124c | OC$_{14}$H$_{29}$ | CH$_2$COOBz | 44–45 | C$_{43}$H$_{71}$NO$_4$ | | | | | N.O. | |
| 124d | OCH$_2$CHOHC$_8$H$_{17}$ | CH$_2$COOCH$_3$ | oil | C$_{33}$H$_{55}$NO$_8$ | 66.75 | 9.34 | 2.36 | 66.82 | 9.19 | 2.37 |

TABLE 27-continued

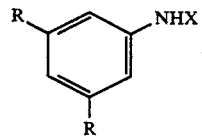

| Ex. | R | X | mp (°C.) | E.F. | Calcd C | H | N | Found C | H | N |
|---|---|---|---|---|---|---|---|---|---|---|
| 124e | COOC$_{14}$H$_{29}$ | CH$_2$COOBz | oil | C$_{45}$H$_{71}$NO$_6$ | | | | N.O. | | |

EXAMPLE 125
N-[3-(Octadecyloxy)phenyl]glycine

A mixture of 0.52 g of N-[3-(oxtadecyloxy)phenyl]glycine phenylmethyl ester and 0.2 g of 10% palladium on carbon in 40 ml of ethyl acetate was shaken under an initial hydrogen pressure of 52 psi until uptake ceased after 1.5 hours. The catalyst was removed by filtration and the filtrate was concentrated to a solid which was recrystallized from methanol-water to give 0.31 g, mp 92°-92°, of N-[3-(octadecyloxy)phenyl]glycine.

Anal. Calcd for C$_{26}$H$_{45}$NO$_3$: C, 74.42; H, 10.81; N, 3.34. Found: C, 74.53; H, 11.10; N, 3.63.

EXAMPLE 126
3-[[3,5-bis[(Decylamino)carbonyl]phenyl](3-ethoxy-3-oxopropyl)amino]propanoic acid ethyl ester A mixture of 0.50 g (1.09 mmol) of 3,5-bis[(decylamino)carbonyl]benzenamine, 0.28 ml (2.18 mmol) of ethyl 3-bromopropionate, 0.3 (2.18 mmol) of potassium carbonate and 0.009 g of tetrabutylammonium bromide in 5 ml of DMF was stirred and heated at 100° under argon for 24 hours. An additional 1.4 ml (11 mmol) of ethyl 3-bromopropionate and 0.33 g (2.18 mmol) of sodium iodide were added and the mixture was stirred and heated at 100° for 67 hours. The solvent was removed at reduced pressure and the residue was extracted with ethyl acetone. The extract was washed with NaHCO$_3$ solution, dried and concentrated to an oil which was purified by HPLC using 40% ethyl acetate-hexane to give 0.27 g (37% yield) of 3-[[3,5-bis(-decyalmino)carbonyl]phenyl](3-ethoxy-3-oxopropyl)amino]propanoic acid ethyl ester as an oil.

Anal. Calcd for C$_{38}$H$_{65}$N$_3$O$_6$: C, 69.16; H, 9.93; N, 6.37. Found: C, 69.10; H, 9.96; N, 6.16.

EXAMPLE 127
3-[[(2-Carboxyethyl)-3,5-bis[(decylamino)carbonyl]phenyl]amino]propanoic acid A solution of 0.23 g (0.35 mmol) of 3-[[3,5-bis(-decylamino)carbonyl]phenyl](3-ethoxy-3-oxopropyl)amino]propanoic acid ethyl ester and 1.4 ml (1.4 mmol) of 1 N NaOH in 10 ml of methanol was stirred at room temperature for 16 hours. The solvent was removed at reduced pressure, the residue was dissolved in water and acidified with 0.2 ml of acetic acid. The precipitate was filtered and recrystallized from acetone-hexane to give 0.13 g (60% yield, mp 139°-141°) of 3-[[(2-carboxyethyl)-3,5-bis[(decylamino)carbonyl]phenyl]amino]propanoic acid.

Anal. Calcd for C$_{34}$H$_{57}$N$_3$O$_6$: C, 67.63; H, 9.51; N, 6.96. Found: C, 67.65; H, 9.51; N, 6.92.

The compounds in Table 28 were prepared using the procedure of Example 127 if the precursor was a methyl ester or the procedure of Example 125 of the precursor was a benzyl ester.

TABLE 28

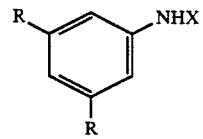

| Ex. | R | X | mp (°C.) | E.F. | Calcd C | H | N | Found C | H | N |
|---|---|---|---|---|---|---|---|---|---|---|
| 127a | CONHC$_{10}$H$_{21}$ | (CH$_2$)$_3$COOH | 138–140 | C$_{31}$H$_{53}$N$_3$O$_4$ | 70.02 | 10.05 | 7.90 | 69.97 | 10.08 | 8.05 |
| 127b | CONHC$_{10}$H$_{21}$ | (CH$_2$)$_3$COOH | 111–114 | C$_{32}$H$_{55}$N$_3$O$_4$ | 70.42 | 10.16 | 7.70 | 70.68 | 10.40 | 7.73 |
| 127c | OC$_{14}$H$_{29}$ | CH$_2$COOH | 38–40 | C$_{36}$H$_{65}$N$_3$O$_4$ | | | | *N.O. | | |
| 127d | OCH$_2$CHOHC$_8$H$_{17}$ | CH$_2$COOH | 111–114 | C$_{28}$H$_{49}$NO$_6$ | 67.85 | 9.96 | 2.83 | 67.73 | 9.77 | 2.76 |
| 127e | COOC$_{14}$H$_{29}$ | CH$_2$COOH | 86–89 | C$_{38}$H$_{65}$NO$_6$ | 72.23 | 10.37 | 2.22 | 72.54 | 10.46 | 2.26 |

Not Obtained

EXAMPLE 128
4-[[3,5-bis[(Decylamino)carbonyl]phenyl](4-ethoxy-4-oxobutyl)amino]butanoic acid ethyl ester A mixture of 0.25 g (0.54 mmol) of 3,5-bis(-decylamino)carbonyl]benzenamine, 0.48 ml of ethyl 4-bromobutyrate, 0.91 g (0.54 mmol) of potassium iodide and 0.15 g (1.09 mmol) of potassium carbonate in 10 ml of DMF was stirred at 80° for 69 hours. An additional 0.48 ml of ethyl 4-bromobutyrate was added and the mixture was stirred and heated at 100° for 48 hours. The solvent was removed at reduced pressure and the residue was extracted with ethyl acetate. The dried extract was concentrated to an oil which was purified by chromatography on 13 g of silica gel using 40% ethyl acetate-hexane to give 0.10 g (21% yield, mp 75°–77°) of 4-[[3,5-bis[(decylamino)carbonyl]phenyl](4-ethoxy-4-oxobutyl)amino]butanoic acid ethyl ester. The structure was confirmed by nmr and mass spectra.

EXAMPLE 129

4-[[3,5-bis[(Decylamino)carbonyl]phenyl](4-hydroxy-4-oxobutyl)amino]butanoic acid A solution of 0.099 g (0.14 mmol) of 4-[[3,5-bis(-decylamino)carbonyl]phenyl](4-ethoxy-4-oxobutyl)amino]butanoic acid ethyl ester and 0.6 ml (0.6 mmol) of 1 N NaOH in 4of methanol was kept at room temperature for 17 hours. The solvent was removed at reduced pressure and the residue was dissolved in water and acidified with 0.04 ml of acetic acid. The precipitate was filtered and recrystallized from methanol to give 0.046 g (51% yield, mp 154°–156°) of 4-[[3,5-bis[-(decylamino)carbonyl]phenyl](4-hydroxy-4-oxobutyl-)amino]butanoic acid.

Anal. Calcd for $C_{36}H_{61}N_3O_6$: C. 68.43; H, 9.73; N, 6.65. Found: C, 68.25: H, 9.53: N, 6.60.

EXAMPLE 130

N-[3,5-bis(Decyloxy)phenyl]-N-[2-[2-(diethylamino)ethoxy]-2-oxoethyl]glycine 2-(diethylamino)ethyl ester dihydrochloride A mixture of 0.50 g (0.96 mmol) of N-(carboxymethyl)-N-[3,5-bis(decyloxy)phenyl]glycine, 1.3 g (9.6 mmol) of 2-diethylaminoethyl chloride and 1.34 ml (7.7 mmol) of N,N-diisopropyl ethylamine in 15 ml of DMF was stirred at room temperature for 48 hours. The reaction mixture was concentrated on the oil pump and the residue was treated with NaHCO$_3$ solution. The product was extracted with ethyl acetate and the dried extract was concentrated at reduced pressure to an oil which was purified by chromatography on 25 g of 230–400 mesh silica gel using methylene chloride(90)-:methanol(10);concentrated ammonium hydroxide(0.1). The resultant pure free base (0.51 g) was converted to the dihydrochloride salt by treatment of a methylene chloride solution was 0.95 ml of 3N HCl in ethanol. After concentration, the product was dissolved in ether and stored at −18° until crystals formed. Filtration gave 0.28 g, mp 132°–135° of N-[3,5-bis-(decyloxy)-phenyl]-N-[2-[2-(diethylamino)ethoxy]-2-oxoethyl]glycine 2-(diethylamino)ethyl ester dihydrochloride.

Anal. Calcd for $C_{42}H_{77}N_3O_6.2$ HCl: C, 63.61; H, 10.04; N, 5.30; Cl−, 8.94. Found: C, 63.37; H, 10.01; N, 5.22; Cl−, 8.75.

EXAMPLE 131

N-[3,5-bis(Decyloxy)phenyl]-N-[[bis(2-hydroxyemthyl-)amino]carbonyl]methoxy]-2-oxoethyl]glycine [[bis(2-hydroxyethyl)amino]carbonyl]methyl ester A mixture of 1.0 g (1.92 mmol) of N-(carboxymethyl)-N-[3,5-bis(decyloxy)phenyl]glycine, 2.6 ml of N,N-diisopropylethylamine and a solution of N,N-bis(2-hydroxyethyl)-3-chloroacetamide [prepared from the reaction of 2.1 g (20 mmol) of diethanolamine, 1.6 ml (20 mmol) of chloroacetyl chloride and 3.1 ml (22 mmol) of triethylamine in 25 ml of DMF] was stirred at room temperature for 17 hours. Sodium iodide (3.0 g, 20 mmol) was added and the reaction mixture was stired and heated at 60° under argon for 25 hours. The mixture was concentrated at reduced pressure and NaHCO$_3$ solution was added to the residue. The product was extracted with ethyl acetate and the extract was washed with water, dried and concentrated to an oil which was crystallized from methylene chloride-ether to give 0.455 g (29% yield, mp 104°–107°) of N-[3,5-bis(-decyloxy)phenyl]-N-[[bis(2-hydroxyethyl)amino]carbonyl]methoxy]-2-oxoethyl]glycine [[bis(2-hydroxyethyl)amino]carbonyl]methyl ester.

Anal. Calcd for $C_{42}H_{73}N_3O_{12}$: C, 62.12; H, 9.06; N, 5.17. Found: C, 61.79; H, 9.02; N, 5.10.

EXAMPLE 132

N-[2-[(Acetyloxy)methoxy]-2-oxoethyl]-N-[3,5-bis(-decyloxy)phenyl]glycine (acetyloxy)methyl ester A mixture of 2.0 g (3.83 mmol) of N-(carboxymethyl)-N-[3,5-bis(decyloxy)phenyl]glycine, 1.24 g (11.5 mmol) of chloromethyl acetate, 2.2 ml (15.3 mmol) of triethylamine and 1.15 g (7.7 mmol) of sodium iodide in 100 ml of acetone was stirred at reflux under argon for 1 hour. DMF (10 ml) was added and reflux was continued for 49 hours. The solvents were removed at reduced pressure and NaHCO$_3$ solution was added to the residue. The product was extracted with ethyl acetate and the dried extract was concentrated to an oil which was purified by HPLC using 25% ethyl acetate-hexane to give 0.74 g (30% yield, mp 37°–309°) of N-[2-[(acetyloxy)methoxy]-2-oxoethyl]-N-[3,5-bis(decyloxy)phenyl]glycine (acetyloxy)methyl ester.

Anal. Calcd for $C_{36}H_{59}NO_{10}$: C, 64.94; H, 8.93; N, 2.10. Found: C, 64.49; H, 8.94; N, 2.26.

EXAMPLE 133

N-[2-[(Acetyloxy)methoxy]-2-oxoethyl]-N-[3,5-bis[-(decylamino)carbonyl]phenyl]glycine (acetyloxy) methyl ester A mixture of 0.106 g (0.17 mmol) of N-(carboxymethyl)-N-[3,5-bis[(decylamino) carbonyl]phenyl]glycine, 0.107 g (0.87 mmol) of chloromethyl acetate, 0.07 ml (0.5 mmol) of triethylamine and 0.051 g (0.33 mmol) of sodium iodide in 3 ml of anhydrous acetone was stirred at reflux under argon for 26 hours. The solvent was removed, NaHCO$_3$ solution was added to the residue and the product was extracted with ethyl acetate. The dried extract was concentrated to an oil which was purified by chromatography on 20 g of silica gel using 50% ethyl acetate-hexane to give 0.058 of g N-[2-[(acetyloxy)methoxy]-2-oxoethyl]-N-[3,5-bis[-(decylamino) carbonyl]phenyl]glycine (acetyloxy) methyl ester was a waxy solid.

Anal. Calcd for $C_{38}H_{61}N_3O_{10}$: C, 63.40; H, 8.54; N, 5.84. Found: C, 63.47; H, 8.47; N, 5.70.

EXAMPLE 134

N-[3,5-bis[(Decylamino)carbonyl]phenyl]-N-[2-[(2,2-dimethyl-1-oxopropoxy)methoxy]-2-oxoethyl]glycine (2,2-dimethyl-1-oxopropoxy)methyl ester A mixture of 0.1023 g (0.174 mmol) of N-(carboxymethyl)-N-[3,5-bis(decylamino)carbonyl]phenyl]glycine, 0.12 ml (0.84 mmol) of chloromethyl pivalate, 0.07 ml (0.49 mmol) of triethylamine and 0.041 g of sodium iodide in 3 ml of anhydrous acetone was stirred at reflux under argon for 17 1 hours. The solvent was removed, NaHCO$_3$ solution was added to the residue and the product was extracted with ethyl acetate. The dried extract was concentrated to an oil and purified by chromatography on 20 g of silica gel using 50% ethyl acetate-hexane to give 0.093 g (66% yield) of N-[3,5-bis[-(decylamino)carbonyl]phenyl]-N-[2-[(2,2-dimethyl-1-oxopropoxy)methoxy]-2-oxoethyl]glycine (2,2-dimethyl-1-oxopropoxy)methyl ester was a waxy solid.

Anal. Calcd for $C_{44}H_{73}N_3O_{10}$: C, 65.72; H, 9.15; N, 5.23. Found: C, 65.23; H, 9.27; N, 5.18.

EXAMPLE 135

N-(3-Hydroxyphenyl)-N-(2-methoxy-2-oxoethyl)glycine methyl ester

A mixture of 1.85 g (0.0093 mol) of 3-dimethylethyloxyaniline, 4.4 ml (0.0465 mol) of methyl bromoacetate, 8.0 g (0.037 mol) of 1,8-bis(dimethylamino)naphthalene and 1.4 g (0.0093 mol) of sodium iodide in 100 ml of dry acetonitrile was stirred at reflux for 41 hours. The reaction mixture was filtered, the filtrate was concentrated and the residue was extracted with ethyl acetate. The extract was washed with 1 N Hcl, with NaHCO$_3$ solution, dried and concentrated to an oil which was purified by chromatography on 150 g of silica gel using 30% ethyl acetate-hexane to give 2.73 g (88% yield) of N-(2-methoxy-2-oxoethyl)-N-[3-(phenylmethoxy)phenyl]glycine methyl ester. This was dissolved in 60 ml of ethyl acetate, 0.5 g of 10% palladium on carbon was added and the mixture was shaken under an initial hydrogen pressure of 53 psi on a Parr Hydrogenator for 20 hours. An additional 0.5 g of 10% palladium on carbon was added and shaking under hydrogen pressure was continued for 20 hours. The catalyst was removed by filtration and the filtrate was concentrated to an oil which was purified by chromatography on 175 g of silica gel using 50% ethyl acetate-hexane to give 1.32 g of N-(3-hydroxyphenyl)-N-(2-methoxy-2-oxoethyl)glycine methyl ester as an oil. The structure was confirmed by nmr and mass spectra.

EXAMPLE 136

4-[Decylamino)carbonyl]nitrobenzene

To a solution of 5.4 ml (0.027 mol) of decylamine and 5.6 ml (0.04 mol( of triethylamine in 20 ml of methylene chloride cooled in an ice bath was added dropwise a solution of 5.0 g (0.027 mol) of 4-nitrobenzoyl chloride in 40 ml of methylene chloride. The reaction mixture was stirred in the ice bath for 30 minutes, at room temperature for 15 minutes and kept at 0° for 18 hours. After dilution was methylene chloride, the mixture was washed with 0.5 N NaOH and the extract was dried and concentrated to a solid. Recrystallization from methylene chloride-hexane gave 8.1 g (98% yield, mp 89°-91°) of 4-[(decylamino)carbonyl]nitrobenzene. The nmr was consistent with the structure.

Using this procedure, 2-nitrobenzoyl chloride gave 21-[(decylamino)carbonyl]nitrobenzene, mp 55°-57° in 95% yield.

EXAMPLE 137

4-[Decylamino)carbonyl]benzenamine

A mixture of 8.05 g of 4-[(decylamino)carbonyl]nitrobenzene and 2.5 g of 10% palladium on carbon in 175 ml of THF was shaken under an initial hydrogen pressure of 54 psi in a Parr Hydrogenator for 17 hours. The catalyst was removed by filtration and the filtrate was concentrated to a solid which was triturated with hexane and filtered to give 6.88 g (95% yield, mp 117°-119°) of 4-[(decylamino)carbonyl]benzenamine. The structure was confirmed by the nmr spectrum.

Using this procedure 2-[(decylamino)carbonyl]nitrobenzene gave 2-[(decylamino)carbonyl]benzenamine, mp 72°-74°, in 91% yield.

EXAMPLE 138

N-[4-[(Decylamino)carbonyl]phenyl]-N-(2-methoxy-2-oxoethyl)glycine methyl ester

A mixture of 4.0 g (0.0145 mol) of 4-[(decylamino)carbonyl]benzenamine, 20.5 ml (0.217 mol) of methyl bromoacetate, 4.0 g (0.029 mol) of potassium carbonate, 4.3 g (0.029 mol) of sodium iodide and 0.21 g 0.065 mmol ) of tetrabutylammonium bromide in 40 ml of anhydrous DMF was stirred and heated at 100° for 69 hours. The solvent was removed on the oil pump and the residue was extracted with ethyl acetate. The extract was washed with NaHCO$_3$ solution, dried and concentrated to an oil which was purified by chromatography on 40 g of silica gel using 75% ethyl acetate-hexane. The pure fractions were combined, concentrated and recrystallized three times from methylene chloride-ether to give 1.98 g (33% yield, mp 104°-106°) of N-[4-[(decylamino) carbonyl]phenyl]-N-(2-methoxy-2-oxoethyl)glycine methyl ester.

Anal. Calcd for $C_{23}H_{36}N_2O_5$: C, 65.69; H, 8.63; N, 6.66. Found: C, 65.34; H, 8.76; N, 6.58.

Using this procedure 2-[(decylamino)carbonyl]benzenamine gave N-[2-(decylamino)carbonyl]phenyl]-N-(2-methoxy-2-oxoethyl)glycine methyl ester, mp 35°-38°, in 35% yield.

Anal. Calcd for $C_{23}H_{36}N_2O_5$: C, 65.69; H, 8.63; N, 6.66. Found: C, 65.12; H, 8.67; N, 6.49.

EXAMPLE 139

N-(Carboxymethyl)-N-[4-[(decylamino)carbonyl]phenyl]glycine

A solution of 1.88 g (4.47 mmol) of N-[4-[(decylamino)carbonyl]phenyl]-N-(2-methoxy-2-oxoethyl)glycine methyl ester and 17.0 ml (17.9 mmol) of 1 N NaOH in 125 ml of methanol was kept at room temperature for 18 hours. The solvent was removed, water was added to the residue and the pH was adjusted to 2 with 6 N HCl. The precipitate was filtered and recrystallized from methanol-water to give 1.63 g (93% yield, mp 155°-157°) of N-(carboxymethyl)-N-[4-[(decylamino)carbonyl]phenyl]glycine.

Anal. Calcd for $C_{21}H_{32}N_2O_5$: C, 64.26; H, 8.22; N, 7.14. Found: C, 64.36; H, 8.26; N, 7.17.

Using this procedure N-[2-[(decylamino)carbonyl]phenyl]-N-(2-methoxy-2-oxoethyl)glycine methyl ester gave N-(carboxymethyl)-N-[4-[(decylamino)carbonyl]phenyl]glycine as an oil.

Anal. Calcd for $C_{21}H_{32}N_2O_5$: C, 64.26; H, 8.22; N, 7.14. Found: C, 64.46; H, 8.29; N, 7.04.

EXAMPLE 140

N-[2,5-bis[(Decylamino)carbonyl]nitrobenzene

A mixture of 10 g (0.047 mol) of nitroterephthalic acid, 40 ml of thionyl chloride and 1 ml of anhydrous DMF was stirred at reflux for 5 hours. The reaction mixture was concentrated at reduced pressure and the residual acid chloride was dissolved in anhydrous THF and added dropwise over 30 minutes to a stirred, ice bath cooled solution of 25 ml (0.126 mol) of decylamine and 15 ml (0.108 mol) of triethylamine in 100 ml of anhydrous THF. Additional THF (50 ml) was added and stirring was continued for 17 hours at room temperature. Water (1 L) was added and the precipitate was filtered and recrystallized from methanol-water to give 20.4 g, mp 159°-160° of N-[2,5-bis[(decylamino)carbonyl]nitrobenzene.

Anal. Calcd for $C_{28}H_{47}N_3O_4$: C, 68.68; H, 9.67; N, 8.58. Found: C, 68.81; H, 9.72; N, 8.62.

EXAMPLE 141

N-[2,5-bis[Decylamino)carbonyl]benzenamine

A mixture of 15 g of N-[2,5-bis[(decylamino)carbonyl]nitrobenzene and 1 g of 10% palladium on carbon in 200 ml of THF was shaken under an initial hydrogen pressure of 52 psi on a Parr Hydrogenator for 18 hours. The catalyst was removed by filtration and the filtrate was concentrated to a solid which was crystallized three times from methylene chloride-methanol to give 3.85 g, mp 170°-172°, of N-[2,5-bis[decyalmino)carbonyl]benzenamine.

Anal. Calcd for $C_{28}H_{49}N_3O_2$; C, 73.16; H, 10.74; N, 9.14, Found: C, 73.13; H, 10.53; N, 9.09.

EXAMPLE 142

N-[2,5-bis[(Decylamino)carbonyl]phenyl]-N-(2-methoxy-2oxoethyl)glycine methyl ester A mixture of 1.0 g (2.18 mmol) of N-[2,5-bis[-decylamino)carbonyl]benzenamine, 3.0 ml (32.7 mmol) of methyl bromoacetate, 0.55 g (4 mmol) of potassium carbonate, 0.6 g (4 mmol) of sodium iodide and 0.065 g of tetrabutylammonium bromide in 15 ml of anhydrous DMF was stirred and heated at 100° for 48 hours. The solvent was removed on the oil pump and the residue was taken up in ethyl acetate. The extract was washed with NaHCO$_3$ solution, dried and concentrated to an oil which was purified by chromatography on 100 g of silica gel using 40% ethyl acetate-hexane to give an oil which was crystallized from methanol-water to give 0.308 g, mp 76°-78°, of N-[2,5-bis[(decylamino)carbonyl]phenyl]-N-(2-methoxy-2-oxoethyl)glycine methyl ester.

Anal. Calcd for $C_{34}H_{57}N_3O_6$: C, 67.63; H, 9.51; N, 6.96. Found: C, 67.49; H, 9.46; N, 7.02.

EXAMPLE 143

N-(Carboxymethyl)-N-[2,5-bis[(decylamino)carbonyl]-phenyl]glycine

A solution of 0.3 g (0.5 mmol) of N-[2,5-bis[-(decylamino)carbonyl]phenyl]-N-(2-methoxy-2-oxoethyl)glycine methyl ester and 3.0 ml (3 mmol) of 1 N NaOH in 25 ml of methanol was left at room temperature for 40 hours. The solvent was removed, water was added to the residue and the pH was adjusted to 3-4 with acetic acid. The product was extracted with ethyl acetate and the dried extract was concentrated to an oil which was crystallized from methanol-water to give 0.25 g, mp 135°-136°, of N-(carboxymethyl)-N-[2,5-bis[-(decylamino)carbonyl]phenyl]glycine.

Anal. Calcd for $C_{32}H_{53}N_3O_6$: C, 66.75; H, 9.28; N, 7.30. Found: C, 66.78; H, 9.14; N, 7.32.

EXAMPLE 144

N-(2-Methoxy-2-oxoethyl)-N-[3-(octadecyloxy)-5-[5-[2,3-bisphenylmethoxy)phenyl]pentoxy]phenyl]glycine methyl ester A mixture of 0.903 g (1.73 mmol) of N-[3-hydroxy-5-(oxtadecyloxy)phenyl]-N-(2-methoxy-2-oxoethyl)glycine methyl ester, 0.80 g (1.82 mmol) of 1-(5bromopentyl)-2,3-bis(phenylmethoxy)benzene, 0.48 g (3.46 mmol) of potassium carbonate and 0.26 g (1.73 mmol) of sodium iodide in 30 ml of acetone and 6 ml of DMF was stirred at reflux under argon for a total of 120 hours. After 48 and 96 hours, additional 0.4 g portions of 1-(5-bromopentyl)-2,3-bis(phenylmethoxy)benzene were added. Additional potassium carbonate (0.2 g) was also added after 96 hours. The reaction mixture was filtered through a Celite pad and the filtrate was concentrated at reduced pressure to a yellow oil. Purification by HPLC using 20ethyl acetate-hexane gave 1.086 g (71% yield) of N-(2-methoxy-2-oxoethyl)-N-[3-(octadecyloxy)-5-[5-[2,3-bisphenylmethoxy)phenyl]pentoxyl]-phenyl]glycine methyl ester.

Anal. Calcd for $C_{55}H_{77}NO_8$: C, 75.05; H, 8.82, N, 1.59. Found: C, 75.17; H, 8.87; N, 1.43.

EXAMPLE 145

N-(Carboxymethyl)-N-[3-(octadecyloxy)-5-[5-[2,3-bis(-phenylmethoxy)phenyl]pentoxyl]phenyl]glycine A solution of 1.06 g (1.2 mmol) of N-(2-methoxy-2-oxoethyl)-N-[3-(octadecyloxy)-5-[5-[2,3-bisphenylmethoxy)phenyl]pentoxyl]phenyl]glycine methyl ester and 0.8 ml (4.8 mmol) of 6 N NaOH in 35 ml of methanol and 10 ml of dioxane was stirred at reflux under argon for 4.5 hours. The solvent was removed at reduced pressure and the residue was acidified and extracted with ethyl acetate. The dried extract was concentrated to a solid which was recrystallized from methanol to give 0.93 g (91% yield, mp 79°-81°) of N-(carboxymethyl)-N-[3-(octadecyloxy)-5-[5-[2,3-bis(phenylmethoxy)phenyl]pentoxy]phenyl]glycine.

Anal. Calcd for $C_{53}H_{73}NO_8$: C, 74.70; H, 8.63; N, 1.64 Found: C, 74.71; H, 8.44; N, 1.48.

EXAMPLE 146

N-(Carboxymethyl)-N-[3-[5-(2,3-dihydroxyphenyl)pentoxyl-5-(oxtadecyloxy)phenyl]glycine A mixture of 0.918 g of N-(carboxymethyl)-N-[3-(oxtadecyloxy)-5-[5-[2,3-bis(phenylmethoxy)phenyl]pentoxy]phenyl]glycine and 0.3 g of 10% palladium on carbon in 50 ml of tetrahydrofuran was stirred under a hydrogen atmosphere for 4 hours when absorption ceased. The catalyst was removed by filtration through a Celite pad and the filtrate was concentrated to a solid which was triturated with hexane and filtered to give 0.653 g (97% yield, mp 129°-131°) of N-(carboxymethyl)-N-[3-[5-(2,3-dihydroxyphenyl)pentoxy]-5-(octadecyloxy)phenyl]glycine.

Anal. Calcd for $C_{39}H_{61}NO_8$: C, 69.72; H, 9.15; N, 2.08, Found: 69.72; H, 9.23; N, 2.10.

EXAMPLE 147

N-(2-Methoxy-2-oxoethyl)-N-[3-(octadecyloxy)-5-[(2-quinolinyl)methoxy]phenyl]glycine methyl ester A mixture of 1.5 g (2.9 mmol) of N-[3-hydroxy-5-(octadecyloxy)phenyl]-N-(2-methoxy-2-oxoethyl)glycine methyl ester, 0.935 g (4.35 mmol) of 2-(chloromethyl)-quinoline hydrochloride (Lancaster Organic Research Chemicals), 2.0 g (14.5 mmol) of potassium carbonate and 0.435 g (2.9 mmol) of sodium iodide in 100 ml of acetone and 20 ml of DMF was stirred at reflux under argon for 24 hours. The solvents were removed at reduced pressure and the residue was treated with water and the product was extracted with ethyl acetate. The dried extract was concentrated to a solid which was purified by HPLC using 30% ethyl acetate-hexane followed by recrystallization from hexane to give 1.5 g (78% yield, mp 76°–79°) of N-(2-methoxy-2-oxoethyl)-N-[3-(octadecyloxy)-5-[(2-quinolinyl)methoxy]phenyl]glycine methyl ester.

Anal. Calcd for $C_{40}H_{58}N_2O_6$: C, 72.47; H, 8.82; N, 4.23. Found: C, 72.48; H, 8.93; N, 4.03.

EXAMPLE 148

N-(Carboxymethyl)-N-[3-(octadecyloxy)-5-[(2-quinolinyl)methoxy]phenyl]glycine

A solution of 1.5 g (2.26 mmol) of N-(2-methoxy-2-oxoethyl)-N-[3-(octadecyloxy)-5-[(2-quinolinyl)methoxy]phenyl]glycine methyl ester and 2.0 ml (12 mmol) of 6 N NaOH in 80 ml of methanol was stirred at reflux for 4 hours. The solvent was removed at reduced pressure, the residue was acidified and the product was removed by filtration. Recrystallization from THF-acetone gave 1.0 g (70% yield, mp 172°–174°) of N-(carboxymethyl)-N-[3-(octadecyloxy)-5-[(2-quinolinyl)methoxy]phenyl]glycine.

Anal. Calcd for $C_{38}H_{54}N_2O_6$: C. 71.89; H, 8.57; N, 4.41. Found: C, 71.87; H, 8.78; N, 4.23.

EXAMPLE 149

N-[3-(3Bromopropoxy)-5-(octadecyloxy)phenyl]-N-(2-methoxy-2-oxoethyl)glycine methyl ester A mixture of 4.0 g (7.67 mmol) of N-[3-hydroxy-5-(octadecyloxy)phenyl]-N-(2-methoxy-2-oxoethyl)glycine methyl ester, 7.8 ml (76.6 mmol) of 1,3-dibromopropane and 5.3 g (38.3 mmol) of potassium carbonate in 75 ml of acetone and 15 ml of DMF was stirred at reflux under argon for 41 hours. The reaction mixture was filtered through a Celite pad and the filtrate was concentrated to a solid which was purified by HPLC using 5% ethyl acetate-toluene to give 3.5 g (72% yield, mp 67°–69°) of N-[3-(3-bromopropoxy)-5-(octadecyloxy)phenyl]-N-(2-methoxy-2-oxoethyl) glycine methyl ester. The structure was confirmed by the nmr spectrum.

Anal. Calcd for $C_{33}H_{56}BrNO_6$: C, 61.67; H, 8.78; N, 2.18; Br, 12.43. Found: C, 62.68; H, 9.08; N, 2.12; Br, 11.86.

EXAMPLE 150

1-[3-[3-[bis(Carboxymethyl)amino]-5-(octadecyloxy)phenoxy]propyl]pyridinium hydroxide A solution of 0.76 g of N-[3-(3-bromopropoxy)-5-(octadecyloxy)phenyl]-N-(2-methoxy-2-oxoethyl)glycine methyl ester in 40 ml of pyridine was stirred and heated at 100° for 38 hours. The excess pyridine was removed on the oil pump to a brown solid which was recrystallized from methylene chloride-ether to give 0.58 g (68% yield, mp 120°–123°) of the pyridinium bromide intermediate which was hydroxylzed by dissolving in 20 ml of methanol containing 0.52 ml of 6 N NaOH and stirring at room temperature for 22 hours. The solvent was removed at reduced pressure and the residue was acidified and the product was removed by centrifugation. Recrystallization from methanol-water gave 0.197 g, mp 124°–127°, of 1-[3-[3-[bis(carboxymethyl)amino]-5-(octadecyloxy)phenoxy]propyl]pyridinium hydroxide.

Anal. Calcd for $C_{36}H_{57}N_2O_6.1{:}1$ OH: C, 68.54; H, 9.27; N, 4.44. Found: C, 68.52; H, 9.14; N, 4.29.

EXAMPLE 151

N-[(Carboxymethyl)-N-[3-[2-[2-(2-ethoxyethoxy)ethoxy]ethoxy]-5-(octadecyloxy) phenyl]glycine A solution of 1.76 g (2.58 mmol) of N-(2-methoxy-2-oxoethyl)-N-[3-octadecyloxy-5-(3,6,9-trioxaundec-1-yloxy)phenyl]glycine methyl ester and 2.2 ml (12.9 mmol) of 6 N NaOH in 75 ml of methanol was kept at room temperature for 70 hours. The solvent was removed at reduced pressure and the residue was acidified to pH 2. The product was extracted with ethyl acetate and the dried extract was concentrated at reduced pressure to a solid which was triturated with hexane and filtered to give 1.62 g (96% yield, mp 76°–78°) of N-[(Carboxymethyl)-N-[3-[2-[2-(2-ethoxyethoxy)ethoxy]ethoxy]-5-(octadecyloxy)phenyl]glycine.

Anal. Calcd for $C_{36}H_{63}NO_9$: C, 66.13; H, 9.71; N, 2.14. Found: C, 66.01; H, 9.90; N, 2.08.

EXAMPLE 152

N-(2-Methoxy-2-oxoethyl)-N-[3-(octadecyloxy)-5-[4-[2,3-bis(phenylmethoxy)-6-naphthalenyl]butoxy]phenyl]glycine methyl ester A mixture of 1.5 g (2.88 mmol) of N-[3-hydroxy-5-(octadecyloxy)phenyl]-N-(2-methoxy-2-oxoethyl)glycine methyl ester, 1.24 g (2.88 mmol) of 2-(4-chlorobutyl)-6,7-bis(phenylmethoxy) naphthalene, 0.8 g (5.75 mmol) of potassium carbonate and 0.43 g (2.88 mmol) of sodium iodide in 50 ml of acetone and 10 ml of DMF was stirred at reflux under argon for 40 hours. The acetone was removed by distillation and 50 ml of DMF, 1.24 g of 2-(4-chlorobutyl)-6,7-bis(phenylmethoxy)naphthalene, 0.8 g of potassium carbonate and 0.43 g of sodium iodide was added and the mixture was stirred and heated at 85° for 4 days. The DMF was removed using an oil pump at 55°. The residue was extracted with methylene chloride, the extract was concentrated and the product was purified by HPLC using 20% ethyl acetate-hexane to give 1.3 g (49% yield) of N-(2-methoxy-2-oxoethyl)-N-[3-(octadecyloxy)-5-[4-[2,3-bis(phenylmethoxy)-6-naphthalenyl]butoxy]phenyl]glycine methyl ester as a semisolid. The nmr and mass spectra were consistent with the structure.

EXAMPLE 153

N-(Carboxymethyl)-N-[3-(octadecyloxy)-5-[4-[2,3-bis(phenylmethoxy)-6 naphthalenyl]butoxy]phenyl]glycine A solution of 1.3 g (1.42 mmol) of N-(2-methoxy-2-oxoethyl)-N-[3-(octadecyloxy)-5-[4-[2,3-bis(phenylmethoxy)-6-naphthalenyl]butoxy]phenyl]glycine methyl ester and 0.95 ml (5.68 mmol) of 6 N NaOH in 40 ml of methanol and 15 ml of dioxane was stirred at reflux under argon for 5 hours. The solvents were removed at reduced pressure, the residue was acidified and the product was extracted with ethyl acetate. The dried extract was concentrated to a solid which was recrystallized from methylene chloride-methanol to give 1.18 g, mp 83°–86°, of N-(carboxymethyl)-N-[3-(octadecyloxy)-5-[4-[2,3-bis(phenylmethoxy)-6-naphthalenyl]butoxy]phenyl]glycine. The nmr and mass spectra were consistent with the structure.

Anal. Calcd. for $C_{56}H_{73}NO_8$: C, 75.73; H, 8.28; N, 1.58. Found: C, 74.59; H, 8.42; N, 1.54.

EXAMPLE 154

N-(Carboxymethyl)-N-[3-[4-(2,3-dihydroxy-6-naphthalenyl)butoxy]-5-(octadecyloxy)phenyl]glycine A mixture of 1.16 g of N-(carboxymethyl)-N-[3-(octadecyloxy)-5-[4-[2,3-bis(phenylmethoxy)-6-naphthalenyl]butoxy]phenyl]glycine and 0.35 g of 10% palladium on carbon in 75 ml of THF was stirred under a hydrogen atmosphere until uptake ceased after 6 hours. The catalyst was removed by filtration through a Celite pad and the filtrate was concentrated to a solid which was triturated with hexane and filtered to give 0.835 g (90% yield, mp 153°–155°) of N-(carboxymethyl)-N-[3-[4-(2,3-dihydroxy-6-naphthalenyl)butoxy]-5-(octadecyloxy)phenyl]glycine.

Anal. Calcd for $C_{42}H_{61}NO_8$: C, 71.26; H, 8.69; N, 1.98. Found: C, 71.74; H, 8.79; N, 1.93;

EXAMPLE 155

N-(Carboxymethyl)-N-[3,5-bis[2-[2-(2-ethoxyethoxy)ethoxy]ethoxy]phenyl]glycine

A mixture of 2.0 g (7.43 mmol) of N-[(3,5-dihydroxy)-phenyl]-N-(2-methoxy-2-oxoethyl) glycine methyl ester, 4.3 g (17.8 mmol) of 2-[2-(2-ethoxyethoxy)ethoxy]ethyl bromide, 2.2 g (14.9 mmol) of sodium iodide and 3.1 g (22.3 mmol) of potassium carbonate in 50 ml of acetone and 25 mo of DMF was stirred at reflux under argon for 96 hours. The solvents were removed at reduced pressure and the residual oil was purified by HPLC using 75% ethyl acetate-hexane to give 1.46 g (33% yield) of N-[3,5-bis[2-[2-(2-ethoxyethoxy)ethoxy]ethoxy]phenyl]-N-(2-methoxy-2-oxoethyl)glycine methyl ester as a yellow oil.

Anal. Calcd for $C_{28}H_{47}NO_{12}$: C, 57.03; H, 8.03; N. 2.38. Found: C, 57.08; H, 8.15; N, 2.32.

A solution of 1.41 g (2.39 mmol) of this dimethyl ester and 1.6 ml (9.56 mmol) of 6 N NaOH in 50 ml of methanol was stirred at reflux under argon for 4 hours. The methanol was removed at reduced pressure, the residue was acidified and the product was extracted with ethyl acetate. The dried extract was concentrated to give 1.32 g of N-(carboxymethyl)-N-[3,5-bis[2-[2-(2-ethoxyethoxy)ethoxy]ethoxy]phenyl]glycine as an oil.

Anal. Calcd for $C_{26}H_{43}NO_{12}$; C, 55.60; H, 7.72; N, 2.49. Found: C. 55.89; H, 7.78; N, 2.48.

EXAMPLE 156

N-(Carboxymethyl)-N-[3-[2-[2-(2-methoxyethoxy)ethoxy]ethoxy]-5-(octadecyloxy)phenyl glycine A mixture of 2.0 g (3.83 mmol) of N-[3-hydroxy-5-(oxtadecyloxy)phenyl]-N-(2-methoxy-2-oxoethyl)glycine methyl ester, 4.15 g (15.3 mmol) of 2-[2-[2-(2-methoxyethoxy)ethoxy]ethoxy]ethyl bromide, 1.2 g (7.66 mmol) of sodium iodide and 1.6 g (11.5 mmol) of potassium carbonate in 60 ml of acetone and 30 ml of DMF was stirred at reflux for 48 hours. The solvents were removed at reduced pressure and the residual oil was purified by HPLC using 60% ethyl acetate-hexane to give 2.01 g (73% yield) of N-[3-[2-[2-[2-(2-methoxyethoxy)ethoxy]ethoxy]ethoxy]-5-(octadecyloxy)phenyl]-N-(2-methoxy-2-oxoethyl)glycine methyl ester. The nmr and mass spectra were consistent with the structure.

A solution of 2.0 g (2.81 mmol) of N-[3-[2-[2-(2-methoxyethoxy)ethoxy]ethoxy]ethoxy]-5-(octadecyloxy)phenyl]-N-(2-methoxy-2-oxoethyl)glycine methyl ester and 2.4 ml (14 mmol) of 6 N NaOH in 75 ml of methanol was stirred at room temperature for 22 hours. The solvent was removed at reduced pressure, the residue was acidified and the product was extracted with ethyl acetate. The dried extract was concentrated to a solid which was triturated with hexane and filtered to give 1.58 g (82% yield, mp 63°–65°) of N-(carboxymethyl)-N-[3-8 2-[2(2-methoxyethoxy) ethoxy]ethoxy]ethoxy]-5-(octadecyloxy)phenyl glycine.

Anal. Calcd for $C_{37}H_{65}NO_{10}$: C, 64.98; H; 9.58; N, 2.05. Found: C, 64.75; H, 9.51; N, 1.89.

EXAMPLE 157

N-(Carboxymethyl)-N-[3-[2-[2-[2-(ethoxyethoxy)ethoxy]ethoxy]-5-(tetradecyloxy)phenyl]glycine A mixture of 9.925 g (1.99 mmol) of N-[3-hydroxy-5-(tetradecyloxy)phenyl]-N-(2-methoxy-2-oxoethyl)glycine methyl ester, 1.9 g (7.95 mmol) of 2-[2-(2-ethoxyethoxy)ethoxy]ethyl bromide, 0.6 g (3.97 mmol) of sodium iodide and 0.83 g (5.96 mmol) of potassium carbonate in 30 ml of acetone and 15 ml of DMF was stirred at reflux under argon for 48 hours. The solvents were removed at reduced pressure and the residue was purified by HPLC using 50ethyl acetatehexane to give 9.95 g (77% yield) of N-[3-[2-[2-[2-(ethoxyethoxy)ethoxy]ethoxy]-5-(tetradecyloxy)phenyl]glycine-N-(2-methoxy-2-oxoethyl)glycine methyl ester as an oil. The nmr and mass spectra were consistent with the structure.

A solution of this dimethyl ester (9.5 g, 1.52 mmol) and 1.3 ml of 6 N NaOH in 40 ml of methanol was stirred at room temperature for two days. The methanol was removed at reduced pressure, the residue was acidified and the product was extracted with ethyl acetate. The dried extract was concentrated to a solid which was triturated with hexane and filtered to give 0.83 g (92% yield, mp 65°–67°) of N-(carboxymethyl)-N-[3-[2-[2-[2-(ethoxyethoxy)ethoxy]ethoxy]-5-(tetradecyloxy)-phenyl]glycine.

Anal. Calcd for $C_{32}H_{55}NO_9$: C, 64.30; H, 9.27; N, 2.34. Found: C, 64.29; H, 9.34; N, 2.38.

EXAMPLE 158

N-(2-methoxy-2-oxoethyl)-N-[3-[3-[4-(methylsulfinyl)-phenoxy]propoxy]-5-(octadecyloxy)phenyl]glycine methyl ester A mixture of 1.0 g (1.92 mmol) of N-[3-hydroxy-5-(octadecyloxy)phenyl]-N-(2-methoxy-2oxoethyl)glycine methyl ester, 0.8 g (2.88 mmol) of 1-(3-bromopropoxy)-4-(methylsulfinyl) benzene, 0.3 g (1.92 mmol) of sodium iodide and 0.53 g (3.83 mmol) of potassium carbonate in 30 ml of acetone and 6 ml of DMF was stirred at reflux under argon for 72 hours. The solvents were removed at reduced pressure and the residual oil was purified by HPLC using 50% ethyl acetate-toluene to give 0.76 g (55% yield, mp 67°–69°) of N-(2-methoxy-2-oxoethyl)-N-[3-[3-[3-[4-(methylsulfinyl)phenoxy]proproxy]-5-(octadecyloxy)phenyl]glycine methyl ester.

Anal. Calcd for $C_{40}H_{63}NO_8S$: C, 66.91; H, 8.84; N, 1.95; S, 4.47. Found: C, 66.60; H, 8.92; N, 2.06; S, 4.65.

EXAMPLE 159

N-(Carboxymethyl)-N-[3-[3-[4-(methylsulfinyl)phenoxy]propoxy]-5-(octadecyloxy)phenyl glycine A solution of 0.73 g (1.02 mmol) of N-(2-methoxy-2-oxoethyl)-N-[3-[3-(4-(methylsulfinyl)phenyl]propoxy]-5-(octadecyloxy)phenyl]glycine methyl ester and 0.68 ml (4.08 mmol) of 6 N NaOH in 30 ml of methanol was stirred at reflux under argon for 4 hours. The methanol was removed at reduced pressure, the residue was acidified and the product was extracted with ethyl acetate. The dried extract was concentrated to a solid which was recrystallized from acetonehexane to give 0.57 g (82% yield, mp 124°–126°) of N-(carboxymethyl)-N-[3-[3-[4-methylsulfinyl)phenoxy]propoxy]-5-(octadecyloxy)phenyl glycine.

Anal. Calcd for $C_{38}H_{59}NO_8S$; C, 66.15; H, 8.62; N, 2.03; S, 4.65. Found: C, 66.21; H, 8.71; N, 2.00; S, 4.35.

EXAMPLE 160

N-(2-Methoxy-2-oxoethyl)-N-[3-[3-[4-(methylsulfonyl)phenoxy]propoxyl]-5-(octadecyloxy)phenyl]glycine methyl ester A mixture of 1.0 g (1.92 mmol) of N-[3-hydroxy-5-(octadecyloxy)phenyl]-N-(2-methoxy-2-oxoethyl)glycine methyl ester, 0.84 g (2.88 mmol) of 1-(3-bromopropoxy)-4-methylsulfonyl) benzene, 0.53 g (3.83 mmol) of potassium carbonate and 0.3 g (1.92 mmol) of sodium iodide in 30 ml of acetone and 6 ml of DMF was stirred at reflux under argon for 72 hours. The solvents were removed at reduced pressure and the residual oil was purified by three recrystallizations from methylene chloride-methanol to give 1.03 g (73% yield, mp 70°–72°) of N-(2-methoxy-2-oxoethyl)-N-[3-[3-[4-(methylsulfonyl)phenoxy]propoxy]-5-octadecyloxy)-phenyl]glycine methyl ester.

Anal. Calcd for $C_{40}H_{63}NO_9S$; C, 65.45; H, 8.65; N, 1.91 S, 4.37. Found: C, 65.18; H, 8.73; N, 1.88; S, 4.46.

EXAMPLE 161

N-(Carboxymethyl)-N-[3-[3-[4-(methylsulfonyl)phenoxy]propoxy]-5-(octadecyloxy)phenyl]glycine A solution of 1.01 g (1.37 mmol) of N-(2-methoxy-2-oxoethyl)-N-[3-[3-[4-(methylsulfonyl) phenoxy]propoxy]-5-(octadecyloxy)-phenyl]glycine methyl ester and 0.92 ml (5.5 mmol) of 6 N NaOH in 30 ml of methanol was stirred at reflux for 4 hours under argon. The methanol was removed at reduced pressure, the residue was acidified and the product was extracted with ethyl acetate. The dried extract was concentrated to a solid which was recrystallized from methylene chloride-ether to give 0.835 g (86% yield, mp 118°–120°) of N-(carboxymethyl)-N-[3-[3-[4-(methylsulfonyl)phenoxy]propoxy]-5-(octadecyloxy)phenyl]glycine.

Anal. Calcd for $C_{38}H_{59}NO_9S$: C, 64.65; H, 8.42; N, 1.98; S, 4.54. Found: C, 6.75; H, 8.49; N, 1.93; S, 4.29.

EXAMPLE 162

N-(Carboxymethyl)-N-[3-(octadecyloxy)-5-[[(trifluoromethyl)sulfonyl]amino]phenyl]glycine To 0.25 g (0.48 mmol) of N-[3-amino-5-(octadecyloxy)phenyl]-N-(2-methoxy-2-oxoethyl) glycine methyl ester and 0.1 ml (0.72 mmol) of triethylamine in 4 ml of anhydrous methylene chloride cooled in an ice bath was added 0.08 ml (0.48 mmol) of trifluoromethanesulfonic anhydride in 1 ml of methylene chloride. After one hour, an additional 0.01 ml of trifluoromethanesulfonic anhydride was added. The mixture was stirred for 30 minutes, and it was washed with $NaHCO_3$ solution, dried and concentrated at reduced pressure to a solid. Purification by chromatography on 15 g of silica gel using 50% ethyl acetate-hexane gave 0.176 g, mp 96°–98° (56% yield) of N-(2-methoxy-2-oxoethyl)-N-[3-(octadecyloxy)-5-[[(trifluoromethyl)sulfonyl]aminophenyl]glycine methyl ester. The structure was confirmed by nmr and mass spectra. A solution of 0.17 g (0.26 mmol) of N-(2-methoxy-2-oxoethyl)-N-[3-(octadecyloxy)-5-[[(trifluoromethyl)sulfonyl]aminophenyl]glycine methyl ester in 10 ml methanol and 0.22 ml (1.3 mmol) of 6 N NaOH was stirred at reflux under an argon atmospheres for 2 hours. The solvent was removed at reduced pressure and the residue was dissolved in water and acidified with 6 N NCl. The resultant precipitate was extracted with ethyl acetate and the dried extract was concentrated to a solid which was triturated with hexane and filtered to give 0.15 g (95% yield), mp 163°–165°, of N-(carboxy-methyl)-N-[3-(octadecyloxy)-5-8 [(trifluoromethyl)sulfonyl]amino]-phenyl]glycine.

Anal. Calcd for $C_{29}H_{47}F_3N_2O_7S$; C, 55.75; H, 7.58; N, 4.48; F, 9.12; S, 5.13. Found: C, 55.34; H, 7.60; N, 4.40; F, 8.97; S. 4.84.

EXAMPLE 163

3-(Methylthio)-5-(octadecyloxy)benzoic acid

A mixture of 2.54 g (12.8 mmol) of 3-hydroxy-5-methylthiobenzoic acid methyl ester, 4.7 g (14.1 mmol) of 1-bromooctadecane and 2.7 g (19.2 mmol) of potassium carbonate in 60 ml of anhydrous DMP was stirred and heated at 80° under an argon atmosphere for 21 hours. The reaction mixture was filtered through a Celite pad and the filtrate was concentrated at reduced pressure. Water was added to the residue and the product was filtered and recrystallized from methylene chloride-methanol to give 5.5 g (95% yield), mp 64°–66°, of 3-(methylthio)-5-(octadecyloxy)benzoic acid methyl ester. The nmr and mass spectra were consistent with the structure. A solution of 2.7 g (6 mmol) of 3-(methylthio)-5-(octadecyloxy)benzoic acid methyl ester and 5.0 ml (30 mmol) of 6 N NaOH in 125 ml of methanol was stirred at reflux under argon for 5 hours. The solvent was removed at reduced pressure, the residue was acidified with 6 N HCl and the product was extracted with chloroform. The dried extract was concentrated to a solid which was triturated with hexane and filtered to give 2.6 g, mp 90°–92°, of 3-(methylthio)-5-(octadecyloxy)benzoic acid. The nmr and mass spectra were consistent with the structure.

EXAMPLE 164

3-(Methylthio)-5-(octadecyloxy)benzenamine

A mixture of 2.57 g (5.89 mmol) of 3-(methylthio)-5-(octadecyloxy)benzoic acid, 1.5 ml (7.1 mmol) of diphenylphosphoryl azide 5.5 ml (58.9 mmole) t-butanol and 1.0 ml (7.1 mmol) of triethylamine in 25 ml of anhydrous toluene was stirred at reflux under argon for 19 hours. The reaction mixture was concentrated at reduced pressure and the product was extracted with methylene chloride. The extract was washed with $NaHCO_3$ solution and the dried extract was concentrated to a solid which was purified by chromatography on 20 g of silica gel using 50% methylene chloride-hexane to give 2.67 g (89% yield), mp 73°–75°, of 3-(methylthio)-5-(octadecyloxy)phenylcarbamic acid dimethylethyl ester. The nmr and mass spectra were consistent with the structure.

A solution of 2.65 g (5.2 mmol) of 3-(methylthio)-5-(octadecyloxy)phenylcarbamic acid dimethylethyl ester and 2.0 ml (26 mmol) of trifluoroacetic acid in 50 ml of methylene chloride was kept at room temperature for 24 hours. The mixture was concentrated at reduced pressure and the residue was treated with excess NaHCO$_3$ solution. The product was extracted with the methylene chloride and the dried extract was concentrated and recrystallized from methylene chloride-hexane to give 1.85 (87% yield), mp 75°–77° of 3-(methylthio)-5-(octadecyloxy)benzenamine. The nmr and mass spectra were consistent with the structure.

EXAMPLE 165

N-(2-Methoxy-2-oxoethyl)-N-[3-(methylthio)-5-(octadecyloxy)phenyl]glycine methyl ester and [[3-bis(2-methoxy-2-oxoethyl)amino]-5-(octadecyloxy)phenyl]thio]acetic acid methyl ester A mixture of 1.83 g (4.49 mmol) of 3-(methylthio)-5-(octadecyloxy)benzenamine, 1.3 ml (13.5 mmol) of methyl bromoacetate, 2.4 g (11.2 mmol) of 1.8-bis(dimethylamino)naphthalene and 0.2 g (1.3 mmol) of sodium iodide in 40 ml of acetonitrile and 10 ml of DMP was stirred and heated at reflux under argon for 48 hours. The reaction mixture was filtered, the filtrate was concentrated to a solid which was treated with 200 ml of 0.5 N HCl and the product was extracted with ethyl acetate. The extract was washed with NaHCO$_3$ solution, dried and concentrated to a solid which was purified by HPLC using 20% ethyl acetate-hexane to give 0.32 g (13% yield), mp 78°–80°, of N-(2-Methoxy-2-oxoethyl)-N-[3-(methylthio)-5-(octadecyloxy)phenyl]glycine methyl ester. The structure was confirmed by nmr and mass spectra which were compatible. Later fractions from the HPLC were concentrated to give 0.83 g which was further purified by chromatography on 40 of silica gel using 20% ethyl acetate-hexane to give 0.50 g (18% yield), mp 68°–70°, of [[3-bis(2-methoxy-2-oxoethyl)amino]-5-(octadecyloxy)phenyl]thio]acetic acid methyl ester. The structure was confirmed by nmr and mass spectra which were compatible.

EXAMPLE 166

N-(Carboxymethyl)-N-[3-(methylthio)-5-(octadecyloxy)phenyl]glycine

A solution of 0.32 g (0.58 mmol) of N-(2-Methoxy-2-oxoethyl)-N-[3-(methylthio)-5-(octadecyloxy)phenyl]glycine methyl ester and 0.4 ml (2.4 mmol) of 6 N NaOH in 15 ml of methanol was stirred at reflux under argon for 2.5 hours. The solvent was removed at reduced pressure, the residue was acidified and the product was extracted with ethyl acetate. The dried extract was concentrated to a solid which was triturated with hexane and filtered to give 0.287 g (94% yield), mp 129°–130°, of N-(carboxymethyl)-N-[3-(methylthio)-5-(octadecyloxy)phenyl]glycine.

Anal. Calcd for C$_{29}$H$_{49}$NO$_5$S: C, 66.50; N, 9.43; N, 2.67. Found: C, 66.77; H, 9.63; N, 2.64.

EXAMPLE 167

[[3-[bis(2-Methoxy-2-oxoethyl)amino]-5-(octadecyloxy)phenyl]sulfinyl]acetic acid methyl ester To a solution of 0.45 g (0.74 mmol) of [[3-bis(2-methoxy-2-oxoethyl)amino]-5-(octadecyloxy)phenyl]thio]acetic acid methyl ester in 30 ml of methylene chloride cooled in an ice bath was added 0.22 g (1.08 mmol) of 85% 3-chloroperoxybenzoic acid. After stirring in the ice bath for 3 hours, the solution was washed with NaHCO$_3$, dried and concentrated to a solid which was purified by chromatography on 40 g of silica gel using 50% ethyl acetate-hexane to give 0.4 g, mp 81°–83°, of [[3-[bis(2-methoxy-2-oxoethyl)amino]-5-(octadecyloxy)phenyl]sulfinyl]acetic acid methyl ester.

Anal. Calcd for C$_{33}$H$_{55}$NO$_8$S: C, 63.33; H, 8.86; N, 2.24; S, 5.12. Found: C, 63.23; H, 8.99; N, 2.18; S, 5.15.

EXAMPLE 168

[[3-[bis(Carboxymethyl)amino]-5-(octadecyloxy)phenyl]sulfinyl]acetic acid

A solution of 0.57 g (0.91 mmol) of [[3-[bis(2-methoxy-2-oxoethyl)amino]-5-(octadecyloxy)phenyl]sulfinyl]acetic acid methyl ester and 0.76 ml (4.55 mmol) of 6 N NaOH in 100 ml of methanol was stirred at reflux under argon for 6 hours. The solvent was removed at reduced pressure, the residue was acidified and the product was extracted with ethyl acetate. The dried extract was concentrated to a solid which was triturated with hexane and filtered to give 0.42 g (80% yield), mp 138°–140°, of [[3-[bis(carboxymethyl)amino]-5-(octadecyloxy)phenyl]sulfinyl]acetic acid.

Anal. Calcd for C$_{30}$H$_{49}$NO$_8$S: C, 61.72; H, 8.46; N, 2.40; S, 5.49. Found: C, 61.49; H, 8.52; N, 2.36; S, 5.44.

EXAMPLE 169

3-(methylsulfinyl)-5-(octadecyloxy)benzoic acid

To 2.32 g (5.15 mmol) of 3-(methylthio)-5-(octadecyloxy)benzoic acid methyl ester in 100 ml of methylene chloride cooled and stirred in an ice bath was added 1.5 g (7.4 mmol) of 85% 3-chloroperoxybenzoic acid. The reaction mixture was stirred in the ice bath for 1.5 hours, washed with NaHCO$_3$ solution, dried and concentrated to a solid which was purified by chromatography on 40 g of 230–400 mesh silica gel using 50% ethyl acetate-hexane to give 1.9 g (79% yield), mp 66°–68°, of 3-(methylsulfinyl)-5-(octadecyloxy)benzoic acid methyl ester. The nmr and mass spectra were consistent with the structure.

To 1.88 g (4.03 mmol) of 3-(methylsulfinyl)-5-(octadecyloxy)benzoic acid methyl ester in 75 ml of methanol was added 2.0 ml (12 mmol) of 6 N NaOH and the solution was stirred at reflux under argon for 2.5 hours and then was kept at room temperature for 14 hours. The solvent was removed at reduced pressure, the residue was acidified and the product wax extracted with ethyl acetate. The dried extract was concentrated at reduced pressure to a solid which was triturated with hexane and filtered to give 1.77 g, mp 110°–112°, of 3-(methylsulfinyl)-5-(octadecyloxy)benzoic acid.

Anal. Calcd for C$_{26}$H$_{44}$O$_4$S: C, 68.98; H, 9.80; S, 7.08. Found: C, 69.05; H, 9.51; S, 7.02.

EXAMPLE 170

3-(Methylsulfinyl)-5-(octadecyloxy)benzenamine

A mixture of 1.66 g (3.67 mmol) of 3-(methylsufinyl)-5-(octadecyloxy)benzoic acid, 3.4 ml of t-butanol (freshly distilled from sodium), 0.95 ml (4.4 mmol) of diphenylphosphoryl azide and 0.6 ml (4.4 mmol) of triethylamine in 20 ml of anhydrous toluene was stirred at reflux under argon for 19 hours. The reaction mixture was concentrated at reduced pressure and NaHCO$_3$ solution was added to the residue. The product was extracted with methylene chloride and the dried extract was concentrated at reduced pressure to a solid which was purified by chromatography on 30 g of silica gel using 50% ethyl acetate-hexane to give 1.52 g (79% yield), mp 91°–93°, of 3-(methylsulfinyl)-5-(octadecyloxy)phenylcarbamic acid dimethylethyl ester.

A solution of 1.5 g (2.86 mmol) of 3-(methylsulfinyl)-5-(octadecyloxy)phenylcarbamic acid dimethylethyl ester and 1.1 ml (14.3 mmol) of trifluoroacetic acid in 50 ml of methylene chloride was kept at room temperature for 41 hours. The solvent was removed at reduced pressure, the residue was treated with $NaHCO_3$ solution and the product was extracted with methylene chloride. The dried extract was concentrated at reduced pressure to a solid which was recrystallized from methylene chloride-hexane to give 1.13 g (94% yield), mp 104°–106°, of 3-(methylsufinyl)-5-(octadecyloxy)benzenamine.

Anal. Calcd for $C_{25}H_{45}NO_2S$: C, 70.87; H, 10.71; N, 3.31; S, 7.57. Found: C, 71.00; H, 1053; N, 3.27; S, 7.34.

Example 171

N-(2-Methoxy-2-oxoethyl)-N-[3(methylsulfinyl)-5-(octadecyloxy)phenyl]glycine methyl ester A mixture of 1.12 g (2.64 mmol) of 3-(methylsulfinyl)-5-(octadecyloxy)benzenamine, 0.75 ml (7.93 mmol) of methyl bromoacetate, 1.42 g (6.61 mmol) of 1,8-dimethylaminonaphthalene and 0.11 g (0.74 mmol) of sodium iodide in 25 ml of anhydrous acetonitrile and 6 ml of anhydrous DMF was stired and heated under argon for 96 hours. The solvents were removed at reduced pressure, 50 ml of 0.5 N HCl was added to the residue and the product was extracted with ethyl acetate. The dried extract was concentrated at reduced pressure to an oil which was purified by HPLC using 75% ethyl acetate-hexane followed by two recrystallizations from methylene chloride-hexane gave 0.55 g (36% yield), mp 80°–82°, of N-(2-methoxy-2-oxoethyl)-N-[3-(methylsulfinyl)-5-(octadecyloxy)phenyl]glycine methyl ester.

Anal. Calcd for $C_{31}H_{53}NO_6S$: C, 65.57; H, 9.41; N, 2.47; S, 5.65. Found: C, 65.52; H, 9.18; N, 2.42; S, 5.92.

EXAMPLE 172

N-(Carboxymethyl)-N-[3-(methylsulfinyl)-5-(octadecyloxy)phenyl]glycine

A solution of 0.53 g (0.93 mmol) of N-(2-methoxy-2-oxoethyl)-N-[3-(methylsulfinyl)-5-(octadecyloxy)phenyl]glycine methyl ester and 0.8 ml (4.7 mmol) of 6 N NaOH in 40 ml of methanol was stirred at reflux under argon for 6 hours. The solvent was removed at reduced pressure, the residue was acidified and the product was extracted with 10% THF-ethyl acetate. The dried extract was concentrated to a solid which was recrystallized from THF-ethyl acetate to give 0.42 g (84% yield), mp 147°–149°, of N-(carboxymethyl)-N-[3-(methylsufinyl)-5-(octadecyloxy)phenyl]glycine.

Anal. Calcd for $C_{29}H_{49}NO_6S$: C, 64.53; H, 9.15; N, 2.59; S, 5.95. Found: C, 64.40; H, 9.05; N, 2.42; S, 5.82.

EXAMPLE 173

3-(Di-decylaminocarbonyl)benzenamine

To an ice bath cooled solution of 0.80 g (2.69 mmol) of di-decylamine and 0.75 mL (5.4 mmol) of triethylamine in 10 mL of anhydrous methylene chloride was added dropwise a solution of 0.50 g (2.69 mmol) of 3-nitrobenzoyl chloride in 5 mL of methylene chloride with stirring. The mixture was stirred at room temperature for 4 hours. Water was added, the organic layer was separated and dried. The solvent was removed at reduced pressure and the residual oil was purified by chromatography on 30 g of silica gel using 12.5% ethyl acetate-hexane to give 1.0 g of 3-(di-decylaminocarbonyl)-1-nitrobenzene as an oil. The nmr and mass spectra were consistent with the structure. A mixture of 1.0 g of 3-(di-decylaminocarbonyl)-1-nitrobenzene and 0.2 g of 10% palladium on carbon in 20 mL of ethyl acetate and 20 mL of THF was stirred under a hydrogen atmosphere at room temperature for 2 hours when hydrogen uptake ceased. The catalyst was removed by filtration and the filtrate was concentrated to give 1.0 g of 3-(di-decylaminocarbonyl)benzenamine as an oil. The nmr and mass spectra were consistent with the structure.

EXAMPLE 174

N-(Carboxymethyl)-N-[3-di-decylaminocarbonyl)-phenyl]glycine

A mixture of 1.0 g (2.4 mmol) of 3-(di-decylaminocarbonyl)benzenamine, 3.8 mL (24 mmol) of benzylbromoacetate, 1.3 g (6 mmol) of 1,8-bis(dimethylamino)naphthalene and 0.36 g (2.4 mmol) of sodium iodide in 20 mL of anhydrous acetonitrile and 5 mL of DMF was stirred under argon at reflux for 40 hours. The solvents were removed at reduced pressure, water was added and the product was extracted with ethyl acetate. The dried extract was concentrated at reduced pressure and the residue was purified by HPLC using 20% ethyl acetate-hexane to give 1.2 g (70% yield) of N-[3-(di-decylaminocarbonyl)phenyl]-N-[2-oxo-2-(phenylmethoxy)ethyl]glycine phenylmethyl ester as an oil. The nmr and mass spectra were consistent with the structure. A mixture of 1.2 g of N-[3-(di-decylaminocarbonyl)phenyl]-N-[2-oxo-2-(phenylmethoxy)ethyl]glycine phenylmethyl ester and 0.4 g of 10% palladium on carbon in 15 mL. of ethyl acetate and 15 mL of THF was stirred under a hydrogen atmosphere at room temperature for 4.5 hours when hydrogen uptake ceased. The catalyst was removed by filtration and the filtrate was concentrated to an oil which was triturated with ether-hexane and filtered to give 0.6 g (67% yield, mp 133°–136°) of N-(carboxymethyl)-N-[3-di-decylaminocarbonyl)-phenyl]glycine.

Anal. Calcd for $C_{31}H_{52}N_2O_5$: C, 69.19; H, 10.07; N, 5.38. Found: C, 69.38; H, 9.85; N, 5.27.

EXAMPLE 175

N-[[3-(Octadecyloxy)-5-(tricyclo[3.3.1.1/3.7/]dec-1-ylcarbonyl)oxy]phenyl]glycine A mixture of 0.36 g (0.67 mmol) of 3-(octadecyloxy)-5-[(tricyclo[3.3.1.1/3,7/]dec-1-ylcarbonyl)oxy]benzenamine, 0.31 mL (2.0 mmol) of benzylbromoacetate, 0.44 g (2.0 mmol) of 1,8-bis(dimethylamino)naphthalene and 0.11 g (0.7 mmol) of sodium iodide in 10 mL of acetonitrile and 13 mL of DMF was stirred and refluxed under argon for 72 hours. The solvents were removed at reduced pressure, ethyl acetate was added to the residue and the extract was washed with 0.01 N HCl, with $NaHCO_3$ solution, dried and concentrated at reduced pressure to an oil. Purification by chromatography on 75 g of silica gel using 15% ethyl acetate-hexane gave 0.177 g of N-[[3-(octadecyloxy)-5-(tricyclo[3.3.1.1/3,7/]dec-1-ylcarbonyl)oxy]phenyl]glycine phenylmethyl ester as an oil. The nmr and mass spectra were consistent with the structure. A mixture of 0.17 g of N-[[3-(octadecyloxy)-5-tricyclo[3.3.1.1/3,7/]dec-1-ylcarbonyl)oxy]phenyl]glycine phenylmethyl ester and 0.1 g of 10% palladium on carbon was shaken under an initial hydrogen pressure of 54 psi on a Parr Hydrogenator for 2.5 hours. The catalyst was removed at reduced pressure and the filtrate was concentrated at reduced pressure to 0.12 g of N-[[3-(octadecyloxy)-5-(tricyclo[3.3.1.1/3,7/]dec-1-ylcarbonyl)oxy]phenyl]glycine as a semisolid. The nmr and mass spectra were consistent with the structure.

EXAMPLE 176

N-[3-[3-[4-(1,1-Dimethylethyl)phenoxy]propoxy]-5-(octadecyloxy)phenyl]-N-(2-methoxy-2-oxoethyl)glycine methyl ester A mixture of 1.0 g (1.92 mmol) of N-[3-hydroxy-5-(octadecyloxy)phenyl]-N-(2-methoxy-2-oxoethyl)glycine methyl ester, 0.55 g (2.0 mmol) of 4-(3-bromopropoxy)-1,1-dimethylethyl, 0.53 g (3.8 mmol) of potassium carbonate and 0.29 g (1.92 mmol) of sodium iodide in 30 mL of anhydrous acetone and 6 mL of anhydrous DMF was stirred at reflux under argon for 65 hours. The solvents were removed at reduced pressure and the residue was extracted with methylene chloride. The extract was concentrated to a solid which was recrystallized from methylene chloride-methanol to give 0.85 g (62 % yield, mp 56°–58°) of N-[3-[3-[4-(1,1-dimethylethyl) phenoxy]propoxy]-5-(octadecyloxy)phenyl]-N-(2-methoxy-2-oxoethyl)glycine methyl ester.

Anal. Calcd for $C_{43}H_{69}NO_7$: C, 72.54; H, 9.77; N, 1.97. Found: C. 72.78; H, 9.94; N, 204.

EXAMPLE 177

N-(Carboxymethyl)-N-[3-[3-[4-(1,1-dimethylethyl)-phenoxy]propoxy]-5-(octadecyloxy)phenyl]glycine A solution of 0.815 g (1.14 mmol) of N-[3-[3-[4-(1,1-dimethylethyl)phenoxy]propoxy]-5-(octadecyloxy)-phenyl]-N-(2-methoxy-2-oxoethyl)glycine methyl ester and 0.76 mL of 6 N NaOH in 20 mL of methanol-10 mL of dioxane was stirred at reflux under argon for 5 hours. The solvents were removed at reduced pressure, the residue was acidified with dilute HCl and the product was extracted with ethyl acetate. The dried extract was concentrated at reduced pressure and the residue was crystallized from methanol-water to give 0.72 g (92% yield, mp 99°–101°) of N-(carboxymethyl)-N-[1-[3-[4-(1,1-dimethylethyl)phenoxy]propoxy]-5-(octadecyloxy) phenyl]glycine.

Anal. Calcd for $C_{41}H_{65}NO_7$: C, 72.00; H, 9.57; N, 2.05. Found: C, 72.25; H, 9.94; N, 2.04.

EXAMPLE 178

3-Amino octadecanoate (ester)

A solution of 1.3 mL (8 mmol) of octadecanoyl chloride in 5 mL of methylene chloride was added dropwise to a solution of 1.0 g (7.2 mmol) of 3-nitrophenol and 2.2 mL (16 mmol) of triethylamine in 30 mL of methylene chloride with stirring at room temperature. After stirring for 2 hours, 100 mL of ether was added and the mixture was washed with 1N NaOH, dried and concentrated at reduced pressure to 1.5 g, mp 64°–65°, of 3-nitrophenol octadecanoate.

A mixture of 1.5 g of 3-nitrophenol octadecanoate (ester) and 0.3 g of 10% palladium on carbon in 50 mL of ethyl acetate was shaken under an initial hydrogen pressure of 52 psi on a Parr hydrogenator until uptake ceased after 4.5 hours. The usual workup and recrystallization from methanol-water gave 0.7 g, mp 46°–47°, of 3aminophenol octadecanonate (ester). The nmr spectrum was consistent with the structure.

Using this procedure heptadecyl isocyanate was treated with 3-nitrophenol to give heptadecyl carbamic acid 3-nitrophenyl ester (mp 66°–73°, Anal. Calcd for $C_{24}H_{40}N_2O_4$: C, 68.54; H, 9.59; N, 6.66. Found: C, 68.44; H, 9.88; N, 6.41) which was hydrogenated to give heptadecylcarbamic acid 3-aminophenyl ester (mp 69°–75°, Anal. Calcd for $C_{24}H_{42}N_2O_4$: C, 73.80; H, 10.84; N, 7.17. Found: C, 73.79; H, 11.08; N, 6.84).

EXAMPLE 179

N-(3-Aminophenyl)-N'-octadecylurea

A mixture of 0.5 g (3.6 mmol) of 3-nitroaniline, 1.2 mL (3.9 mmol) of octadecyl isocyanate 0.7 mL (5 mmol) of triethylamine and 0.1 mL of 4-dimethylaminopyridine in 30 mL of anhydrous THF was stirred at reflux for 18 hours. The reaction mixture was concentrated at reduced pressure and the residue was recrystallized from THF methanol-water to give 1.3 g of N-(3-nitrophenyl)-N'-octadecylurea.

A mixture of 1.3 g of N-(3-nitrophenyl)-N'-octadecylurea and 0.5 g of 10% palladium on carbon in 60 mL of THF was shaken under an initial hydrogen pressure of 52 psi in a Parr hydrogenator unitl uptake ceased after 2 hours. The usual workup and recrystallization from methanol-water gave 1.0 g, mp 102°–104°, of N-(3-aminophenyl)-N'-octadecylurea. Anal. Calcd for $C_{25}H_{45}N_3O$: C, 74.39; H, 11.24; N, 10.41. Found; C, 74.34; H, 11.11; N, 9.87).

EXAMPLE 180

3-(Octadecyloxy)-5-(2,2-diphenyl-1-oxoethoxy)benzoic acid phenylmethyl ester

Diphenylacetyl chloride [from the reaction of 2.0 g (4.7 mmol) of diphenylacetic acid with thionyl chloride] dissolved in 20 ml of methylene chloride was added dropwise to an ice cooled solution of 2.0 g (4.0 mmol) of 3-hydroxy-5-(octadecyloxy)benzoic acid phenylmethyl ester and 1.1 ml (8.0 mmol) of triethylamine in 50 ml of methylene chloride with stirring. The reaction mixture was stirred with ice bath cooling for 1 hours and then at room temperature for 20 hours and then was washed with 1 N HCl and with NaHCO₃ solution. After drying the solvent was removed at reduced pressure and the crude product was purified by chromatography on 50 g of silica gel using 10% ethyl acetate-hexane to give 2.5 g, mp 47°–49°, of 3-(octadecyloxy)-5-(2,2-diphenyl-1-oxoethoxy)benzoic acid phenylmethyl ester. The nmr and mass spectra were consistent with the structure.

EXAMPLE 181

3-(Octadecyloxy)-5-[(tricyclo[3,3,1,1/3,7/]dec-1-ylcarbonyl)oxy]benzoic acid phenylmethyl ester 1-Adamantane carboxylic acid chloride (0.067 g) in 1 mL of methylene chloride was added to a stirred solution of 0.153 g of 3-hydroxy-5-octadecyloxy)benzoic acid phenylmethyl ester and 0.09 mL of triethylamine in 10 mL of methylene chloride. The reaction mixtures was stirred at room temperature for 17 hours and was then washed with 1N HCl and with NaHCO₃ solution. After drying the solvent was removed at reduced pressure and the crude product was purified by chromatography on 20 g silica gel using 10% ethyl acetate-hexane to give 0.163 g of 3-(octadecyloxy)-5-[(tricyclo[3.3.1.1/3,7/]dec-1-ylcarbonyl)oxy]benzoic acid phenylmethyl ester as an oil. The nmr spectrum served to confirm the structure.

EXAMPLE 812

N-[3-Hydroxy-5-[(12-phenoxydodecyl)oxy]phenyl]-N-(2-methoxy-2-oxoethyl)glycine methyl ester and N-(2-Methoxy-2-oxoethyl)-N-[3,5-bis[(12-phenoxydodecyl)oxy]phenyl]glycine methyl ester A mixture of 1.0 g (3.7 mmol) of N-[(3,5-dihydroxy)phenyl]-N-(2-methoxy-2-oxoethyl)glycine methyl ester, 1.27 g (3.7 mmol) of 12-phenoxydodecyl bromide and 0.51 g (3.7 mmol) of potassium carbonate in 20 ml of DMF was stirred and heated at 80° for 24 hours under argon. The usual workup followed by purification by chromatography on 40 g of silica gel. Elution was 25% ethyl acetate-hexane gave 0.57 g, mp 61°-63°, of N-(2-methoxy-2-oxoethyl)-N-[3,5-bis[(12-phenoxydodecyl)oxy]phenyl]glycine methyl ester. Elution was 50% ethyl acetate-hexane gave 0.53 g, mp 65°-67°, of N-[3-hydroxy-5-[(12-phenoxydodecyl)oxy]phenyl]-N-(2-methoxy-2oxoethyl)glycine methyl ester.

Anal. Calcd for $C_{30}H_{43}NO_7$: C, 68.93; H, 8.18; N, 2.64. Found: C, 67.93; H, 8.07; N, 2.57.

EXAMPLE 183

N-[3,5-bis[(12-Phenoxydodecyl)oxy]phenyl]-N-(carboxymethyl)glycine

A solution of 3.5 g (4.43 mmol) of N-(2-methoxy-2-oxoethyl)-N-[3,5-bis[(12-phenoxydodecyl)oxy]phenyl]glycine methyl ester and 3 ml (18 mmol) of 6 N NaOH in 150 ml of methanol and 50 ml of dioxane was stirred at reflux under argon for 19 hours. The usual workup followed by recrystallization from acetone-hexane gave 3.2 g, mp 72°-74°, of N-[3,5-bis[(12-phenoxydodecyl)oxy]phenyl]-N-(carboxymethyl)glycine.

Anal. Calcd for $C_{46}H_{67}NO_8$: C, 72.50; H, 8.86; N, 1.84. Found: C, 72.37; H, 9.02; N, 1.86.

EXAMPLE 184

N-[3-[2-[2-(2-Ethoxyethoxy)ethoxy]ethoxy]-5-[(12-phenoxydodecyl)oxy]phenyl]-N-(2-methoxy-2-oxoethyl)glycine methyl ester A mixture of 1.2 g (2.27 mmol) of N-[3-hydroxy-5[(12-phenoxydodecyl)oxy]phenyl]-N-(2-methoxy-2-oxoethyl)glycine methyl ester, 2.73 g (11.37 mmol) of 2-[2-(2-ethoxyethoxy)ethoxy]ethyl bromide, 0.94 g (6.8 mmol) of potassium carbonate and 1.0 g (6.8 mmol) of sodium iodide in 40 ml of acetone and 20 ml of DMF was stirred at reflux under argon for 64 hours. After the usual workup the product was purified by HPLC using 40% ethyl acetate-hexane to give 1.16 g (74% yield), mp<24°, of N-[3-[2-[2-(2-ethoxyethoxy)ethoxy]ethoxy]-4-[(12-phenoxydodecyl)oxy]phenyl]-N-(2-methoxy-2-oxoethyl)glycine methyl ester.

EXAMPLE 185

N-(Carboxymethyl)-N-[2-[2-[2-(2-ethoxyethoxy)ethoxy]ethoxy]-5-[(12-phenoxydodecyl)oxy]phenyl]glycine A solution of 1.15 g (1.67 mmol) of N-[3-[2-[2-(2-ethoxyethoxy)ethoxy]ethoxy]-5-[(12-phenoxydodecyl)oxy]phenyl]-N-(2-methoxy-2-oxoethyl)glycine methyl ester and 1.4 ml (8.4 mmol) of 6 N NaOH in 50 ml of methanol and 10 ml of dioxane was stirred at reflux under argon for 19 hours. After the usual workup the product was crystallized from acetone-hexane to give 0.94 g (85% yield), mp 58°-61°, of N-(carboxymethyl)-N-[3-[2-[2-(2-ethoxyethoxy)-ethoxy]ethoxy]-5-[(12-phenoxydodecyl)oxy]phenyl]glycine.

Anal. Calcd for $C_{36}H_{55}NO_{10}$: C, 65.33; H, 8.38; N, 2.12. Found: C, 65.24; H, 8.49; N, 1.99.

EXAMPLE 186

N-(2-Methoxy-2-oxoethyl)-N-[3-[3-[4-methylsulfinyl)phenoxy]propoxy]-5-[(12-phenoxydodecyl)oxy]phenyl]glycine methyl ester A mixture of 1.5 g (2.83 mmol) of N-[3-hydroxy-5-[(12-phenoxydodecyl)oxy]phenyl]-N-(2-methoxy-2-oxoethyl)glycine methyl ester, 1.2 g (4.25 mmol) of 3-[(4-methylsulfinyl) phenoxy]propyl bromide, 0.78 g (5.66 mmol) of potassium carbonate and 0.64 g (4.25 mmol) of sodium iodide in 40 ml of acetone and 10 ml of DMF was stirred at reflux under argon for 6 days. The usual workup followed by purification by chromatography on 45 g of 230–400 mesh silica gel using 10% ethyl acetate-hexane gave 1.1 g (54% yield), mp 47°-49°, of N-(2-methoxy-2-oxoethyl)-N-[3-[3-[4-(methylsulfinyl)phenoxy]propoxy]-5-[(12-phenoxy-dodecyl) oxyl]phenyl]glycine methyl ester.

EXAMPLE 187

N-(Carboxymethyl)-N-[3-[3-[4-(methylsulfinyl)phenoxy]propoxy]-5-[(12-phenoxydodecyl)oxy]phenyl]glycine A solution of 1.1 g (1.52 mmol) of N-(2-methoxy-2-oxoethyl)-N-[3-[3-[4-(methylsulfinyl)phenoxy]propoxy]-5-[(12-phenoxy-dodecyl)oxy]phenyl]glycine methyl ester and 1.3 ml (7.8 mmol) of 6 N NaOH in 100 ml of methanol was stirred at reflux under argon for 4 hours. After the usual workup the product was recrystallized from acetone-hexane to give 0.93 g (88% yield), mp 106°-108°, of N-(carboxymethyl)-N-[3-[3-[4-(methylsulfinyl)phenoxy]propoxy]-5-[(12-phenoxydodecyl)oxy]phenyl]glycine.

Anal. Calcd for $C_{38}H_{51}NO_9S$: C, 65.40; H, 7.37; N, 2.01; S, 4.59. Found: C 65.25; H, 7.38; N, 2.13; S, 4.58.

EXAMPLE 188

N-[3-[6-(2,3-Bisphenylmethoxy)phenyl]hexyloxy]-5-[(12-phenoxydodecyl)oxy]phenyl]-N-(2-methoxy-2-oxoethyl)glycine methyl ester A mixture of 1.7 g (3.2 mmol) of N-[3-hydroxy-5-[(12-phenoxydodecyl)oxy]phenyl]-N-(2-methoxy-2-oxoethyl)glycine methyl ester, 1.5 g (3.37 mmol) of 1-(6-bromohexyl)-2,3-bis(phenylmethoxy)benzene, 1.3 g (9.6 mmol) of potassium carbonate and 0.96 g (6.4 mmol) of sodium iodide in 60 ml of acetone and 20 ml of DMF was stirred at reflux under argon for 7 days. The usual workup followed by purification by HPLC using 25% ethyl acetate-hexane gate 2.15 g (74% yield) of N-[3-[6-(2,3-bisphenylmethoxy)phenyl]hexyloxy]-5-[(12-phenoxydodecyl)oxy]phenyl]-N-(2-methoxy-2-oxoethyl)glycine methyl ester as an oil. The nmr and mass spectra were consistent with the structure.

EXAMPLE 189

N-(Carboxymethyl)-N-3-[6-[(2,3-bisphenylmethoxy)phenyl]hexyloxy]-5-[(12-phenoxydodecyl)oxy]phenyl]glycine A solution of 2.13 g (2.36 mmol) of N-[3-[6-(2,3-bisphenylmethoxy)phenyl]hexyloxy]-5-[(12-phenoxydodecyl)oxy]phenyl]-N-(2-methoxy-2-oxoethyl)glycine methyl ester and 2.0 ml (12 mmol) of 6 N NaOH in 125 ml of methanol and 25 ml of dioxane was stirred at reflux under argon for 6 hours. After the usual workup, the product was purified by crystallization from acetonehexane to give 1.78 g (86% yield, mp 81°–84°) of N-(carboxymethyl)-N-3-[6-[(2,3-bisphenylmethoxy)-phenyl]hexyloxy]-5-[(12-phenoxydodecyl)oxy]-phenyl]glycine.

Anal. Calcd for $C_{54}H_{67}NO_9$: C, 74.20; H, 7.73; N, 1.60. Found: C, 74.48; H, 7.84; N, 1.81.

EXAMPLE 190

N-(Carboxymethyl)-N-[3-[6-(2,3-dihydroxyphenyl)hexyloxy]-5-[(12-phenoxydodecyl)oxy]phenyl]glycine A mixture of 1.74 g of N-(carboxymethyl)-N-3-[6-[(2,3-bisphenylmethoxy)phenyl]hexyloxy]-5-[(12-phenoxydodecyl)oxy]phenyl]glycine and 0.6 g of 10% palladium on carbon in 100 ml of THF was stirred under a hydrogen atmosphere until uptake ceased after 3 hours. After the usual workup, the product was purified by trituration with hexane to give 1.26 g (91% yield, mp 129°–131°) of N-(carboxymethyl)-N-[3-[6-(2,3-dihydroxyphenyl)hexyloxy]-5-[(12-phenoxydodecyl)oxy]phenyl]glycine.

Anal. Calcd for $C_{40}H_{55}NO_9$: C, 69.24; H, 7.99; N, 2.02. Found: C, 69.24; H, 7.85; N, 1.93.

EXAMPLE 191

TABLET FORMULATION (Wet Granulation)

| Item | Ingredient | mg/tablet | | |
|---|---|---|---|---|
| | | 25 mg | 100 mg | 500 mg |
| 1. | N-[(carboxymethyl)-N-[3-[2-[2-(2-ethoxyethoxy)ethoxy]ethoxy]-5-(octadecyloxy)phenyl glycine | 25 | 100 | 500 |
| 2. | Lactose Anhydrous | 143 | 132 | — |
| 3. | Pregelatinized Starch | 10 | 16 | 30 |
| 4. | Modified Starch | 20 | 30 | 40 |
| 5. | Magnesium Stearate | 2 | 2 | 6 |
| | Total | 200 | 280 | 576 |

Manufacturing Procedure:
1. Mix Items 1, 2 3 and 4 and granulate with water.
2. Dry the granulation at 50° C.
3. Pass the granulation through suitable milling equipment.
4. Add Item 5 and mix for three minutes; compress on a suitable press.

EXAMPLE 192

CAPSULE FORMULATION

| Item | Ingredient | mg/capsule | | | |
|---|---|---|---|---|---|
| 1. | N-[(carboxmethyl)-N-[2-[2-(2-ethoxyethoxy)ethoxy]ethoxy]-5-(octadecyloxy)phenyl glycine | 25 | 50 | 100 | 500 |
| 2. | Lactose Hydrous | 143 | 168 | 148 | — |
| 3. | Corn Starch | 20 | 20 | 40 | 70 |
| 4. | Talc | 10 | 10 | 10 | 25 |
| 5. | Magnesium Stearate | 2 | 2 | 2 | 5 |
| | Total | 200 | 250 | 300 | 600 |

Manufacturing Procedure:
1. Mix Items 1, 2 and 3 in a suitable mixer for 30 minutes.
2. Add Items 4 and 5 and mix for 3 minutes.
3. Fill into suitable capsules.

We claim:
1. A compound of the formula

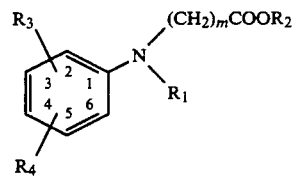

wherein
$R_1$ is hydrogen or —$(CH_2)_mCOOR_2$;
$R_2$ is hydrogen, $(R_6)_2N(CH_2)_2$—; $R_6COOCH_2$— or —$CH_2CON(CH_2CH_2OH)_2$;
$R_3$ is hydrogen, nitro, hydroxy, amino, $CH_3(CH_2)_nS(O)_{0-2}$—, $CH_3(CH_2)_nO$—, $R_5COO$—, $R_5OOC$—, $R_5HNCOO$—, $R_5NHCO$—, $R_5CONH$—, $R_5NHCONH$—, $[CH_3(CH_2)_n]_2NCO$—, $CH_3(CH_2)_nCHOHCH_2O$—, (2-quinolinyl)methoxy, oleyloxy, linoleyloxy, $R_8OOC(CH_2)_oO$—, $(R_6)_2PO(CH_2)_pO$—, (HO)$(R_6O)PO(CH_2)_pO$—, $R_6[(CH_2)_2]_qO$—, $R_7(CH_2)_pO$—, or —$O(CH_2)_p$-pyridinium+-(OH—);
$R_4$ is $CH_3(CH_2)_nO$—, $CF_3SO_2NH$—, $R_5COO$—, $R_5OOC$—, $R_5HNCOO$—, $R_5NHCO$—, $R_5NHCONH$—, $[CH_3(CH_2)_n]_2NCO$—, $CH_3(CH_2)_nCHOHCH_2O$—, carboxy, (2-quinolinyl)methoxy, oleyloxy, linoleyloxy, $R_8OOC(CH_2)_oO$—, $R_6[O(CH_2)_2]_qO$—, $R_7(CH_2)_pO$—;
$R_5$ is $CH_3(CH_2)_n$—, 1-adamantyl or diphenylmethyl;
$R_6$ is lower alkyl;
$R_7$ is 1- or 2-naphthyloxy, 1-, 2- or 3-pyridinyloxy, 2,3- or 3,4-dihydroxyphenyl, 6,7-dihydroxy-2-naphthyl, phenyl, phenoxy or substituted phenyl or phenoxy, wherein the substituent is selected from the group consisting of lower alkyl, lower alkoxy, hydroxy, nitro, amino, halo, $R_6S(O)_{0-2}$—, carboxy, carboxy-lower alkyl or phenyl;
$R_8$ is hydrogen or lower alkyl;
n is an integer for 0 to 17;
m is an integer from 1 to 3;
o is an integer from 1 to 10;
p is an integer from 2 to 18, and
q is an integer from 1 to 6;
or when $R_2$ is hydrogen, a pharmaceutically acceptable salt thereof with a base.

2. A compound, in accordance with claim 1, wherein $R_1$ is hydrogen.

3. A compound, in accordance with claim 1, wherein $R_1$ is —$(CH_2)_mCOOR_2$.

4. A compound, in accordance with claim 3, wherein $R_2$ is hydrogen.

5. A compound, in accordance with claim 3, wherein m is 1 to 2, $R_3$ and $R_4$, are the same and are $CH_3(CH_2)_nO$— or $CH_3(CH_2)_nNHCO$—, n is 3 to 17 and the substitution pattern is:

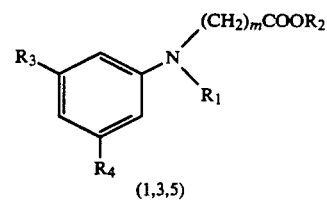

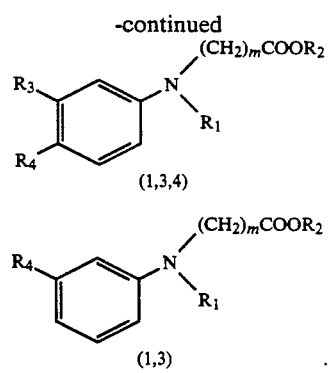

(1,3,4)

(1,3)

6. A compound, in accordance with claim 3, wherein m is 1-2, $R_3$ is $CH_3(CH_2)_nO—$, wherein n is 3-17 and $R_4$ is $R_8OOC(CH_2)_oO—$, $R_6[O(CH_2)_2]_qO—$, $R_7(CH_2)_pO—$, $R_5O_2C—$ or $CF_3SO_2NH—$.

7. A compound, in accordance with claim 4, wherein m is 1, $R_3$ and $R_4$, are the same and are $CH_3(CH_2)_nO—$, or $CH_3(CH_2)_nNHCO—$ wherein n is 3-17 and the substitution pattern is 1,3,5 or 1,3,4.

8. A compound in accordance with claim 4, wherein m is 1, $R_3$ is hydrogen, $R_4$ is $CH_3(CH_2)_nO—$ wherein n is 9-17 and the substitution pattern is 1,3.

9. A compound in accordance with claim 4, wherein m is 1, $R_3$ is $CH_3(CH_2)_nO—$ wherein n is 9-17 and $R_4$ is $R_8OOC(CH_2)_oO—$ wherein o is 1-6, $R_7(CH_2)_pO—$ wherein $R_7$ is 2,3-dihydroxyphenyl or substituted phenoxy and p is 3-5, carboxy, $CF_3SO_2NH—$, or $R_6[O(CH_2)_2]_qO—$ wherein q is 2-5 and the substitution pattern is 1,3,5.

10. A compound in accordance with claim 4, wherein m is 1, $R_3$ and $R_4$ are the same and are $CH_3(CH_2)_nO—$ wherein n is 7-13 and the substitution pattern is 1,3,5.

11. A compound in accordance with claim 4, wherein m is 1, $R_3$ is $CH_3(CH_2)_nO—$ wherein n is 9-17 and $R_4$ is $R_8OOC(CH_2)_oO—$ wherein $R_8$ is hydrogen or methyl and o is 1-4, carboxy, $CF_3SO_2NH—$, or $R_{68}O(CH_2)_2]_qO—$ wherein q is 2-3 unsubstituted or substitute 3-phenoxypropoxy wherein the substituent is selected from the group consisting of lower alkoxy, hydroxy, nitro, amino, methylsulfinyl, methylsulfonyl, and the substituent pattern is 1,3,5.

12. A compound, in accordance with claim 3, wherein

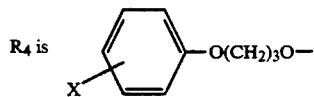

wherein X is hydrogen, methoxy, hydroxy, nitro, amino, methylthio or methylsulfonyl.

13. A compound, in accordance with claim 1, N-(carboxymethyl)-N-[3-[3-(4-hydroxyphenoxy)propoxy[-5-(octadecyloxy)phenyl]glycine.

14. A compound, in accordance with claim 1, N-(carboxymethyl)-N-[3-[2-[2-(2-ethoxyethoxy)ethoxy]ethoxy]-5-(octadecyloxy)phenyl]glycine.

15. A compound, in accordance with claim 1, N-(carboxymethyl)-N-[3-[3-[4-(methylsufinyl)phenoxy]-propoxy]-5-(octadecyloxy)-phenyl]glycine.

16. A compound, in accordance with claim 1, N-(carboxymethyl)-N-[3-[5-(2,3-dihydroxyphenyl)pentoxy]-5-(octadecyloxy)-phenyl]glycine.

17. A compound, in accordance with claim 1, N-(carboxymethyl)-N-[3-(octadecyloxy)-5-[[(trifluoromethyl)sulfonyl]amino]phenyl]glycine.

18. A compound, in accordance with claim 1, selected from the group consisting of
N-(carboxymethyl)-N-[3,5-bis(dodecyloxy)phenyl]glycine;
N-(carboxymethyl)-N-[3,5-bistetradecyloxy)phenyl]glycine.
N-(carboxymethyl)-N-[3-(octadecyloxy)-5-[(5-methoxy-5-oxopentyl)oxy]phenyl]glycine;
N-[3-(4-carboxybutoxy)-5-(octadecyloxy)phenyl]-N-(carboxymethyl)glycine;
N-(carboxymethyl)-N-[3-(octadecyloxy)-5-(3-phenoxy)propoxy)phenyl]glycine;
N-(carboxymethyl)-N-[3-[3-(3-methoxyphenoxy)-propoxy]-5-(octadecyloxy)phenyl]glycine;
N-(carboxymethyl)-N-[3-[3-(4-methoxyphenoxy)-propoxy]-5-(octadecyloxy)phenyl]glycine;
N-(carboxymethyl)-N-[3-[3-(3-nitrophenoxy)propoxy]-5-(octadecyloxy)phenyl]glycine;
N-(carboxymethyl)-N-[3-[3-(3-aminophenoxy)propoxy]-5-(octadecyloxy)phenyl]glycine;
N-(carboxymethyl)-N-[3-(methoxycarbonyl)-5-(octadecyloxy)phenyl]glycine;
N-[3-carboxy-5-(octadecyloxy)phenyl]-N-(carboxymethyl)glycine;
N-(carboxymethyl)-N-[3-[3-[4-(methylsulfonyl)phenoxy]propoxy]-5-(octadecyloxy)phenyl]glycine; and
N-(carboxymethyl)-N-[3-[4-(2,3-dihydroxy-6-naphthalene)butoxy]-5-(octadecyloxy)phenyl]glycine.

19. Method of inhibiting phospholipases $A_2$ which comprises administering to a host requiring such treatment a therapeutically effective amount of a compound of the formula

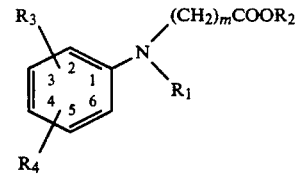

wherein
$R_1$ is hydrogen or $—(CH_2)_mCOOR_2$;
$R_2$ is hydrogen, $(R_6)_2N(CH_2)_2—$, $R_6COOCH_2—$ or $—CH_2CON(CH_2CH_2OH)_2$;
$R_3$ is hydrogen, nitro, hydroxy, amino, $CH_3(CH_2)_nS(O)_{0-2}—$, $CH_3(CH_2)_n—$, $CH_3(CH_2)_nO—$, $R_5COOO—$, $R_5OOC—$, $R_5HNCOO—$, $R_5NHCO—$, $R_5CONH—$, $R_5NHCONH—$, $[CH_3(CH_2)_n]_2NCO—$, $CH_3(CH_2)_nCHOHCH_2O—$, (2-quinolinyl)methoxy, oleyloxy, linoleyloxy, $R_8OOC(CH_2)_oO—$, $(R_6O)_2PO(CH_2)_pO—$, $(HO)(R_6O)PO(CH_2)_pO—$, $R_6[O(CH_2)_2]_qO—$, $R_7(CH_2)_pO—$ or $—O(CH_2)_{p^-}$ pyridinium$^+$(OH$^-$);
$R_4$ is $CH_3(CH_2)_n—$, $CH_3(CH_2)_nO—$, $CF_3SO_2NH—$, $R_5COO—$, $R_5OOC—$, $R_5HNCOO—$, $R_5NHCO—$, $R_5NHCONH—$, $[CH_3(CH_2)_n]_2NCO—$, $CH_3(CH_2)_nCHOHC-H_2O—$, carboxy, (2-quinolinyl)methoxy, oleyloxy, linoleyloxy, $R_8OOC(CH_2)_oO—$, $R_6[O(CH_2)_2]_qO—$, $R_7(CH_2)_pO—$;
$R_5$ is $CH_3(CH_2)_n—$, 1-adamantyl or diphenylmethyl;
$R_6$ is lower alkyl;

115

R$_7$ is 1- or 2-naphthyloxy, 1-, 2- or 3-pyridinyloxy, 2,3- or 3,4-dihydroxyphenyl, 6,7-dihydroxy-2-naphthyl, phenyl, phenoxy or substituted phenyl or phenoxy, wherein the substituent is selected from the group consisting of lower alkyl, lower alkoxy, hydroxy, nitro, amino, halo, R$_6$S(O)$_{0-2}$—, carboxy, carboxy-lower alkyl or phenyl;

R$_8$ is hydrogen or lower alkyl;

n is an integer from 0 to 17;

m is an integer from 1 to 3;

o is an integer from 1 to 10;

p is an integer from 2 to 18, and q is an integer from 1 to 6;

or when R$_2$ is hydrogen, a pharmaceutically acceptable salt thereof with a base.

20. A method, in accordance with claim 19, wherein R$_1$ is hydrogen.

21. A method, in accordance with claim 19, wherein R$_1$ is —(CH$_2$)$_m$COOR$_2$.

22. A method, in accordance with claim 21, wherein R$_2$ is hydrogen.

23. A method, in accordance with claim 19, which is used to treat psoriasis or dematitis.

24. A method, in accordance with claim 19, which is used to treat inflammatory bowel disease.

25. A method, in accordance with claim 19, wherein m is 1, R$_3$ is CH$_3$(CH$_2$)$_n$O— wherein n is 9-17 and R$_4$ is R$_8$OOC(CH$_2$)$_o$O— wherein R$_8$ is hydrogen or methyl and o is 1-4 carboxy, CF$_3$SO$_2$NH—, R$_6$[O(CH$_2$)$_2$]$_q$O— wherein q is 2-3 or unsubstituted or substituted 3-phenoxypropoxy wherein the substituent is selected from the group consisting of lower alkoxy, hydroxy, nitro, amino, methylsulfinyl, methylsulfonyl, and the substitution pattern is 1,3,5.

26. A method, in accordance with claim 19, N-(carboxymethyl)-N-[3,5-bis-(decyloxy)phenyl]glycine.

27. A method, in accordance with claim 19, N-(carboxymethyl)-N-[3-[3-(4-hydroxyphenyl)proproxy]-5-(octadecyloxy)phenyl]glycine.

28. A method, in accordance with claim 19, N-(carboxymethyl)-N-[3-[2-[2-(2-ethoxyethoxy)ethoxy]ethoxy]-5-(octadecyloxy)phenyl]glycine.

29. A method, in accordance with claim 19, N-(carboxymethyl)-N-[3-[3-[4-(methylsulfinyl)phenoxy]-propoxy]-5-(octadecyloxy)-phenyl]glycine.

30. A method, in accordance with claim 19, N-(carboxymethyl)-N-[3-[5-(2,3-dihydroxyphenyl)pentoxy]-5-(octadecyloxy)-phenyl]glycine.

31. A method, in accordance with claim 19, N-(carboxymethyl)-N-[3-(octadecyloxy)-5-[[(trifluoromethyl)sulfonyl]amino]phenyl]glycine.

32. A method, in accordance with claim 19, selected from the group consisting of N-(carboxymethyl)-N-[3,5-bis(dodecyloxy)phenyl]glycine;

N-(carboxymethyl)-N-[3,5-bistetradecyloxy)phenyl]glycine;

N-(carboxymethyl)-N-[3-(octadecyloxy)-5-[(5-methoxy-5-oxopentyl)oxy]phenyl]glycine;

N-[3-(4-carboxybutoxy)-5-(octadecyloxy)phenyl]-N-(carboxymethyl)glycine;

N-(carboxymethyl)-N-[3-(octadecyloxy)-5-(3-phenoxypropoxy)phenyl]glycine;

N-(carboxymethyl)-N-[3-[3-(3-methoxyphenoxy)-propoxy]-5-(octadecyloxy)phenyl]glycine;

N-(carboxymethyl)-N-[3-[3-(4-methoxyphenoxy)-propoxy]-5-(octadecyloxy)phenyl]glycine;

116

N-(carboxymethyl)-N-[3-[3-(3-nitrophenoxy)propoxy]-5-(octadecyloxy)phenyl]glycine;

N-(carboxymethyl)-N-[3-[3-(3-aminophenoxy)propoxy]-5-(octadecyloxy)phenyl]glycine;

N-(carboxymethyl)-N-[3-(methoxycarbonyl)-5-(octadecyloxy)phenyl]glycine;

N-[3-carboxy-5-(octadecyloxy)phenyl]-N-(carboxymethyl)glycine;

N-(carboxymethyl)-N-[3-[3-[4-(methylsulfonyl)phenoxy]propoxy]-5-(octadecyloxy)phenyl]glycine; and N-(carboxymethyl)-N-[3-(4-(2,3-dihydroxy-6-naphthalene)butoxy]-5-(octadecyloxy)phenyl]glycine.

33. A pharmaceutical composition which comprises a compound of the formula

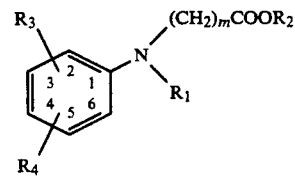

wherein

R$_1$ is hydrogen or —(CH$_2$)$_m$COOR$_2$;

R$_2$ is hydrogen, (R$_6$)$_2$N(CH$_2$)$_2$—, R$_6$COOCH$_2$— or —CH$_2$CON(CH$_2$CH$_2$OH)$_2$;

R$_3$ is hydrogen, nitro, hydroxy, amino, CH$_3$(CH$_2$)$_n$S(O)$_{0-2}$—, CH$_3$(CH$_2$)$_n$O—, R$_5$COO—, R$_5$OOC—, R$_5$HNCOO—, R$_5$NHCO—, R$_5$CONH—, R$_5$NHCONH—, [CH$_3$(CH$_2$)$_n$]$_2$NCO—, CH$_3$(CH$_2$)$_n$CHOHCH$_2$O—, (2-quinolinyl)methoxy, oleyloxy, linoleyloxy, R$_8$OOC(CH$_2$)$_o$O—, (R$_6$O)$_2$PO(CH$_2$)$_p$O—, (HO)(R$_6$O)PO(CH$_2$)$_p$O—, R$_6$[O(CH$_2$)$_2$]$_q$O—, R$_7$(CH$_2$)$_p$O—, or —O(CH$_2$)$_p$-pyridinium$^+$(OH$^-$);

R$_4$ is CH$_3$(CH$_2$)$_n$O—, CF$_3$SO$_2$NH—, R$_5$COO—, R$_5$OOC—, R$_5$HNCOO—, R$_5$NHCO—, R$_5$NHCONH—, [CH$_3$(CH$_2$)$_n$]$_2$NCO—, CH$_3$(CH$_2$)$_n$CHOHCH$_2$O—, carboxy, (2-quinolinyl)methoxy, oleyloxy, linoleyloxy, R$_8$OOC(CH$_2$)$_o$O—, R$_6$[O(CH$_2$)$_2$]$_q$O—, R$_7$(CH$_2$)$_p$O—;

R$_5$ is CH$_3$(CH$_2$)$_n$—, 1-adamantyl or diphenylmethyl;

R$_6$ is lower alkyl;

R$_7$ is 1- or 2-naphthyloxy, 1-, 2- or 3-pyridinyloxy, 2,3- or 3,4-dihydroxyphenyl, 6,7-dihydroxy-2-naphthyl, phenyl, phenoxy or substituted phenyl or phenoxy, wherein the substituent is selected from the group consisting of lower alkyl, lower alkoxy, hydroxy, nitro, amino, halo, R$_6$S(O)$_{0-2}$—, carboxy, carboxy-lower alkyl or phenyl;

R$_8$ is hydrogen or lower alkyl;

n is an integer from 0 to 17;

m is an integer from 1 to 3;

o is an integer from 1 to 10;

p is an integer from 2 to 18, and q is an integer from 1 to 6;

or when R$_2$ is hydrogen, a pharmaceutically acceptable salt thereof with a base, and an inert carrier.

34. A pharmaceutical composition, in accordance with claim 33, wherein R$_1$ is hydrogen.

35. A pharmaceutical composition, in accordance with claim 33, wherein R$_1$ is R$_2$OOC(CH$_2$)$_m$.

36. A pharmaceutical composition, in accordance with claim 34, wherein R$_2$ is hydrogen.

37. A pharmaceutical composition, in accordance with claim 33, wherein m is 1, R$_3$ is CH$_3$(CH$_2$)$_n$O— wherein n is 9–17 and $R_4$ is $R_8OOC(CH_2)_oO$— wherein $R_8$ is hydrogen or methyl and o is 1–4, carboxy, $CF_3SO_2NH$—, $R_6[O(CH_2)_2]_qO$— wherein q is 2–3 or unsubstituted or substituted 3-phenoxypropoxy wherein the eubstituent is selected from the group consisting of lower alkoxy, hydroxy, nitro, amino, methylsulfinyl, methylsulfonyl, and the substitution pattern is 1,3,5.

38. A pharmaceutical composition, in accordance with claim 33, N-(carboxymethyl)-N-[3,5-bis(decyloxy)phenyl]glycine.

39. A pharmaceutical composition, in accordance with claim 33, N-(carboxymethyl)-N-[3-[3-(4-hydroxyphenoxy)propoxy]-5-(octadecyloxy)phenyl]glycine.

40. A pharmaceutical composition, in accordance with claim 33, N-(carboxymethyl)-N-[3-[2-[2-(2-ethoxyethoxy)ethoxy]ethoxy]-5-(octadecyloxy)phenyl]glycine.

41. A pharmaceutical composition, in accordance with claim 33, N-(carboxymethyl)-N-[3-[3-[4-(methylsulfinyl)phenoxy]propoxy]-5-(octadecyloxy)-phenyl]glycine.

42. A pharmaceutical composition, in accordance with claim 33, N-(carboxymethyl)-N-[3-[5-(2,3-dihydroxyphenyl)pentoxy]-5-(octadecyloxy)-phenyl]glycine.

43. A pharmaceutical composition, in accordance with claim 33, N-(carboxymethyl-N-[3-(octadecyloxy)-5-[[(trifluoromethyl)sulfonyl]amino]phenyl]glycine.

44. A pharmaceutical composition, in accordance with claim 33, select from the group consisting of
N-(carboxymethyl)-N-[3,5-bis(dodecyloxy)phenyl]glycine;
N-(carboxymethyl)-N-[3,5-bistetradecyloxy)phenyl]glycine;
N-(carboxymethyl)-N-[3-(octadecyloxy)-5-[(5-methoxy-5-oxopentyl)oxy]phenyl] glycine;
N-[3-(4-carboxybutoxy)-5-(octadecyloxy)phenyl]-N-(carboxymethyl)glycine;
N-(carboxymethyl)-N-[3-(octadecyloxy)-5-(3-phenoxypropoxy)phenyl]glycine;
N-(carboxymethyl)-N-[3-[3-(3-methoxyphenoxy)propoxy]-5-(octadecyloxy)phenyl]glycine;
N-(carboxymethyl)-N-[3-[3-(4-methoxyphenoxy)propoxy]-5-(octadecyloxy)phenyl]glycine;
N-(carboxymethyl)-N-[3-[3-(3-nitrophenoxy)propoxy]-5-(octadecyloxy)phenyl]glycine;
N-(carboxymethyl)-N-[3-[3-(3-aminophenoxy)propoxy]-5-(octadecyloxy)phenyl]glycine;
N-(carboxymethyl)-N-[3-(methoxycarbonyl)-5-(octadecyloxy)phenyl]glycine;
N-[3-carboxy-5-(octadecyloxy)phenyl]-N-(carboxymethyl)glycine;
N-(carboxymethyl)-N-[3-[3-[4-(methylsulfonyl)phenoxy]propoxy]-5-(octadecyloxy)phenyl]glycine; and
N-(carboxymethyl)-N-[3-[4-(2,3-dihydroxy-6-naphthalene)butoxy]-5-(octadecyloxy)phenyl}glycine.

* * * * *